(12) United States Patent
Wang

(10) Patent No.: US 11,292,839 B2
(45) Date of Patent: Apr. 5, 2022

(54) TREATMENT AND SUSTAINED VIROLOGIC REMISSION OF HIV INFECTION BY ANTIBODIES TO CD4 IN HAART STABILIZED PATIENTS

(71) Applicant: UBI US Holdings LLC, Hauppauge, NY (US)

(72) Inventor: Chang Yi Wang, Cold Spring Harbor, NY (US)

(73) Assignee: UBI US Holdings, LLC, Hauppauge, NY (US)

( * ) Notice: Subject to any disclaimer, the term of this patent is extended or adjusted under 35 U.S.C. 154(b) by 0 days.

(21) Appl. No.: 16/325,361

(22) PCT Filed: Aug. 13, 2017

(86) PCT No.: PCT/US2017/046668
§ 371 (c)(1),
(2) Date: Feb. 13, 2019

(87) PCT Pub. No.: WO2018/035001
PCT Pub. Date: Feb. 22, 2018

(65) Prior Publication Data
US 2019/0194326 A1    Jun. 27, 2019

Related U.S. Application Data

(60) Provisional application No. 62/374,752, filed on Aug. 13, 2016.

(51) Int. Cl.
| | |
|---|---|
| A61K 39/00 | (2006.01) |
| A61K 38/00 | (2006.01) |
| A61K 38/17 | (2006.01) |
| A61K 39/395 | (2006.01) |
| A61K 45/06 | (2006.01) |
| C07K 16/28 | (2006.01) |
| A61P 31/18 | (2006.01) |

(52) U.S. Cl.
CPC ...... *C07K 16/2812* (2013.01); *A61K 39/3955* (2013.01); *A61K 45/06* (2013.01); *A61P 31/18* (2018.01); *A61K 2039/505* (2013.01); *A61K 2039/54* (2013.01); *A61K 2039/545* (2013.01); *C07K 2317/24* (2013.01); *C07K 2317/34* (2013.01); *C07K 2317/73* (2013.01); *C07K 2317/76* (2013.01); *C07K 2317/92* (2013.01)

(58) Field of Classification Search
CPC .......... A61K 2300/00; A61K 39/39558; A61K 38/21; A61K 2039/505; A61K 2039/545
See application file for complete search history.

(56) References Cited

U.S. PATENT DOCUMENTS

| | | |
|---|---|---|
| 5,171,838 A | 12/1992 | Chiba |
| 5,912,176 A | 6/1999 | Wang |
| 5,961,976 A | 10/1999 | Wang |
| 5,962,319 A | 10/1999 | Ogawa et al. |
| 6,090,388 A | 7/2000 | Wang |
| 7,501,494 B2 | 3/2009 | Lynn et al. |
| 2003/0186900 A1 | 10/2003 | Omura et al. |
| 2003/0211470 A1 | 11/2003 | Olson et al. |
| 2004/0137000 A1 | 7/2004 | Lynn et al. |
| 2009/0053220 A1 | 2/2009 | Duensing et al. |
| 2009/0060914 A1 | 3/2009 | Lynn et al. |
| 2009/0214569 A1 | 8/2009 | Wang et al. |
| 2011/0300069 A1 | 12/2011 | Emmrich et al. |
| 2016/0017038 A1 | 1/2016 | Koenig |
| 2017/0369576 A1 | 12/2017 | Wang |

FOREIGN PATENT DOCUMENTS

| | | |
|---|---|---|
| AU | 629847 | 3/1990 |
| EP | 0018794 | 11/1980 |
| EP | 0365209 | 4/1990 |
| EP | 1034790 | 9/2000 |
| EP | 1083226 | 3/2001 |
| JP | H02238883 | 9/1990 |
| JP | H06125783 | 5/1994 |
| JP | H1070986 | 3/1998 |
| JP | H10155489 | 6/1998 |
| RU | 2250770 | 4/2005 |
| RU | 2393873 C2 | 7/2010 |
| WO | 1990002199 | 3/1990 |
| WO | 1992/009305 | 6/1992 |
| WO | 1993012227 | 6/1993 |
| WO | 1995024483 | 9/1995 |
| WO | 1998052976 | 11/1998 |
| WO | 2006/117586 A1 | 11/2006 |

(Continued)

OTHER PUBLICATIONS

International Search Report issued in corresponding International Application No. PCT/US2017/046668, dated Jan. 18, 2018.
Written Opinion of the International Searching Authority issued in corresponding International Application No. PCT/US2017/046668, dated Jan. 18, 2018.
Monroe, K.M., et al. "IFI16 DNA Sensor Is Required for Death of Lymphoid CD4 T-cells Abortively Infected with HIV", Science, 343(6169)1428-432 (2014).
EESR as issued in European Application No. 17841919 dated Feb. 20, 2020, 7 pp.

(Continued)

*Primary Examiner* — Barry A Chestnut
(74) *Attorney, Agent, or Firm* — Locke Lord LLP; Peter N. Fill; Nicholas J. DiCeglie, Jr.

(57) ABSTRACT

The present disclosure is directed to compositions and methods for the prevention, treatment, and/or functional cure of HIV infection. One aspect of the present disclosure relates to monoclonal antibodies directed against CD4, compositions thereof, and methods employing such compositions for the prevention, treatment, and functional cure of HIV infection.

63 Claims, 34 Drawing Sheets

Specification includes a Sequence Listing.

(56) References Cited

FOREIGN PATENT DOCUMENTS

| WO | WO2016043788 | * | 3/2013 |
| WO | 2014/039840 A1 | | 3/2014 |
| WO | 2016/043788 | | 3/2016 |
| WO | WO2018035001 | * | 2/2018 |

OTHER PUBLICATIONS

Kuritzkes, D., et al., "Antiretroviral activity of the anti-CD4 monoclonal antibody TNX-355 in patients infected with HIV type 1", Journal of Infectious Diseases, JID, University of Chicago Press, US, vol. 189, No. 2, Jan. 15, 2004, pp. 286-291.

Wang, Cy, et al., "Postexposure Imunoprophylaxis of Primary Isolates by an Antibody to HIV Receptor Complex", Proceedings of the National Academy of Sciences, National Academy of Sciences, US, vol. 96, No. 18, Aug. 1, 1999, pp. 10367-140372.

Search Report and English Translation issued in Russian application No. 2019106804, dated Mar. 25, 2021, 5 pages.

Jacobson, J.M., et al., Safety, pharmacokinetics, and antiretroviral activity of multiple doses of ibalizumab (formerly TNX-355), an anti-CD4 monoclonal antibody, in human immunodeficiency virus type 1-infected adults // Antimicrobial agents and chemotherapy.—2009.—vol. 53.—No. 2.—pp. 450-457.

Search Report and Written Opinion issued in Singapore Application No. 11201901203P, dated May 22, 2020, 9 pages.

Office Action and English Translation issued in Russian application No. 2019106804, dated Mar. 25, 2021, 7 pages.

Yarilin, A. A., Osnovy immunologii.-M.: GEOTAR—Media, 2010.—752 p. (see pp. 276-277). Original and Machine Translation.

Gorov, A. M., et al. Theoria i practika immunofermentnogo analisa.-M.: Higher School—1991.—288 p. (see pp. 33-34). Original and Machine Translation.

Loetscher, et al. "Cloning of a Human Seven-Transmembrane Domain Receptor, LESTR, That Is Highly Expressed in Leukocytes" J. of Biological Chemistry, 264:232-237 (1994).

Supplementary European Search Report issued in corresponding EP Patent Application No. 14902149, dated Apr. 17, 2018.

Office Action and Search Report (translated into English) issued in corresponding Indonesian Patent Application No. P00201605747, dated Feb. 12, 2019.

Search Report (translated into English) issued in corresponding Russian Patent Application No. 2017112967, dated Jul. 24, 2018.

First Written Opinion and Search Report issued in corresponding Singapore Patent Application No. 11201702056Y, dated Nov. 1, 2017.

Second Written Opinion and Search Report issued in corresponding Singapore Patent Application No. 11201702056Y, dated Nov. 7, 2018.

Search Report issued in corresponding Taiwan Patent Application No. 104130548, dated Jun. 1, 2016.

Adair, F., "Immunogenicity—The last hurdle for clinically successful therapeutic antibodies." BioPharm, 42-46 (2000).

Altuvia, Y., et al., "Ranking potential binding peptides to MHC molecules by a computational threading approach." J. Mol. Biol., 249(2): 244-250 (1995).

Arthos et al., "Identification of the Residues in Human CD4 Critical for the Binding of HIV." Cell, 57: 469-481 (1989).

Baltimore, D., "The Enigma of HIV Infection." Cell, 82: 175-176 (1995).

International Search Report and Written Opinion issued in corresponding International Application No. PCT/US2014/065048, dated Mar. 10, 2015, 9pp.

Phogat et al. "Inhibition of HIV-1 entry by antibodies: potential viral and cellular targets," Journal of Internal Medicine, Jun. 19, 2007, vol. 262, Issue 1, pp. 26-43.

Robinson et al., "High frequencies of antibody responses to CD4 induced epitopes in HIV infected patients started on HAART during acute infection," Human Antibodies, May 17, 2006 (May 17, 2006), vol. 14, pp. 115-121.

International Preliminary Report on Patentability (IPRP) issued in corresponding International Application No. PCT/US2014/065048, dated Nov. 29, 2016, 7pp.

Jiao, Y.M., et al., "CD4+CD25+CD127 regulatory cells play multiple roles in maintaining HIV-1 p24 production in patients on long-term treatment: HIV-1 p24-producing cells and suppression of anti-HIV immunity." Int. J. Infect. Dis., 37:42-49(2015).

Jones, T.D., et al., "Deimmunization of Monoclonal Antibodies." Methods Mol. Bio., 525: 405-423 (2009).

Kabat, E.A., "AbCheck—How it works." The Kabat database of sequences of proteins of immunological interest (website: immuno.bme.nwu.edu), dated Jan. 31, 2003.

König, R., et al., "Involvement of both major histocompatibility complex class II alpha and beta chains in CD4 function indicates a role for ordered oligomerization in T cell activation." J. Exp. Med., 182: 779-787 (1995).

Moore, J.P., et al., "Genetic subtypes, humoral immunity, and human immunodeficiency virus type 1 vaccine development." J. Virol., 75(13), 5721-5729 (2001).

Moore, J.P., "AIDS vaccines: On the trail of two trials." Nature 415: 365-366 (2002).

Morrison, S.L., et al., "Chimeric human antibody molecules: mouse antigen-binding domains with human constant region domains." PNAS, 81(21): 6851-6855 (1984).

Motto, M., et al., "Genetic manipulations of protein quality in maize grain." Field Crops Research, 45: 37-48 (1996).

Mulligan, R.C., et al., "Synthesis of rabbit beta-globin in cultured monkey kidney cells following infection with a SV40 beta-globin recombinant genome." Nature, 277(5692): 108-114 (1979).

Myszka, D.G., et al., "Energetics of the HIV gp120-CD4 binding reaction." PNAS, 97(16): 9026-9031 (2000).

Norderhaug, L., et al., "Versatile vectors for transient and stable expression of recombinant antibody molecules in mammalian cells." J. Immunol Methods, 204(1): 77-87 (1997).

Pace, C., et al., "Anti-CD4 monoclonal antibody ibalizumab exhibits exceptional breadth and potency against HIV, which adopts a unique pathway to resistance" 18th CROI—Boston, Abstract 585 (2011).

Pace, C.S., et al., "Anti-CD4 Monoclonal Antibody ibalizumab Exhibits Breadth and Potency Against HIV-1, with Natural Resistance Medicated by the loss of a V5 Glycan in Envelope." J. Aids, 62: 1-9 (2013).

Padlan, E.A., "A possible procedure for reducing the immunogenicity of antibody variable domains while preserving their ligand-binding properties." Mol. Immunol., 28(4-5): 489-498 (1991).

Page, M.J., et al., "High level expression of the humanized monoclonal antibody Campath-1H in Chinese hamster ovary cells" Boptechnology, 9(1): 64-68 (1991).

Reimann, K.A., et al., "In vivo administration of CD4-specific monoclonal antibody: Effect on provirus load in rhesus monkeys chronically infected with the simian immunodeficiency virus of macaques." AIDS Res. Hum. Retroviruses, 11 (4): 517-525 (1995).

Reimann, K.A., et al., "A humanized form of a CD4-specific monoclonal antibody exhibits decreased antigenicity and prolonged plasma half-life in rhesus monkeys while retaining its unique biological and antiviral properties." AIDS Res. Hum. Retroviruses, 13(11): 933-943 (1997).

Reiter, C., et al., "Treatment of rheumatoid arthritis with monoclonal CD4 antibody M-T151." Arthritis Rheum., 34(5): 525-536(1991).

Remington's Pharmaceutical Sciences, Mack Publishing Company, Easton, Pa., 19th Edition, pp. 1524-1532 (1995).

Rieber, E.P., et al., "Monoclonal CD4 antibodies after accidental HIV infection." Lancet, 336: 1007-1008 (1990).

Riechmann, L., et al., "Reshaping human antibodies." Nature, 332: 323-327 (1988).

Russell, D.A., "Feasibility of antibody production in plants for human therapeutic use." Curr. Top. Microbiol. Immunol., 240: 119-138(1999).

Sattentau, Q.J., et al., "Epitopes of the CD4 antigen and HIV infection." Science, 234: 1120-1123 (1986).

(56) References Cited

OTHER PUBLICATIONS

Sawyer, L.S.W., et al., "Neutralization sensitivity of human immunodeficiency virus type 1 is determined in part by the cell in which the virus is propagated." J. Virol., 68(3): 1342-1349 (1994).
Saxena, A., et al., "Advances in Therapeutic Fc Engineering—Modulation of IgG-Associated Effector Functions and Serum Half-life " Front. Immunol, 7(580): 1-11 (2016).
Sigal, A., et al., "Cell-to-Cell spread of HIV permits ongoing replication despite antiretroviral therapy." Nature, 477: 95-98 (2011).
Song, R., et al., "Strategic addition of an N-linked glycan to a monoclonal antibody improves its HIV-1-neutralizing activity." Nature Biotechnology, 31: 1047-1052 (2013).
Stiegler, G., et al., "Antiviral activity of the neutralizing antibodies 2F5 and 2G12 in asymptomatic HIV-1-infected humans: a phase I evaluation." AIDS, 16: 2019-2025 (2002).
Stott, E.J., "Anti-cell antibody in macaques." Nature, 353(6343): 393 (1991).
Takahashi, N., et al., "Structure of human immunoglobulin gamma genes: Implications for evolution of a gene family." Cell, 29: 671-679 (1982).
Tao, M.H., et al., "Studies of aglycosylated chimeric mouse-human IgG. Role of carbohydrate in the structure and effector functions mediated by the human IgG constant region." J. Immunol., 143(8): 2595-2601 (1989).
Than, S., et al., "Upregulation of human immunodeficiency virus (HIV) replication by CD4 cross-linking on peripheral blood mononuclear cells of HIV-infected adults." J. Virol, 71(8): 6230-6232 (1997).
Toma, T., et al., "Loss of Asparagine-linked glycosylation sites in variable region 5 of human immunodeficiency virus type 1 envelope is associated with resistance to CD4 antibody ibalizumab." J Virol, 85: 3872-3880 (2011).
Tomlinson, I.M., et al., "The repertoire of human germline VH sequences reveals about fifty groups of VH segments with different hypervariable loops." J. Mol. Biol., 227: 776-798 (1992).
Van De Winkel, J., "Antibody therapeutic approaches for inflammation. " in EULAR 2002 Annual European Congress of Rheumatology, Stockholm, Sweden, (2002).
Wang, C.Y., et al., "Postexposure immunoprophylaxis of primary isolates by an antibody to HIV receptor complex." PNAS, 96: 10367-10372 (1999).
Wang, C.Y., et al., "Synthetic AIDS vaccine by targeting HIV receptor." Vaccine, 21: 89-97 (2002).
Weissenhorn, W., et al., "Combinatorial Functions of Two Chimeric Antibodies Directed to Human CD4 and One Directed to the a-Chai of the Human lnterleukin-2 Receptor." Gene, 121(2): 271-278 (1992).
Wikipedia, The free encyclopedia, "HIV/AIDS", available at website: en.wikipedia.org/wiki/HIV/AIDS. Accessed Aug. 12, 2014.
Wikipedia, The free encyclopedia, "CD4", available at website: en.wikipedia.org/wiki/CD4. Accessed Aug. 10, 2016.
World Health Organization, "Global Health Observatory (GHO) HIV/AIDS", available at website:: www.who.nt/gho/hiv/en. Accessed Aug. 12, 2014.
Wright, A., et al., "Effect of glycosylation on antibody function: implications for genetic engineering." Trends Biotechnol., 15(1): 26-32 (1997).
Yuan, R., et al., "Anti-CD4: An Alternative Way to Inhibit HIV Infection." J. HIV Retrovirus., 2(1:1): 1-6 (2016).
Attanasio, R., et al., "Monoclonal Anti-CD4 as Immunoprophylactic Agents for Human Immunodeficiency Virus Infection " J Infect. Dis., 168:515-516(1993).
Briant, L., et al., "Binding of HIV virions or gp120-anti-gp120 immune complexes to HIV-1 infected quiescent peripheral blood mononuclear cells reveals latent infection." J. Immunol., 156(10):3994-4004 (1996).
Corbeau, P., et al., "Ig CDR3-Like Region of the CD4 Molecule is Involved in HIV-Induced Syncytia Formation but not in Viral Entry." J Immunol., 150:290-301 (1993).

Hasunuma, T., et al., "Regions of the CD4 Molecule not involved in Virus Binding or Syncytia Formation are Required for HIV-1 Infection of Lymphocytes." J. of Immunology, 148:1841-1846 (1992).
Jones, P.T., et al., "Replacing the Complementarily-Determining Regions in a Human Antibody with those from a Mouse." Nature, 321:522-525 (1986).
Kalyanaraman, V.S., et al., "Evidence by Peptide Mapping that the Region CD4 (81-92) is Involved in gp120/CD4 Interaction Leading of HIV Infection and HIV-Induced Syncytium Formation." J. of Immunology, 145:4072-4078 (1990).
Kennett, R.H., et al. (editors)., Appendix "Method for Production and Characterization of Monoclonal Antibodies." In Monoclonal Antibodies, Hybridomas: A New Dimension in Biological Analyses, pp. 363-419 (1980).
Wilson, M.B., et al., "Recent developments in the periodate method of conjugating horseradish peroxidase (HRPO) to antibodies." In Knapp, W., et al. (editors), Immunofluorescence and Related Staining Techniques, Elsevier/North Holland Biomedical Press, pp. 215-224 (1978).
Walfield, A.M., et al., "High-Titer Neutralization of Multiple HIV-1 Isolates by Radially Branched Immunogens" In Koff, W.C., et al. (editors), AIDS Research Reviews vol. 3, Chapter 18, New York: Marcel Dekker, Inc., pp. 345-361 [1993).
Anonymous, NIH AIDS and Research and Reference Reagent Program, Catalog No. 207 Data Sheet, (available at website: aidsreagent.org/reagentdetail.cfm?t=molecular_clones&id=116) (accessed Jan. 12, 2021) (1988).
Anonymous, ThermoFisher Scientific Product Catalog, Cat. No. 21221: Pierce™ Avidin, Fluorescein (FITC) Conjugated, Pierce Chemical Co., Rockford IL,. [available at website: thermofisher.com/order/catalog/product/21221 ?US&en#/21221?US&en) (accessed Jan. 8, 2021) (2012).
Putkonen, P., et al., "Prevention of HIV-2 and SIVsm Infection by Passive Immunization in Cynomolgus Monkeys." Nature, 352:436-438 (1991).
Rieber, E.P., et al., "The Monoclonal CD4 Antibodies M-T413 Inhibits Cellular Infection with Human mmunodeficiency Virus after Viral attachment to the Cell Membrane: An Approach to Postexposure Prophylaxis." Proc. Nat'L Acad. Sci. U.S.A., 89:10792-10796 (1992).
Rowe, P.M., "A Cofactor for HIV-1 Entry into Cells is Identified." The Lancet Science and Medicine, 347:1395 (1996).
Sattentau, Q.J., et al., "Structure Analysis of the Human Immunodeficiency Virus-Binding Domain of CD4." J. Exp. Vied., 170:1319-1334 (1989).
Smith, S.D., et al., "Monoclonal Antibody and Enzymatic Profiles of Human Malignant T-Lymphoid Cells and Derived Dell Lines." Cancer Research, 44:5657-5660 (1984).
Wang, J., et al., "Atomic Structure of a Fragment of Human CD4 Containing Two Immunoglobulin-Like Domains." Nature, 348:411-418 (1990).
Watson, S., et al. (editors), "Chemokines" in The G-Protein Linked Receptor Facts Book, Academic Press, pp. 83-88 (1994).
Wrin, T., et al., "Adaptation to Persistent Growth in the H9 Cell Line Renders a Primary Isolate of Human mmunodeficiency Virus Type 1 Sensitive to neutralization by Vaccine Sera" J. of Virology, 69(1):39-48 (1995).
Bebbington, C.R., et al., "High-level expression of a recombinant antibody from myeloma cells using a glutamine synthetase gene as an amplifiable selectable marker." Biotechnology, 10(2): 169-175 (1992).
Belshe, R.B., et al., "Neutralizing antibodies to HIV-1 in seronegative volunteers immunized with recombinant gp120 from the MN strain of HIV-1." JAMA, 272(6): 475-480 (1994).
Benkirane, M., et al., "Functional epitope analysis of the human CD4 molecule: antibodies that inhibit human mmunodeficiency virus type 1 gene expression bind to the immunoglobulin CDR3-like region of CD4." Journal of Virology, 69(11): 6898-6903 (1995).
Briant, L., et al., "HIV-1 Reactivation in resting peripheral blood mononuclear cells of infected Adults upon in vitro CD4 cross-linking by ligands of the CDR2-loop in extracellular domain 1." J AIDS. 21: 9-19 (1999).

(56) References Cited

OTHER PUBLICATIONS

Burkly, L.C., et al., "Inhibition of HIV infection by a novel CD4 domain 2-specific monoclonal antibody. Dissecting the basis for its inhibitory effect on HIV-induced cell fusion." J. Immunol., 149: 1779-87 (1992).
Burton, D.R., et al., "Effective Neutralization of Primary Isolates of HIV-1 by a Recombinant Human Monoclonal Antibody." Science, 266: 1024-1027 (1994).
Celada, F., et al., "Antibody raised against soluble CD4-rgp120 complex recognizes the CD4 moiety and blocks membrane fusion without inhibiting CD4-gp120 binding." J. Exp. Med., 172(4): 1143-1150 (1990).
Cheng-Mayer, C., et al., "Biologic features of HIV-1 that correlate with virulence in the host." Science, 240: 80-82 (1988).
Clinical Trials Update. Genetic Engineering News, 21, 3 (2001).
Clinicaltrials.gov—"Study to Evaluate Safety and Pharmacokinetics of UB-421 Antibody in HIV-1 Infected Adults." dated Jul. 11, 2011 (available at website: clinicaltrials.gov/ct2/show/NCT01140126).
Co, M.S., et al., "Humanized antibodies for antiviral therapy." PNAS, 88: 2869-2873 (1991).
Coloma, M.J., et al., " The role of carbohydrate in the assembly and function of polymeric IgG." Mol Immunol., 37(17): 1081-1090(2000).
Cox, J.P.L., et al., "A directory of human germ-line Vk segments reveals a strong bias in their usage." Eur. J. Immunol., 24(4): 827-836 (1994).
Daar, E.S., et al., "High concentrations of recombinant soluble CD4 are required to neutralize primary human immunodeficiency virus type 1 isolates." PNAS, 87(17): 6574-6578 (1990).
Dall'Acqua, W.F., et al., "Properties of human IgG1s engineered for enhanced binding to the neonatal Fc receptor (FcRn)." The Journal of Biological Chemistry, 281(33): 23514-23524 (2006).
Deeks, S.G., et al., "International AIDS Society global scientific strategy: towards an HIV cure 2016." Nature Medicine, 22: 839-850 (2016).
Desrosiers, R.C., et al., "Vaccine protection against simian immunodeficiency virus infection." PNAS, 86: 6353-6357 (1989).
Dimitrov, D.S. "Fusin—a place for HIV-1 and T4 Cells to Meet." Nature Medicine, 2: 640-641 (1996).
Doitsh, G., et al., "Cell Death by pyroptosis derives CD4 T-cell depletion in HIV infection." Nature, 505: 509-514 (2014).
Doms, R.W., et al., "The plasma membrane as a combat zone in the HIV battlefield." Genes Dev., 14: 2677-2688 (2000).
Donahue, R.E. et al., "Helper Virus Induced T Cell Lymphoma in Nonhuman Primates After Retroviral Mediated Gene Transfer." J. of Experimental Medicine, 176(4): 1125-1135 (1992).
Eloit, M., "Risks of virus transmission associated with animal sera or substitutes and methods of control." Dev Biol Stand, 99: 9-16 (1999).
Emini, E.A., et al., "Antibody-Mediated In Vitro Neutralization of Human Immunodeficiency Virus Type 1 Abolishes Infectivity for Chimpanzees." J. Virol., 64: 3674-3678 (1990).
Feng, Y., et al., "HIV-1 Entry Cofactor: Functional cDNA Cloning of a Seven-Transmembrane, G Protein-Coupled Receptor." Science, 272: 873-877 (1996).
Gardner, M., et al., "Passive immunization of rhesus macaques against SIV infection and disease." AIDS Res Hum Retroviruses, 11(7): 843-854 (1995).
Gutin, S., "Perinatal Tranmission of HIV is Preventable." CAPS/Community Health Systems—UCSF School of Nursing, Fact Sheet 34ER (2015) (available at website: prevention.ucsf.edu/sites/prevention.ucsf.edu/files/MTCT-Revised-Sept-2015.pdf).
Hanson, C.V., et al., "Application of a rapid microplaque assay for determination of human immunodeficiency virus neutralizing titers." J. Clin. Microbiol., 28(9): 2030-2034 (1990).
Hanson, C.V., "Measuring vaccine-induced HIV neutralization: Report of a workshop." AIDS Res Hum Retroviruses, 10(6), 645-648 (1994).
Hieter, P.A., et al., "Cloned human and mouse kappa immunoglobulin constant and J region genes conserve homology in functional segments " Cell, 22(1 Pt 1), 197-207 (1980).
Hieter, P.A., et al., "Evolution of human immunoglobulin kappa J region genes." J. Biol. Chem., 257(3): 1516-1522 (1982).
Ho, D.D., et al., "Conformational Epitope on gp120 Important in CD4 Binding and Human Immunodeficiency Virus Type 1 Neutralization Identified by a Human Monoclonal Antibody" J. of Virology, 65: 489-493 (1991).
Hofmann-Lehmann, R., et al., "Postnatal passive immunization of neonatal macaques with a triple combination of human monoclonal antibodies against oral simian-human immunodeficiency virus challenge." J. Virol., 75(16), 7470-7480 (2001).
Hunt, P.W., et al., "A low T regulatory Cell Response May Contribute to Both Viral Control and Generalized Immune Activation in HIV Controllers" PLoS One, 6: e15924 (2011).
Jacobson, J.M., et al., "Safety, Pharmacokinetics, and Antiretroviral Activity of Multiple Doses of Ibalizumab (formerly TNX-355), an Anti-CD4 Monoclonal Antibody, in Human Immunodeficiency Virus Type-1-Infected Adults." Antimicrob. Agents Chemother., 53: 450457 (2009).
Jameson, B.D., et al., "Location and chemical synthesis of a binding site for HIV-1 on the CD4 protein." Science, 240: 1335-1339 (1988).
Jeffrey, A.M., et al., "A model based analysis of anti-CD4 therapy as adjuvant to HAART interruption." IFAC Proceedings volumes, 38,(1): 131-136 (2005).
Keefer, M.C., et al., "Studies of high doses of a human immunodeficiency virus type 1 recombinant glycoprotein 160 candidate vaccine in HIV type 1-seronegative humans." AIDS Res Hum Retroviruses, 10(12): 1713-1723 (1994).
Kim, S.J., et al., "Characterization of chimeric antibody producing CHO cells in the course of dihydrofolate reductase-mediated gene amplification and their stability in the absence of selective pressure." Biotechnol. Bioeng., 58(1): 73-84 (1998).
Kuritzkes, D.R., et al., "Antiretroviral activity of the anti-CD4 monoclonal antibody TNX-355 in patients infected with HIV type I" J. Infect Dis., 189: 286-291 (2004).
Leatherbarrow, R.J., et al., "Effector functions of a monoclonal aglycosylated mouse IgG2a: binding and activation of complement CI and interaction with human monocyte Fc receptor." Mol. Immunol. 22(4): 407-415 (1985).
Li, Y., et al., "Three-dimensional structures of the free and antigen-bound Fab from monoclonal antilysozyme antibody HyHEL-63(,)." Biochemistry, 39: 6296-6309 (2000).
Lu, L., et al., "A bivalent recombinant protein inactivates HIV-1 by targeting the gp41 prehairpin fusion intermediate Induced by CD4 D1D2 domains, 1." Retrovirology, 104(9): 1-14 (2012).
Ma, J.K-C., et al., "Assembly of monoclonal antibodies with IgG1 and IgA heavy chain domains in transgenic tobacco plants." Eur J. Immunol., 24(1): 131-138 (1994).
Mascola, J. R., et al., "Human immunodeficiency virus type 1 neutralizing antibody serotyping using serum pools and an infectivity reduction assay." AIDS Res. Hum. Retroviruses, 12(14): 1319-1328 (1996).
Mascola, J.R., et al., "Immunization with envelope subunit vaccine products elicits neutralizing antibodies against aboratory-adapted but not primary isolates of human immunodeficiency virus type 1" J. Infect. Dis., 173(2): 340-348 (1996).
Meloen, R.H., et al., "The Use of Peptides to Reconstruct Conformational Determinants; a Brief Review." Ann. Biol. Clin , 49: 231-242 (1991).
Mizushima, S., et al., "pEF-BOS, a powerful mammalian expression vector." Nucleic Acids Res., 18(17), 5322 (1990).
Monossi, M., et al., "Improved analysis of promotor activity in biolistically transformed plant cells." BioTechniques, 28(1): 54-58 (2000).
Monroe, K.M., et al., "IFI16 DNA sensor is required for death of lymphoid CD4 T cells abortively infected with HIV." Science, 343(6169): 428-32 (2014), Epub (2013).
Moore, J.P. AIDS vaccines: On the trail of two trials. Nature 2002, 415, 365-366.

(56) References Cited

OTHER PUBLICATIONS

Menossi, M. et al., "Improved analysis of promotor activity in biolistically transformed plant cells." BioTechniques, 28(1), 54-58 (2000).
Moore, J.P., et al., "A monoclonal antibody to CD4 domain 2 blocks soluble CD4-induced conformational changes in the envelope glycoproteins of human immunodeficiency virus type 1 (HIV-1) and HIV-1 infection of CD4+ cells." J. VVirol., 66(8):4784-93 (1992).
Yang, H-C, et al., "Isolation of a cellular factor that can reactivate latent HIV-1 without T cell activation." Proc Natl. Acad. Sci. U.S.A., 106(15):16321-6 (2009).
Arthur, L.O., et al., "Cellular Proteins Bound to Immunodeficiency Viruses: Implications for Pathogenesis and Vaccines" Science 258:1935-1938 (1991).
Brady, R.L., et al., "Crystal Structure of Domains 3 and 4 of Rat CD4: Relation to the NH.sub.2-Terminal Domains" Science 260:979-983 (1993).
Camerini, D., et al., "A CD4 Domain Important for HIV-Mediated Syncytium Formation Lies outside the Virus Binding Site" Cell 60:747-754 (1990).
Clayton, L.K., et al., "Substitution of Murine for Human CD4 Residues Identifies Amino Acids Critical for HIV-gp120 Binding" Nature 335:363-366 (1988).
Cocchi, F., et al., "Identification of RANTES, MIP-1 Alpha, and MIP-1 Beta as the Major HIV-suppressive Factors Produced by CD8+ T Cells" Science 270:1811-1815 (1995).
Dalgleish, A.G., et al., "The CD4 (T4) Antigen is an Essential Component of the Receptor for the AIDS Retrovirus" Nature 312:763-766 (1984).
Davis, S.J., et al., "Antibody and HIV-1 gp120 Recognition of CD4 Undermines the Concept of Mimicry between Antibodies and Receptors" Nature 358:76-79 (1992).
Emini, E.A., et al., "Prevention of HIV-1 Infection in Chimpanzees by gp120 V3 Domain-Specific Monoclonal Antibody" Nature 355:728-730 (1992).
Gauduin, M.C., et al., "Pre-and Postexposure Protection against Human Immunodeficiency Virus Type 1 Infection Mediated by a Monoclonal Antibody" J. of Infectious Diseases 1711203-1209 (1995).
Ho, D.D., et al., "Quantitation of Human Immunodeficiency Virus Type 1 in the Blood of Infected Persons" The New England Journal of Medicine 321:1621-1625 (1989).
Kohler, G., et al., "Continuous Cultures of Fused Cells Secreting Antibody of Predefined Specificity" Nature 256:495-497 (1975).
Landau, N.R., et al., "The Envelope Glycoprotein of the Human Immunodeficiency Virus Binds to the Immunoglobulin-Like Domain of CD4" Nature 334:159-162 (1988).
Lewis, M.G., et al., "Passively Transferred Antibodies Directed Against Conserved Regions of SIV Envelope Protect Macaques from SIV Infection" Vaccine 11:1347-1355 (1993).
Montefiori, D.C., et al., "Complement Control Proteins, CD46, CD55, and CD59 as Common Surface Constituents of Human and Simian Immunodeficiency Viruses and Possible Targets for Vaccine Protection" Virology 205:82-92 (1994).
Montefiori, D.C., et al., "New Insights into the Role of Host Cell Proteins in Antiviral Vaccine Protection" AIDS Research and Human Retroviruses 11:1429-1431 (1995).
Murphey-Corb, M., et al., "A Formalin-Inactivated Whole SIV Vaccine Confers Protection in Macaques" Science 246:1293-1297 (1989).
Peterson, A., et al., "Genetic Analysis of Monoclonal Antibody and HIV Binding Sites on the Human Lymphocyte Antigen CD4" Cell 54:65-72 (1988).
Prince, A.M., et al., "Prevention of HIV Infection by Passive Immunization with HIV Immunoglobulin" AIDS Research and Human Retroviruses 7:971-973 (1991).
Ryu, S.E., et al., "Crystal Structure of an HIV-Binding Recombinant Fragment of Human CD4" Nature 348:419-426 (1990).
Safrit, J.T., et al., "hu-PBL-SCID Mice can be Protected from HIV-1 Infection by Passive Transfer of Monoclonal Antibody to the Principal Neutralizing Determinant of Envelope gp120" AIDS 7:15-21 (1993).
Sastry, L., et al., "Cloning of the Immunological Repertoire in *Escherichia Coli* for Generation of Monoclonal Catalytic Antibodies: Construction of a Heavy Chain Variable Region-Specific cDNA Library" Proc. Nat'l. Acad. Sci. U.S.A. 86:5728-5732 (1989).
Wang, C.Y., et al., "Stimulation and Expansion of a Human T-Cell Subpopulation by a Monoclonal Antibody to T-Cell Receptor Molecule" Hybridoma 5:179-190 (1986).
Wang, et al., "Long-Term High-Titer Neutralizing Activity Induced by Octameric Synthetic HIV-1 Antigen" Science 254:285-288 (1991).
White-Scharf, M.E., et al. "Broadly Neutralizing Monoclonal Antibodies to the V3 Region of HIV-1 Can Be Elicited by Peptide Immunization" Virology 192:197-206 (1993).

* cited by examiner

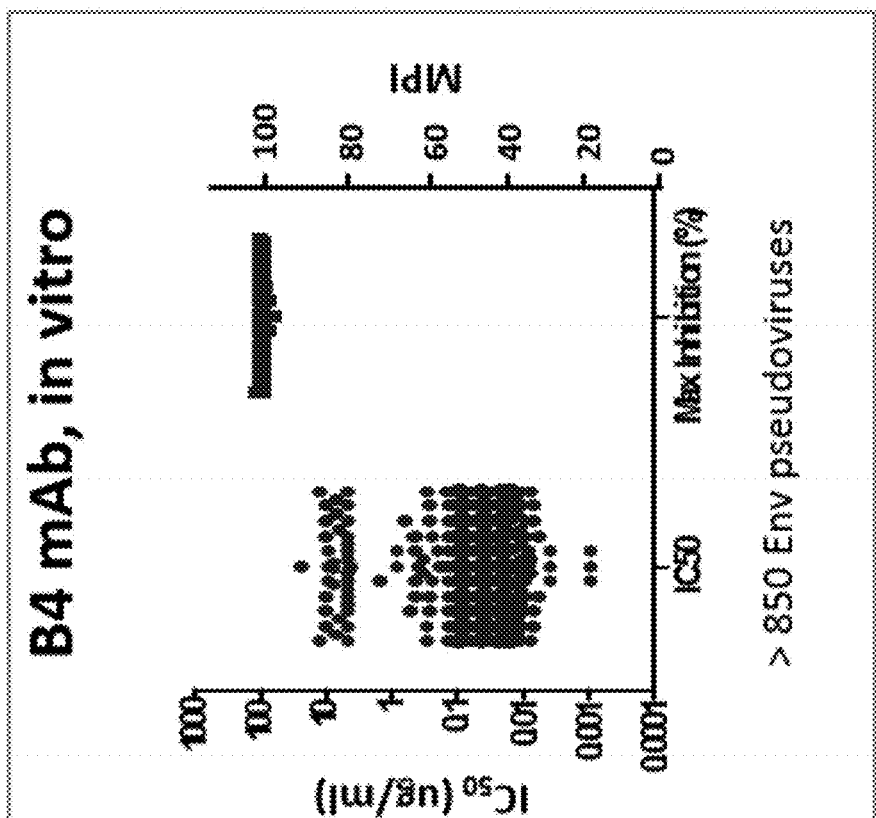
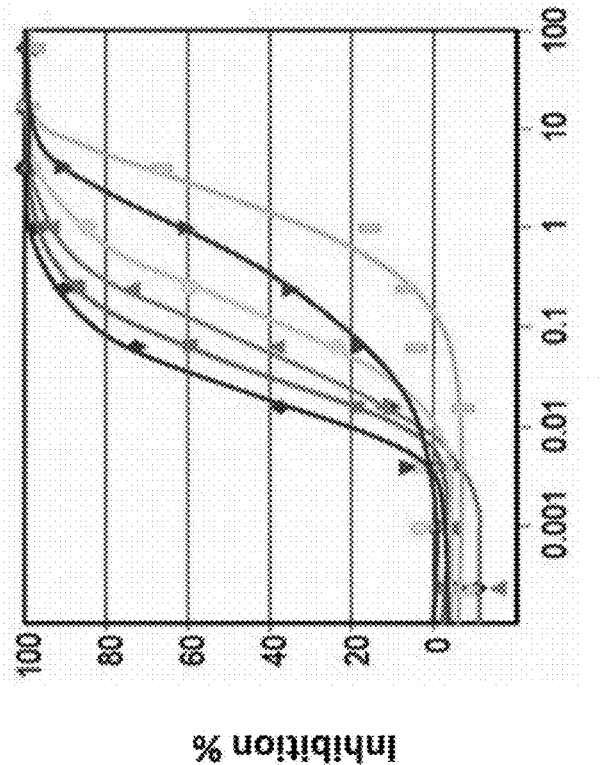
Figure 1A
Figure 1B

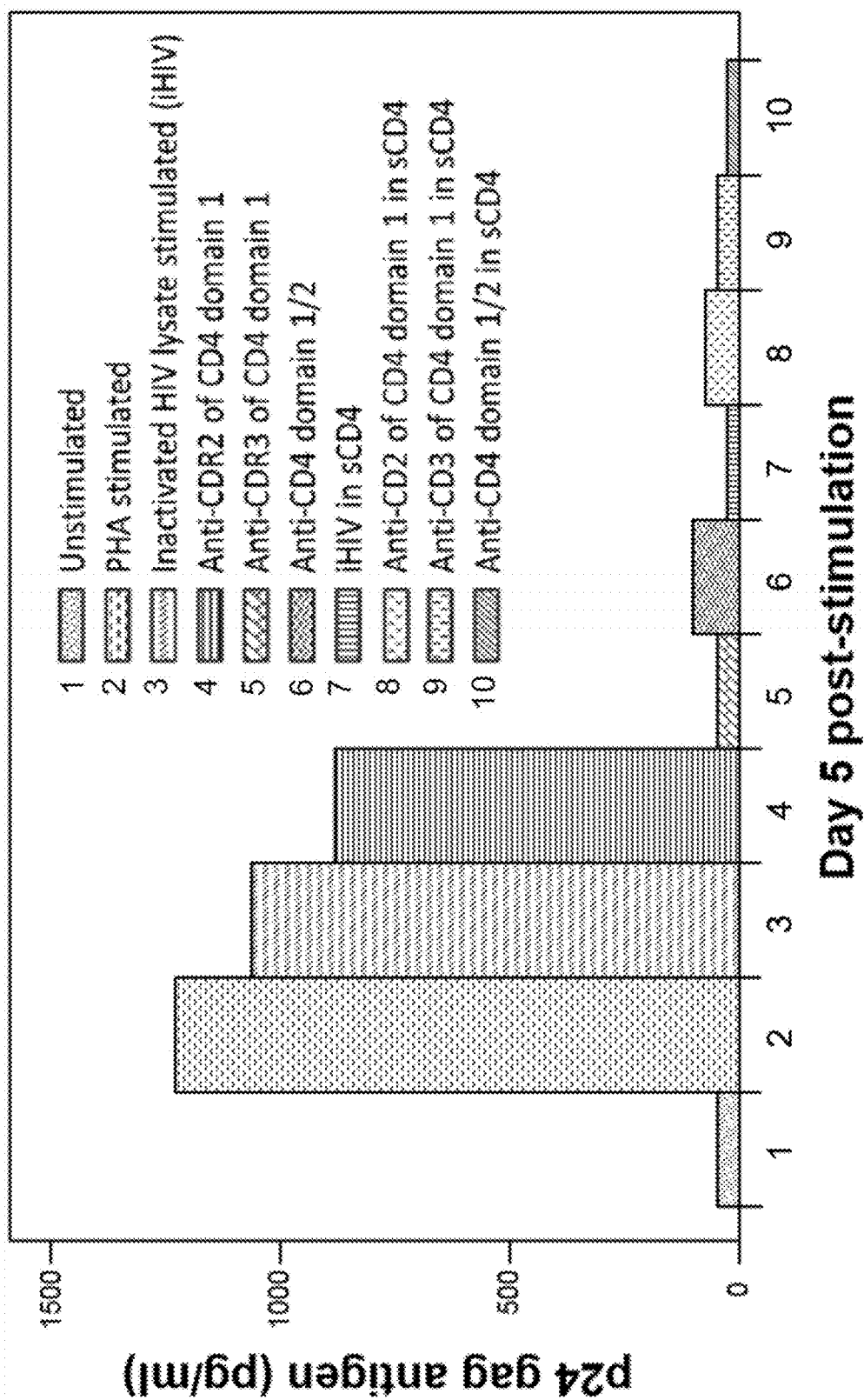

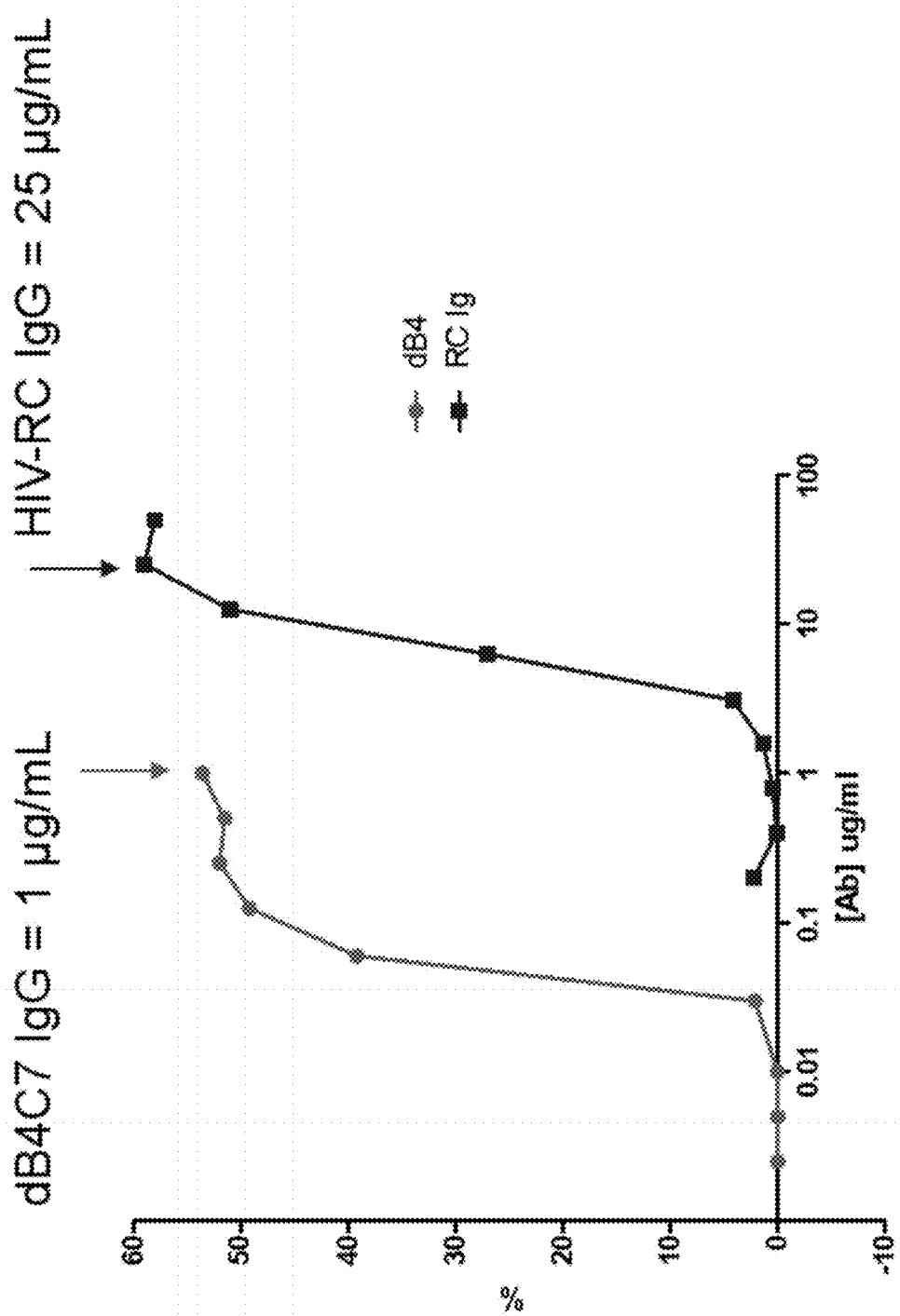

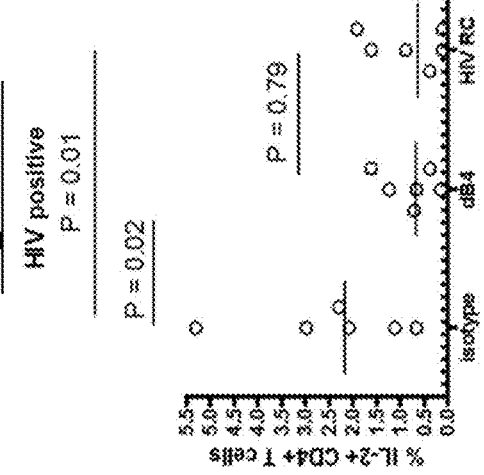
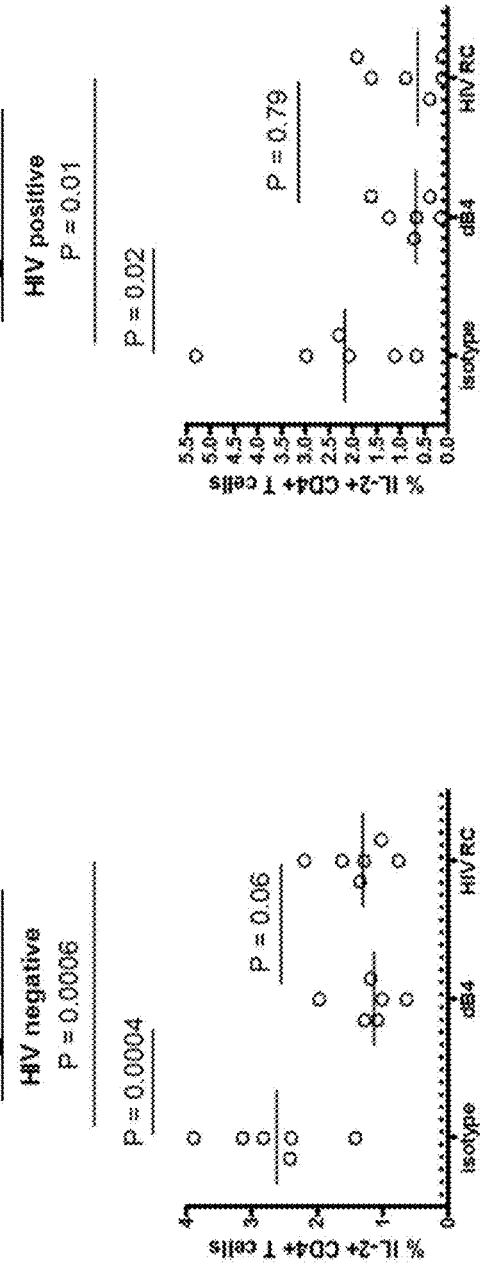
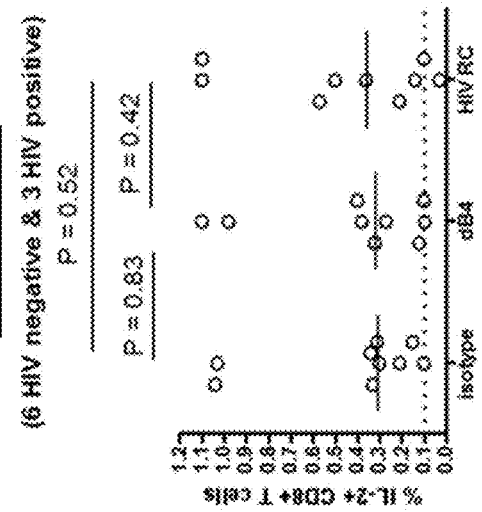

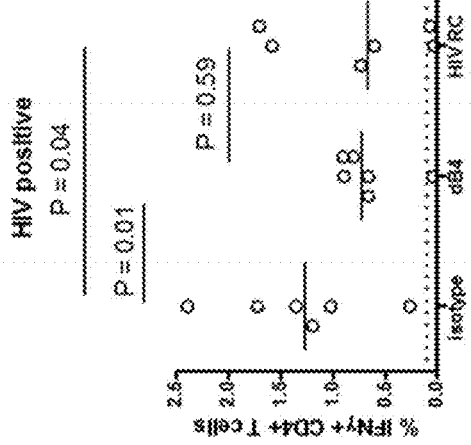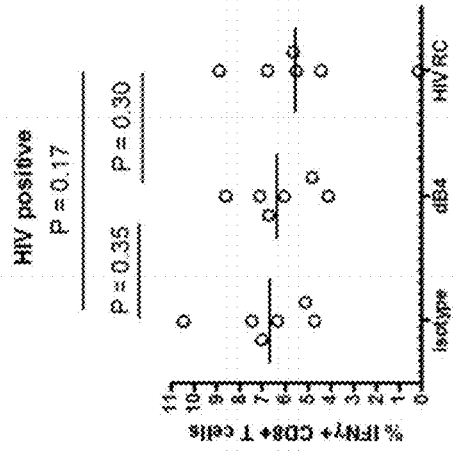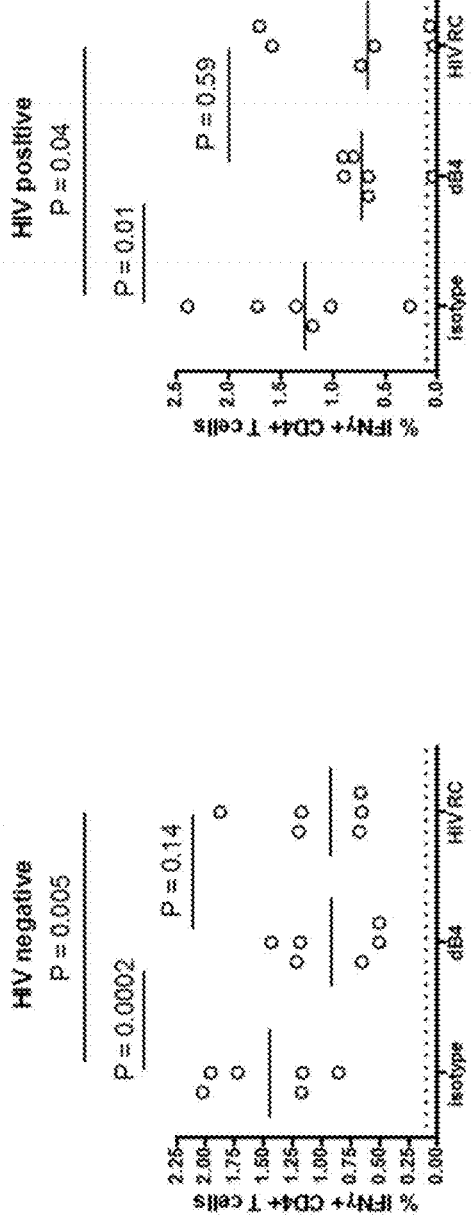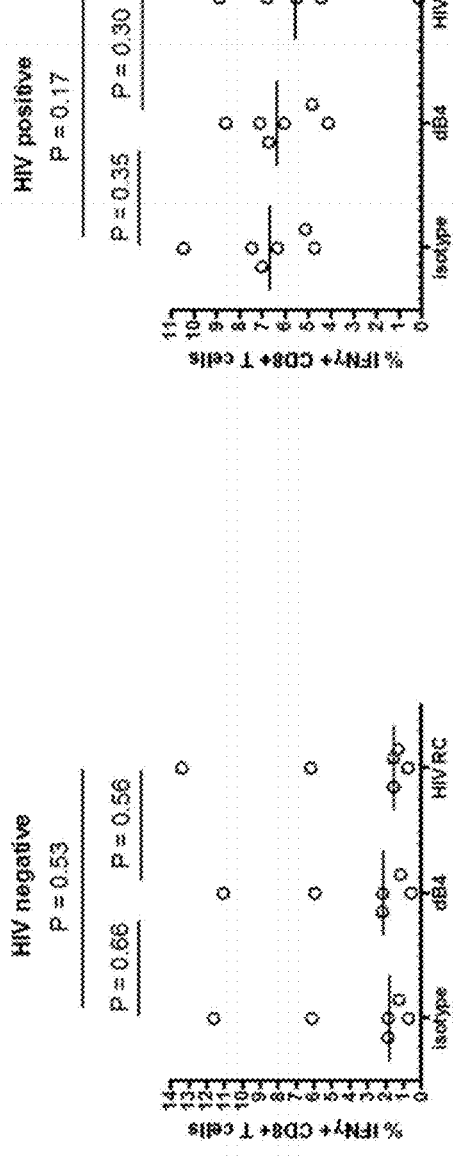

Figure 8A
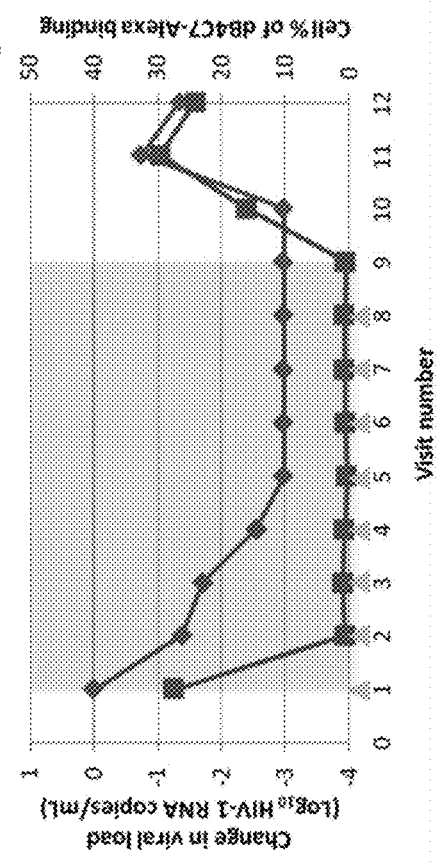
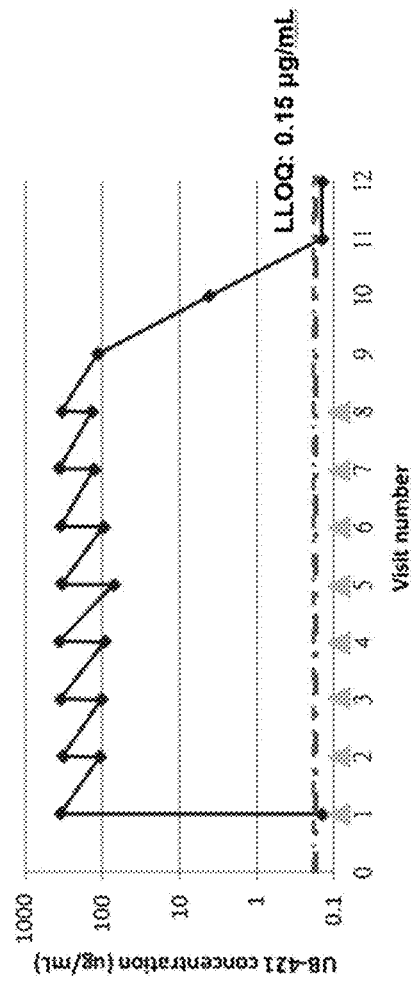

Figure 8B
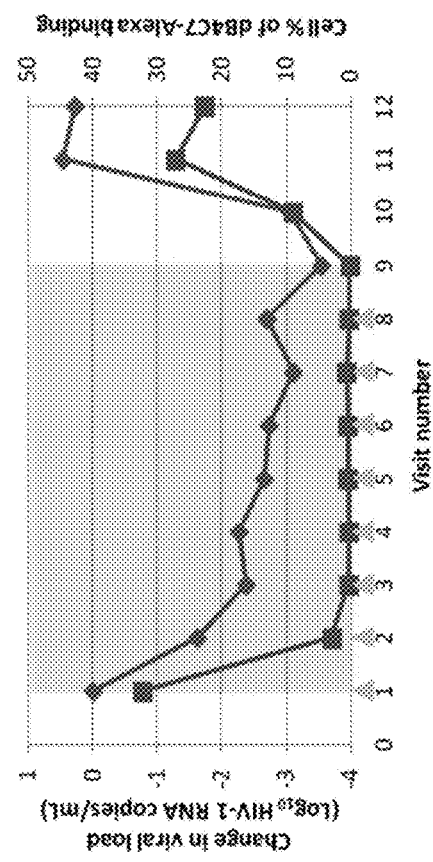
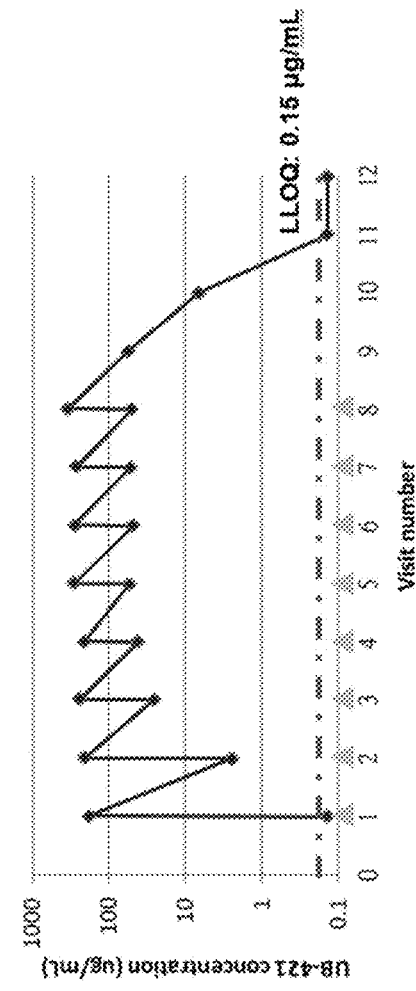

Figure 8C
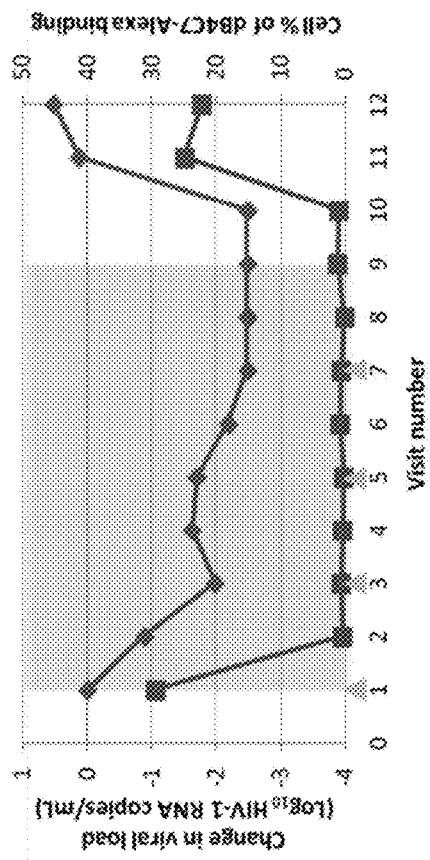
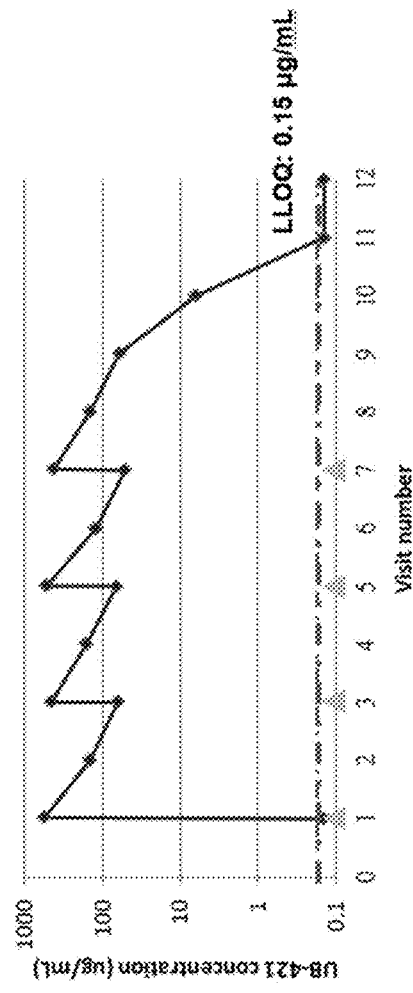

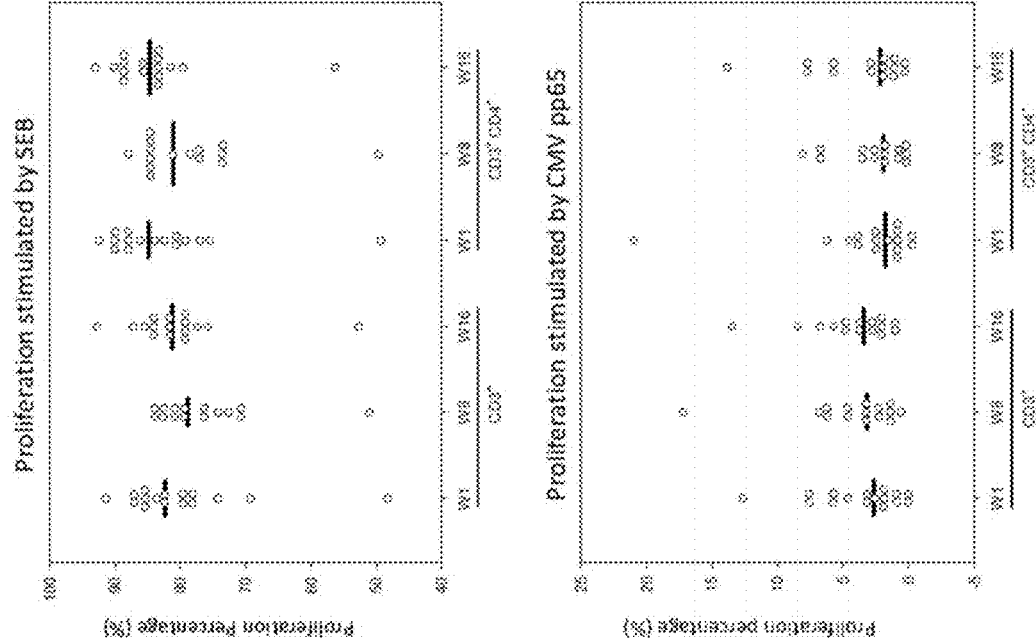
Figure 9A
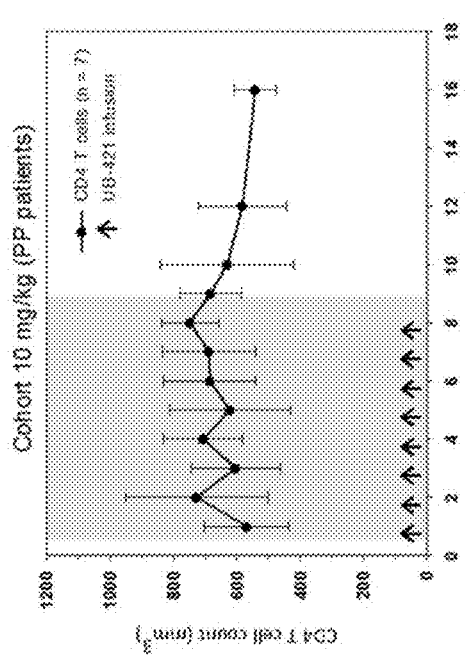
Figure 9B
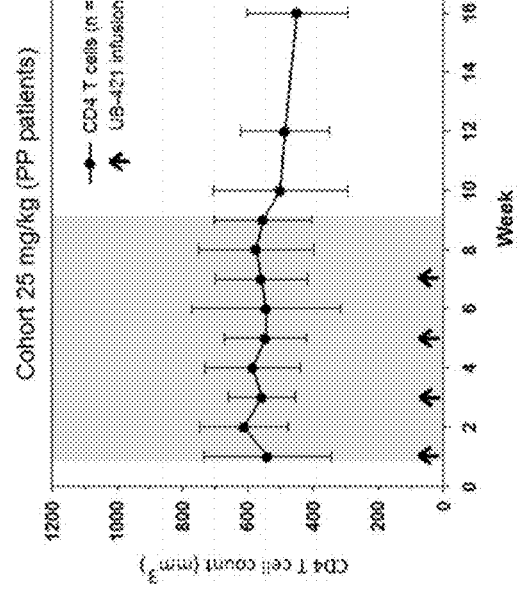

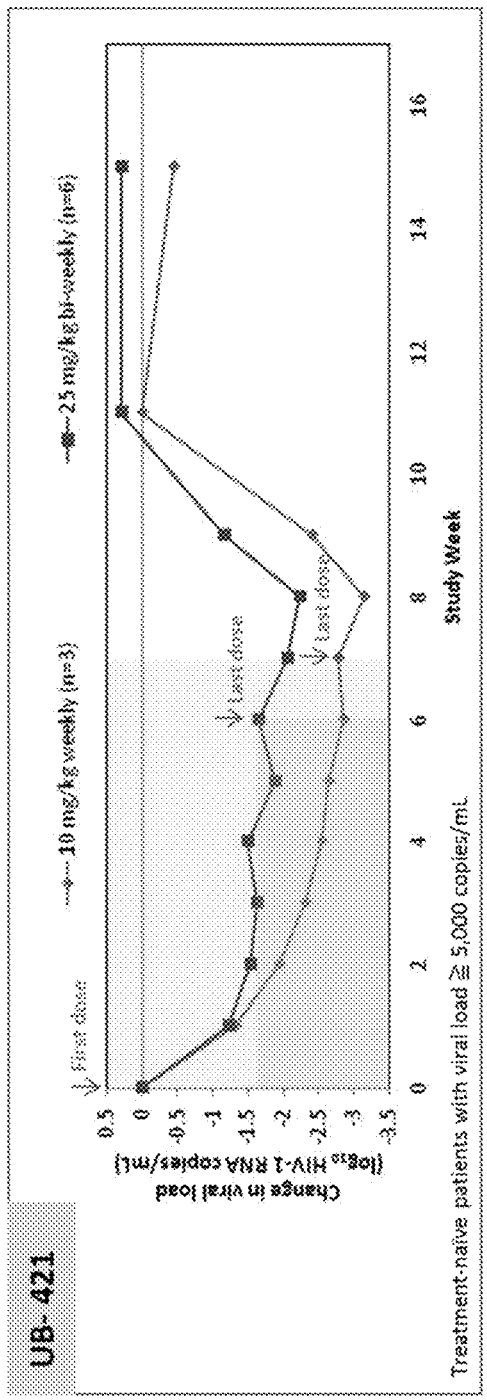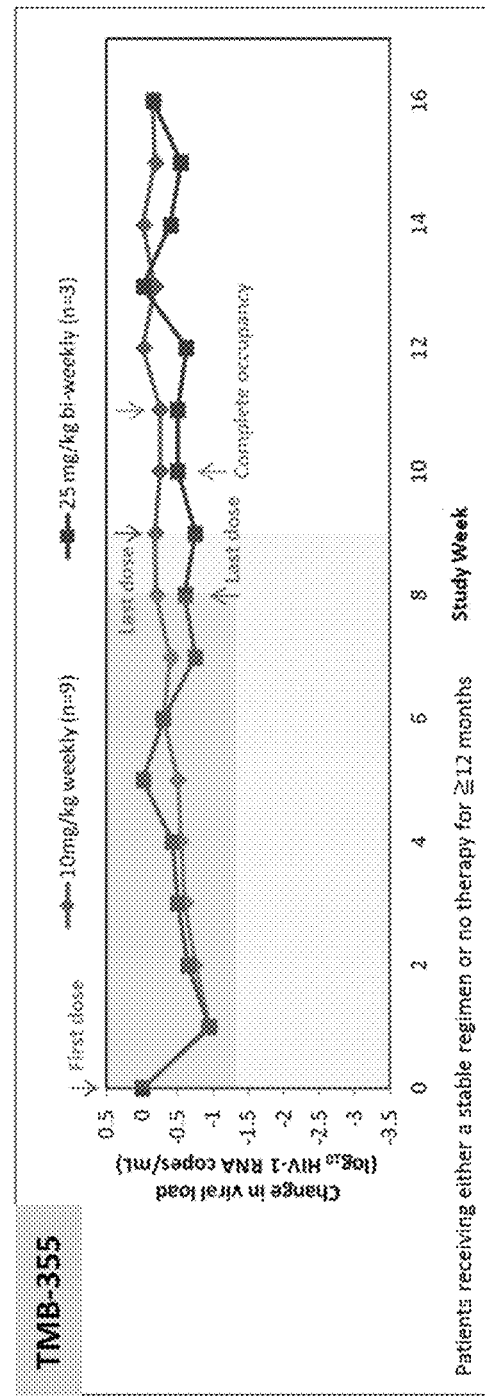

Figure 12
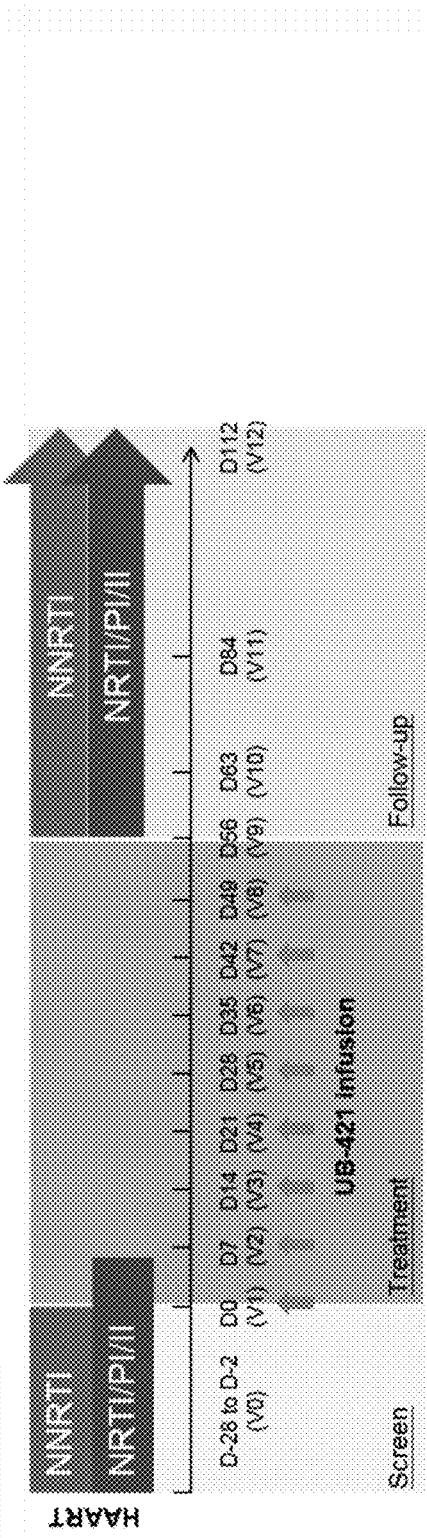
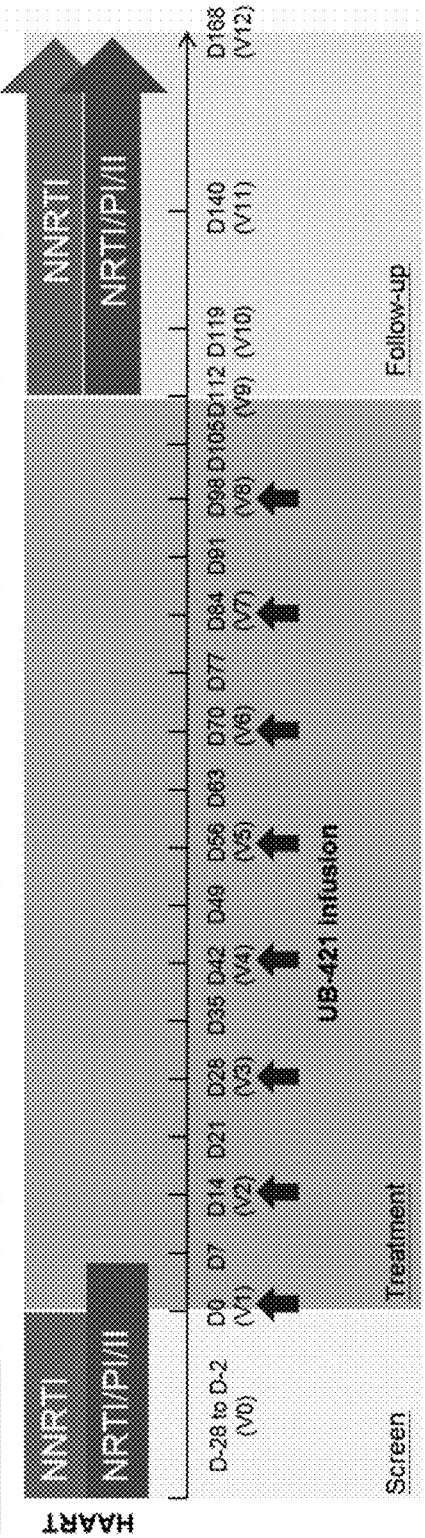

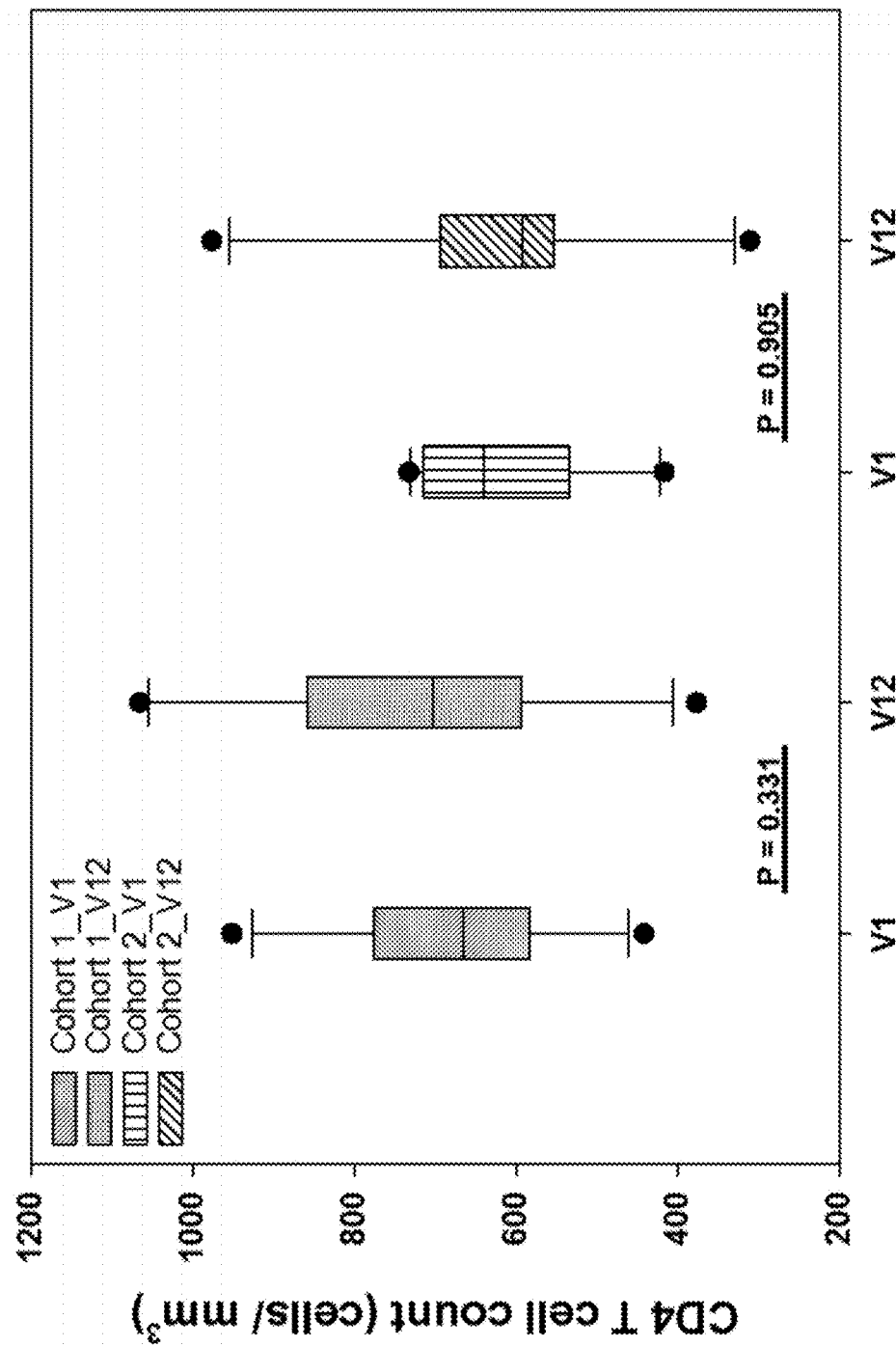

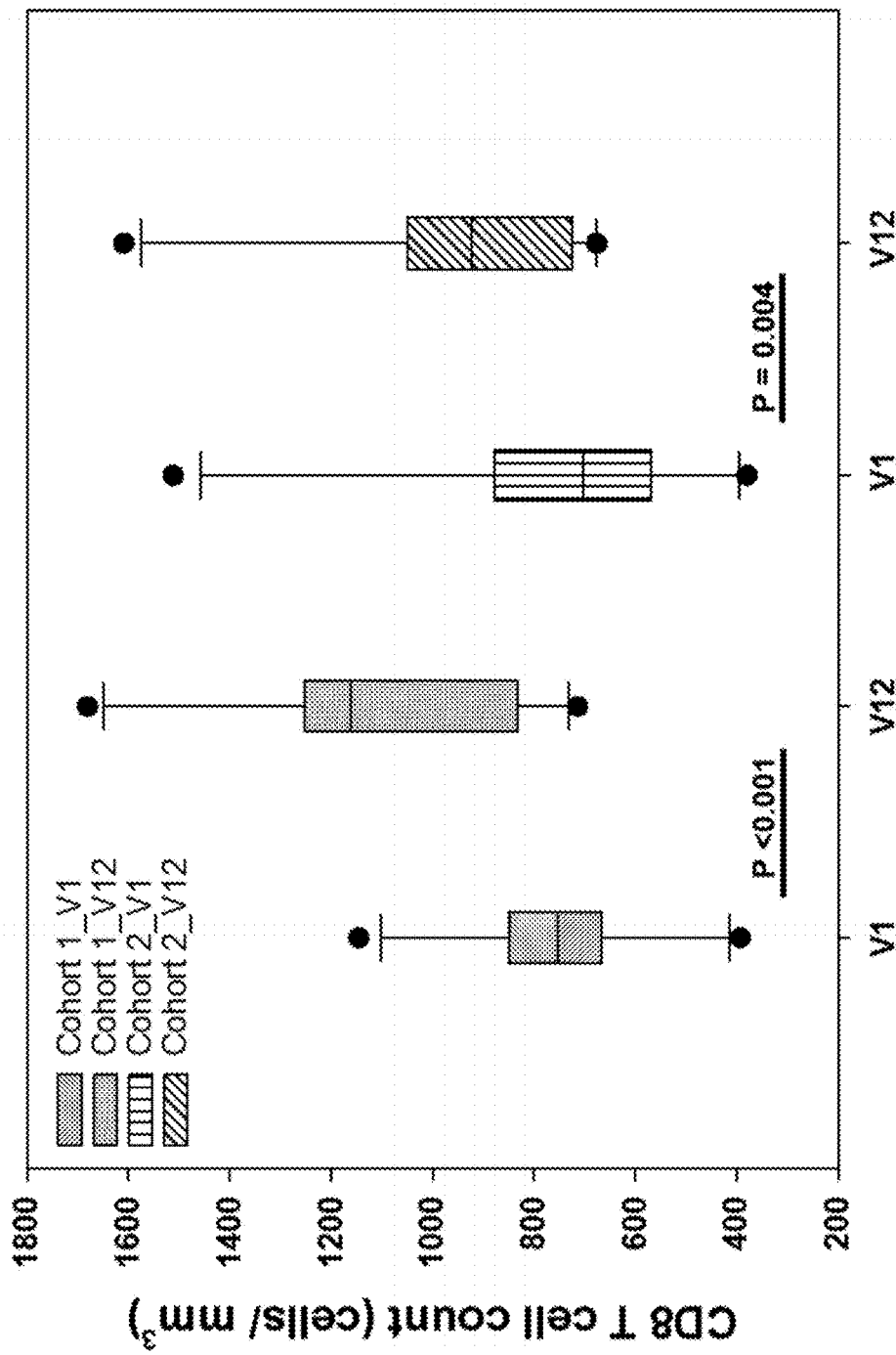

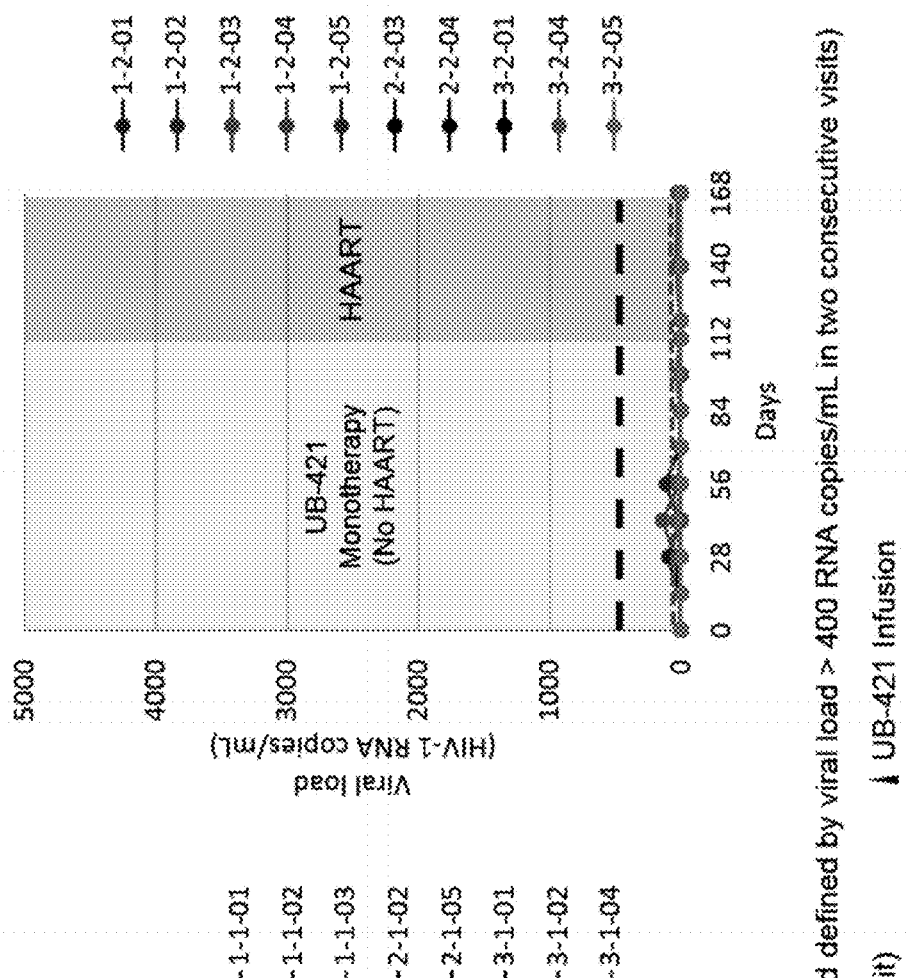
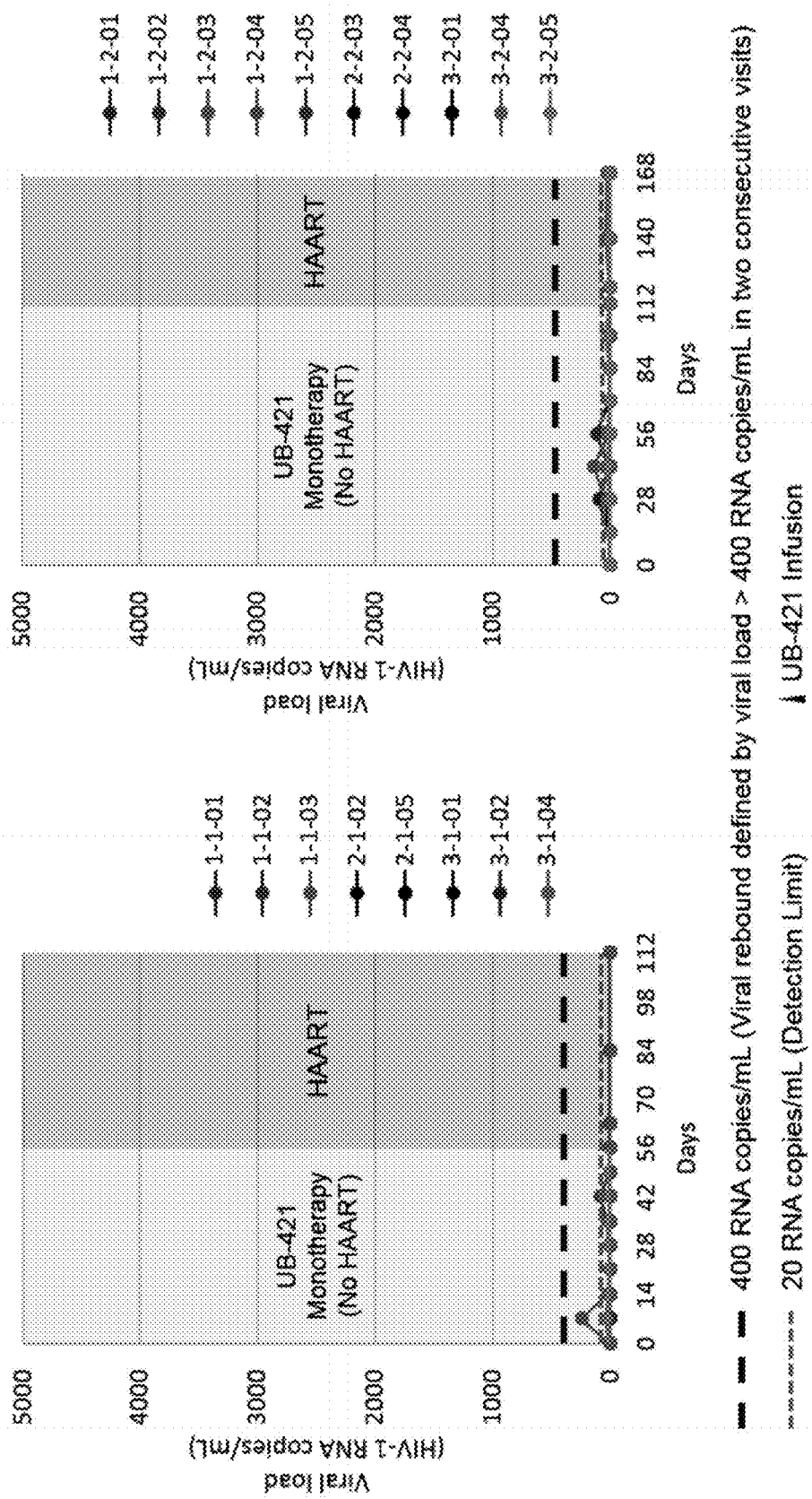

Figure 20

Monotherapy of HIV Drugs for Maintenance of Viral Suppression

End parameter: % of viral suppression
Pass = viral load <400
Fail = viral load of ≥400 for 2 consecutive weeks

| Weeks | (1) Historic data of HIV drugs on the market | (2) VRC01 | (3) Pro140 | (4) UB-421 |
|---|---|---|---|---|
| 4 | 50% | 70% | 98% | 100% |
| 8 | 0% | 10% | 82% | 100% |
| 12 | 0% | 0% | 75% | 100% |
| 16 | 0% | NA | NA | 100% |

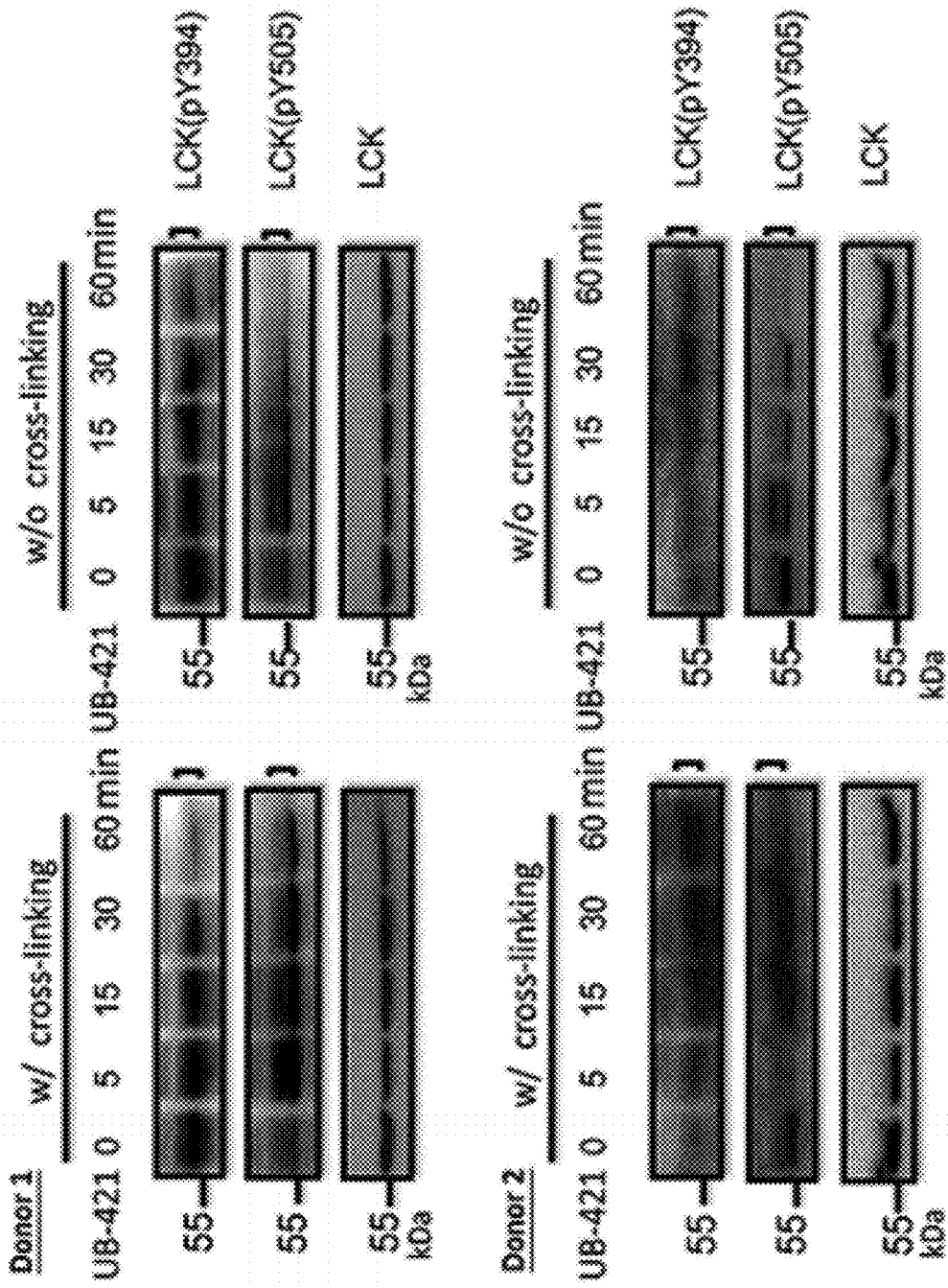

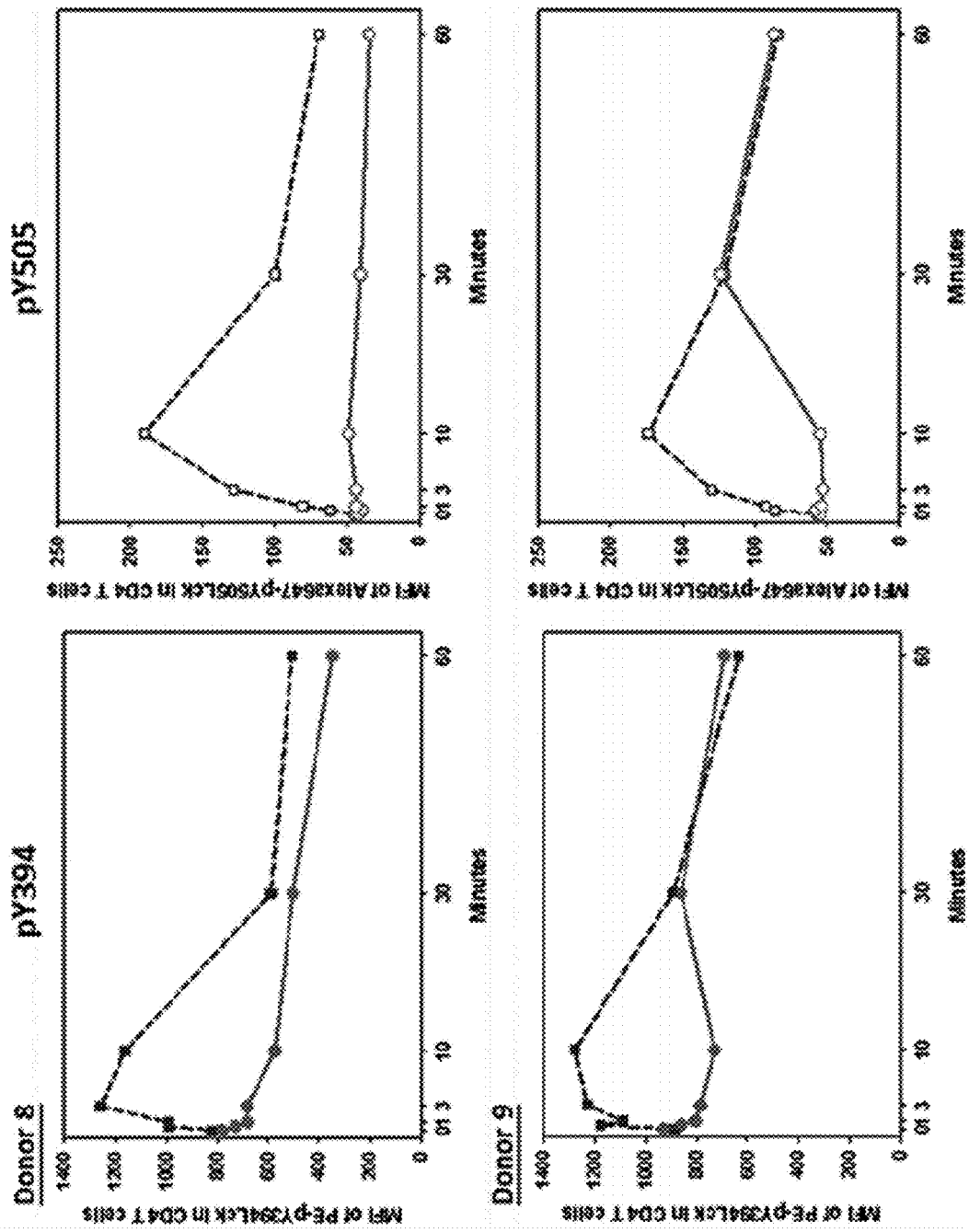

TREATMENT AND SUSTAINED VIROLOGIC REMISSION OF HIV INFECTION BY ANTIBODIES TO CD4 IN HAART STABILIZED PATIENTS

This application is a national phase entry under 35 U.S.C. § 371 of International Application Number PCT/US2017/046668, filed Aug. 13, 2016, entitled "TREATMENT AND SUSTAINED VIROLOGIC REMISSION OF HIV INFECTION BY ANTIBODIES TO CD4 IN HAART STABILIZED PATIENTS", which claims the benefit of U.S. Provisional Application Ser. No. 62/374,752, filed Aug. 13, 2016, the entire contents of these prior applications are hereby incorporated by reference as if fully set forth herein.

FIELD OF THE INVENTION

The invention relates to antibodies directed against CD4 for treatment and sustained virologic remission of HIV infection in Highly Active Antiretroviral Therapy (HAART) stabilized patients as a replacement for HAART.

BACKGROUND OF THE INVENTION

The HIV/AIDS pandemic represents the most important global health challenge in modern history. Combination antiretroviral therapy (cART), when used optimally, can effectively control HIV replication, prevent the development of AIDS, prolong life and reduce the risk of transmission. Despite this remarkable success, the current antiretroviral therapy has its limitations because it is not curative and infected patients must continue treatment indefinitely. Given the challenges in providing lifelong therapy to a global population of more than 35 million people living with HIV, there is intense interest in developing a cure for HIV infection. A recent review article "Global Scientific Strategy: Towards an HIV Cure 2016" describes the crucial knowledge gaps and research questions in the field and is referenced as the background for the state of the art of of this field (Deeks, S. G., et al., 2016). The information disclosed in this review article is incorporated herein by reference in its entirety.

The ideal outcome in treating any viral infection is the complete eradication of all replication-competent virion within the treated patient, i.e., a cure. Such a sterilizing cure can be challenging to achieve and/or difficult to prove for certain viral infections, such as HIV. A more pragmatic, yet clinically successful, treatment outcome for complicated viral infections would be the achievement of a sustained, long-term virologic remission. Remission is likely to be a necessary precursor for the development of a true HIV cure, and is increasingly utilized in the field to indicate the goal of long-term undetectable viremia for an as-yet-undefined period (probably of several years) in the absence of ART.

In view of the current state of the art, there is a need for products and treatment methods that can achieve a sustained, long-term virologic remission of HIV as a replacement for HAART.

REFERENCES

1. Deek, S. G., Lewin, S. R., Ross, A. L. et al. "International AIDS Society global scientific strategy: towards an HIV cure 2016." Nature Medicine. 2016. 22:839-850.
2. Hunt, P. W., LAnday, A. L., Sinclair, E., et al. A low T regulartory Cell Response May Contribute to Both Viral Control and Generalized Immune Activation in HIV Controllers. PLoS One. 2011. 6: e15924.
3. Yuan R, Qi J, Zhang Z, et al. Anti-CD4: An Alternative Way to Inhibit HIV Infection. J HIV Retrovirus. 2016, 2:1.
4. Celada F, Cambiaggi C, Maccari J, Burastero S, Gregory T, Patzer E, Porter J, McDanal C, Matthews T. Antibody raised against soluble CD4-rgp120 complex recognizes the CD4 moiety and blocks membrane fusion without inhibiting CD4-gp120 binding. J Exp Med. 1990 Oct. 1; 172(4):1143-1150
5. Moore J P, Sattentau Q J, Klasse P J, Burkly L C. A monoclonal antibody to CD4 domain 2 blocks soluble CD4-induced conformational changes in the envelope glycoproteins of human immunodeficiency virus type 1 (HIV-1) and HIV-1 infection of CD4+ cells. Journal of Virology. 1992; 66(8):4784-4793.
6. Wang, C. Y. "Antibodies against a host cell antigen complex for pre and post exposure protection from infection by HIV." U.S. Pat. No. 5,912,176, 1999.
7. Wang, C. Y., Sawyer, L. S. W., Murthy, K. K., et al. "Postexposure immunoprophylaxis of primary isolates by an antibody to HIV receptor complex." Proc. Nat. Acad. Sci. USA. 1999, 96, 10367-10372.
8. Lynn, S. and Wang, C. Y. "Designed deimmunized monoclonal antibodies for protection against HIV exposure and treatment of HIV infection." U.S. Pat. No. 7,501,494 (Issued Mar. 10, 2009).
9. Chiba, Y., "Leu3A Binding Peptides." U.S. Pat. No. 5,171,838 (1992).
10. Jameson, B. D., Rao, P. E., Kong, L. L. et al. Location and chemical synthesis of a binding site for HIV-1 on the CD4 protein. Science. 1988, 240, 1335-1339.
11. Kuritzkes, D. R., Jacobson, J. L., Powderly, W. G., et al. "Antiretroviral activity of the anti-CD4 monoclonal antibody TNX-355 in patients infected with HIV type I." J. Infect. Dis. 2004. 189:286-291.
12. Yan-Mei Jiao et al. CD4+CD25+CD127 regulatory cells play multiple roles in maintaining HIV-1 p24 production in patients on long-term treatment: HIV-1 p24-producing cells and suppression of anti-HIV immunity. International Journal of Infectious Diseases. 2015; 37:42-49.
13. König R, Shen X, Germain R N: Involvement of both major histocomputibility complex class11 alpha and beta chains in CD4 function indicates a role for ordered oligomerization in T cell activation. J Exp Med 1995; 182:779-787.

BRIEF SUMMARY OF THE INVENTION

The present disclosure is directed to antibodies, compositions, and methods for the treatment and sustained virologic remission of HIV infection in HAART stabilized patients as a replacement for HAART. One aspect of the present disclosure relates to antibodies directed against CD4, compositions thereof, and methods of making and employing such compositions for the treatment and sustained virologic remission of HIV infection in HAART stabilizied patients in the subsequent absence of other treatments, including cART.

In certain embodiments, the antibodies specifically binds to extracellular sites on CD4. In specific embodiments, the antibodies specifically bind to CD4 on sites at or near the CDR2 region in domain 1. The disclosed antibodies exert competitive HIV entry inhibition through its binding to CD4 in both cell-free and cell-to-cell systems. The disclosed antibodies also have the ability to reactivate resting CD4 positive T cells with or without crosslinking, which can lead to an increase in TNF-α production. Such antibodies include, but are not limited to monoclonal antibodies (Mabs) including B4, M2, and dB4C7 (e.g., Wang, C. Y. 1999; Lynn. S. and Wang, C. Y. 2009); Leu3a (Than, S. et al., 1997), ST4 (Briant, L, 1999); and polyclonal antibodies including anti-HIV RC, CDR2 region of domain 1 in CD4 (Wang, C. Y., WO2016/043788).

In certain embodiments, the antibodies are directed against, and specifically bind to, CD4 and, functionally, have the ability to (1) block HIV entry, in both cell-free and cell-to-cell transmission modes and (2) reactivate HIV infected resting CD4 T-cells. In specific embodiments, the antibodies reactivate HIV infected resting CD4 T-cells, in vitro with or without crosslinking, as manifested in an increase in TNF production, HIV p24 release, or T-cell activation via Lck Kinsase phosphorylation. In certain embodiments, treating HIV patients with the disclosed antibodies results in (1) a reduction in regulatory T cells (Tregs); (2) an increase in blood CD8+ cell counts; (3) an expansion of HIV specific CD8+ cells upon in vitro stimulation by HIV specific antigen(s); and/or (4) a reduction in HIV DNA level in blood cells.

The present disclosure is also directed to pharmaceutical compositions comprising the anti-CD4 antibodies (e.g., monoclonal human, humanized, chimeric, etc.) having the above described functional properties as well as methods employing such pharmaceutical compositions for the treatment and sustained virologic remission of HIV infection. Specific embodiments relate to methods of making and/or using the pharmaceutical compositions for the treatment and sustained virologic remission of HIV infection in HAART stabilizied patients in the subsequent absence of cART.

In certain embodiments, the disclosed pharmaceutical compositions comprising the disclosed antibodies are prepared and administered to a patient to reduce the viral load to a non-detectable level with no viral load rebound. In some embodiments, pharmaceutical compositions are prepared and administered to a patient at a dose of about 10 mg/kg or higher on a weekly, biweekly, or even longer schedule. In some embodiments, the pharmaceutical compositions are administered as a monotherapy or in combination with another therapy, such as HAART. In some embodiments, the viral load is reduced to a non-detectable level with no viral load rebound when the serum antibody level in the treated patient is about 10 μg/mL or higher. In certain embodiments, the pharmaceutical composition is given at a dose of about 10 mg/kg or higher on a weekly or biweekly or even longer schedule, as a monotherapy, which leads to a reduction in viral load down to non-detectable level in treated subjects with no viral load rebound as long as the serum antibody level is higher than 10 μg/mL.

The disclosed pharmaceutical compositions comprising antibodies directed against CD4 can be used in HIV treatment as (1) a monotherapy, when administered alone; (2) a combinatorial therapy, when administered as an adjunct to other treatment methods (e.g., cART); or (3) a monotherapy in drug substitution treatment cycles with other treatment methods (e.g., cART) given intermitantly.

The cellular and immunological characteristics achieved with the disclosed antibodies and treatment methods resemble those of an elite controller or long-term nonprogressor (LTNP). That is, the disclosed antibodies and treatment methods are capable of achieving a sustained virologic remission of HIV infection in the subsequent absence of cART, a revolution in the treatment of HIV infection.

BRIEF DESCRIPTION OF THE DRAWINGS

FIG. 1A. A graph illustrating a competitive HIV entry inhibition mechanism. The graph shows theoretical results obtained in a competitive HIV entry inhibition model, where HIV envelope protein gp120 and an inhibitor (e.g., antibody drug) compete for binding on the same portion of a common target surface molecule (i.e., CDR2 of CD4 domain 1). In this model, 100% inhibition of HIV binding/entry can be achieved when the concentration of the inhibitor reaches a certain threshold.

FIG. 1B. HIV-1 entry inhibition from a panel of over 850 Env pseudotype HIV viruses collected over a 10 year period using mAb B4. MAb B4 offers both breadth and potency in HIV entry inhibition with nearly 100% maximum percent inhibition (MPI) in all 850 Env pseudotype viruses with $IC_{50}$ clustered around two concentrations one between 0.01 to 1 μg/mL and the second one around 10 μg/mL.

FIG. 3. Bar graph showing virus reactivation in resting PBMCs (as measured by HIV-1 p24 gag production) induced by the following stimuli: unstimulated (lane 1), PHA (lane 2), inactivated HIV (iHIV) lysate (lane 3), monoclonal antibody directed at CDR2 region of CD4 domain 1 (lane 4), monoclonal antibody directed at CDR3 region of CD4 domain (lane 5), monoclonal antibody directed at CD4 domains 1/2 (lane 6), iHIV in the presence of soluble CD4 (lane 7), monoclonal antibody directed at CDR2 region of CD4 domain 1 in the presence of soluble CD4 (lane 8), monoclonal antibody directed at CDR3 region of CD4 domain 1 in the presence of soluble CD4 (lane 9), and monoclonal antibody directed at CD4 domains 1/2 in the presence of soluble CD4 (lane 10), as depicted in the figure legend (adapted from Briant L., et al., 1999).

FIG. 6. Graph showing antibody titration of mAb dB4 and anti-HIV RC polyclonal antibodies to surface CD4 on PBMCs. The antibody titration was determined as % CD4 binding vs antibody concentration in μg/mL.

FIGS. 7A to 7G. Analysis of mAb dB4 and anti-HIV RC polyclonal antibody inhibition of superantigen SEB induced production of cytokines IL2 and IFN-γ by proliferating CD4+ and CD8+ T cells in treatment naïve HIV positive and HIV negative subjects. MAb dB4 and anti-HIV RC polyclonal antibody inhibition of IL2 production by superantigen induced proliferating CD4+ T cells for HIV negative (FIG. 7A) and HIV positive (FIG. 7B) subjects are shown. MAb dB4 and anti-HIV RC polyclonal antibody inhibition of IL2 production by superantigen induced proliferating CD8+ T cells for HIV negative subjects and age-matched HIV positive subjects (FIG. 7C) are also shown. MAb dB4 and anti-HIV RC polyclonal antibody inhibition of IFN-γ production by superantigen induced proliferating CD4+ T cells for HIV negative (FIG. 7D) and HIV positive (FIG. 7E) subjects are shown. MAb dB4 and anti-HIV RC polyclonal antibody inhibition of IFN-γ production by superantigen induced proliferating CD8+ T cells for HIV negative (FIG. 7F) and HIV positive (FIG. 7G) subjects are also shown.

FIGS. 8A to 8D. Graphs showing the clinical efficacy of UB-421 treatment, as measured by viral load reduction (upper panels), and pharmacokinetics of UB-421, as measured by μg/mL serum concentration (lower panels), over the course of a Phase IIa clinical trial. The relevant data are provided for the following representative patients: Patient 1-1-01 receiving 10 mg/kg weekly administrations of UB-421 (FIG. 8A); Patient 1-1-02 receiving 10 mg/kg weekly administrations of UB-421 (FIG. 8B); Patient 1-2-03 receiving 25 mg/kg bi-weekly administrations of UB-421 (FIG. 8C); and Patient 1-2-06 receiving 25 mg/kg bi-weekly administrations of UB-421 (FIG. 8D). Duration of UB-421 binding on PBMC CD4+ cells indicative of full coating of the cells is shaded in grey.

FIGS. 9A and 9B. FIG. 9A are graphs showing relatively stable CD4 T cell counts (mean and STD) in the per-protocol (PP) population who received all administrations of either a 10 mg/kg of the study drug UB-421 (top) or 25 mg/kg of the study drug UB-421 (bottom) with a valid baseline. FIG. 9B shows the proliferative percentage of CD3+, CD3+/CD4+ cells from patents before (W1), at the end (W8) and after the monitoring period (W16) of the treatment when PBMC are obtained from patients receiving UB421 and stimulated by antigens including superantigen SEB (upper panel) or CMV pp65 (lower panel).

FIGS. 10A and 10B. Graphs showing a theoretical comparison of viral load reduction observed in a Phase IIa clinical trial using UB-421 against the viral load reduction observed in similar studies for TMB-355 (ibalizumab, formerly TNX-355) performed by others (Jacobson, J. L., et al., 2009; Toma, J., et al., 2011; and Pace, C. S., et al., 2013). FIG. 10A summarizes the viral load changes observed in subjects treated with 10 mg/kg and 25 mg/kg of UB-421, while FIG. 10B summarizes the viral load changes observed in subjects treated with the same dosage levels of TMB-355.

FIG. 12. Schematic showing the protocol design from both cohort 1 and cohort 2 for a treatment modality employing UB-421 monotherapy as a substitute for antiretroviral therapy in HIV-1 infected adults.

FIG. 13. Graph showing relatively stable CD4 T cell counts (mean and STD) in patients who received all administrations of either a 10 mg/kg of the study drug UB-421 (cohort 1) or 25 mg/kg of the study drug UB-421 (cohort 2) at the beginning (V1) or end (V12) of the treatment. There is no statistically significant difference before and after the treatment for both cohort 1 (P=0.331) and cohort 2 (P=0.905).

FIG. 14. Graph showing CD8 T cell counts (mean and STD) in patients who received all administrations of either a 10 mg/kg of the study drug UB-421 (cohort 1) or 25 mg/kg of the study drug UB-421 (cohort 2) at the beginning (V1) or end (V12) of the treatment. There is statistically significant difference before and after the treatment for both cohort 1 (P<0.001) and cohort 2 (P=0.004).

FIG. 15A for cohort 1 and 15B for cohort 2.

FIGS. 16A and 16B. Graphs showing the clinical efficacy of UB-421 treatment as measured by individual patient viral load reduction (HIV RNA copies/mL) over the course of a Phase II clinical trial employing UB-421 monotherapy as a substitute for antiretroviral therapy in HIV-1 infected adults. FIG. 16A for cohort 1 and 16B for cohort 2. Viral rebound is defined by viral load exceeding 400 RNA copies/mL in two consecutive visits (dashed line).

FIG. 20. Comparison of efficacy in maintenance of HIV viral suppression for monotherapies employing either (1) HIV drugs (HAART) on the market or monoclonal antibodies (2) VRC01, (3) Pro140 targeting HIV co-receptor CCR5 or (4) UB421 for a period from 4 to 16 weeks.

Figure 21:
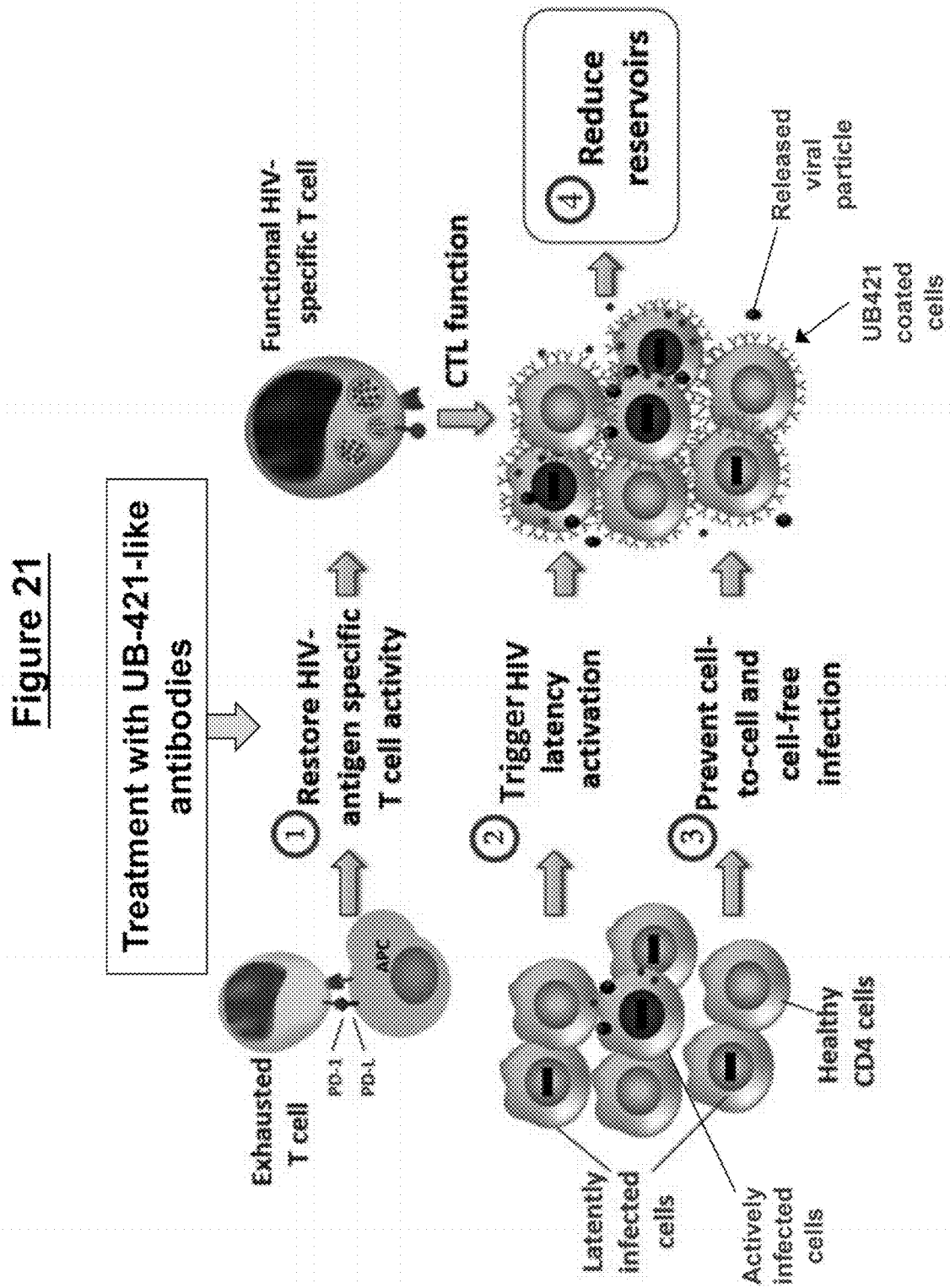

FIG. 21. Cellular mechanisms mediated by UB421-like antibodies upon treatment include: (1) restoration of HIV antigen specific T cell activity by reduction of % Treg cells, (2) activation of HIV latency in infected cells upon antibody binding, and (3) prevention of cell-to-cell and cell-free infection to halt new HIV infection; all of which results in (4) the reduction or elimination of viral reservoirs leading to sustained virological remission of HIV-1 infection.

Figure 22A:
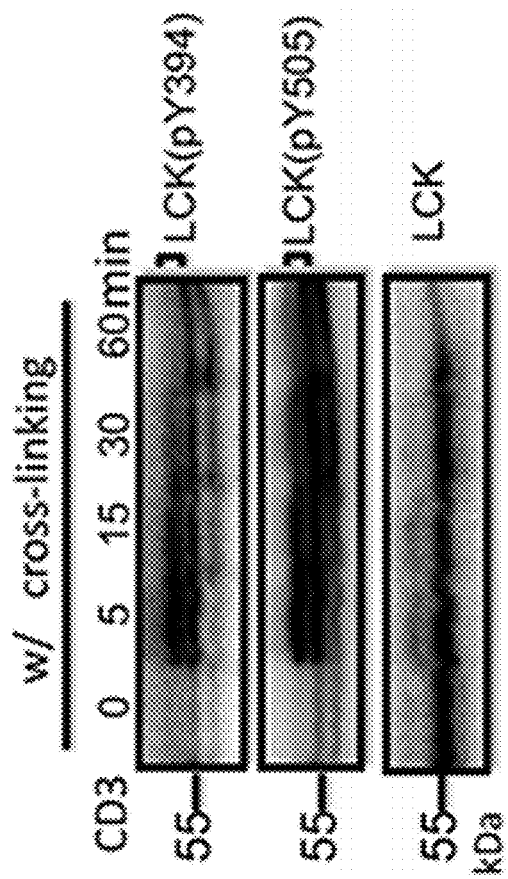
Figure 22B:
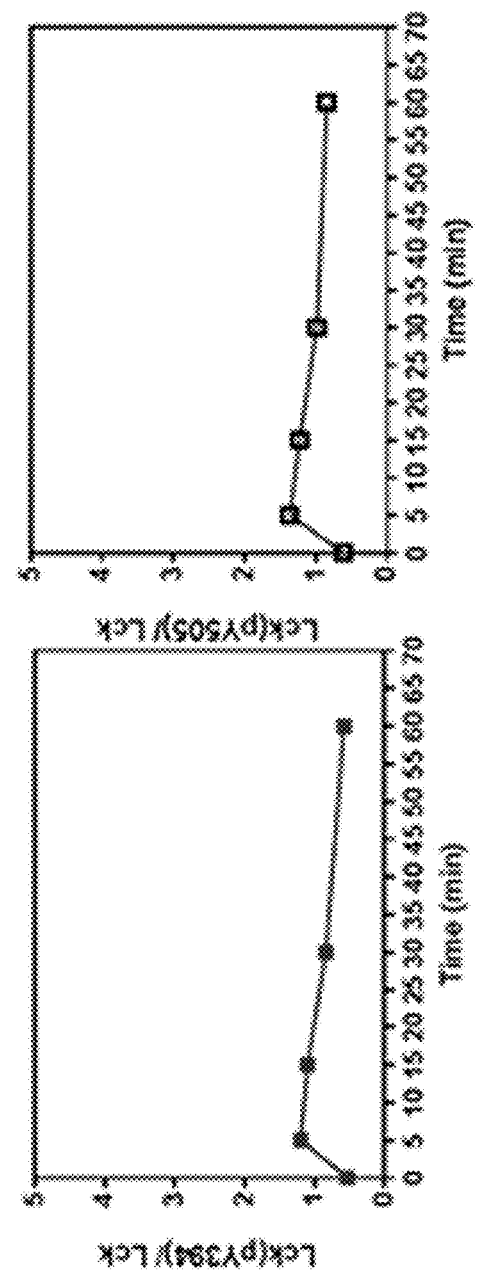
Figure 22C:
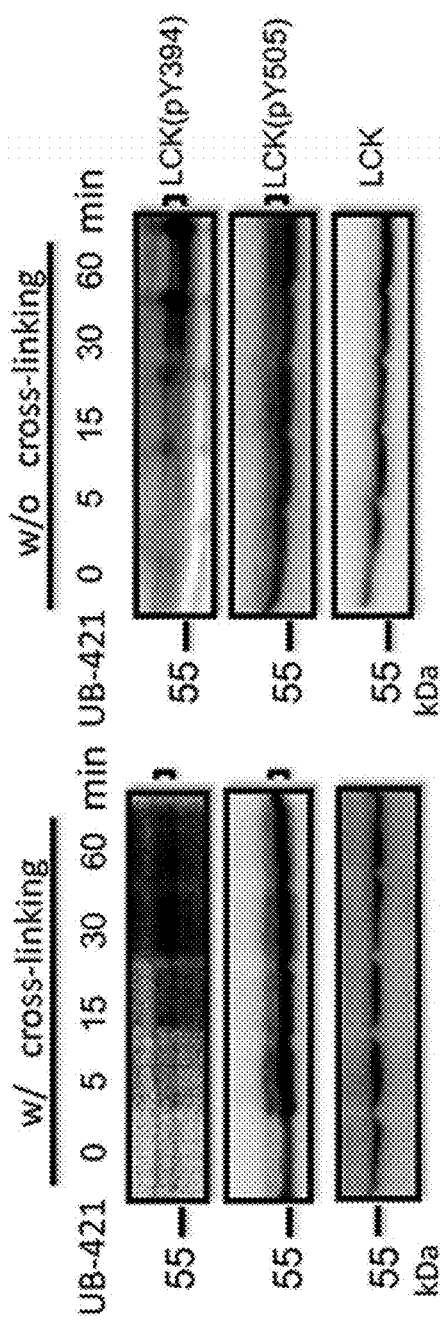
Figure 22D:
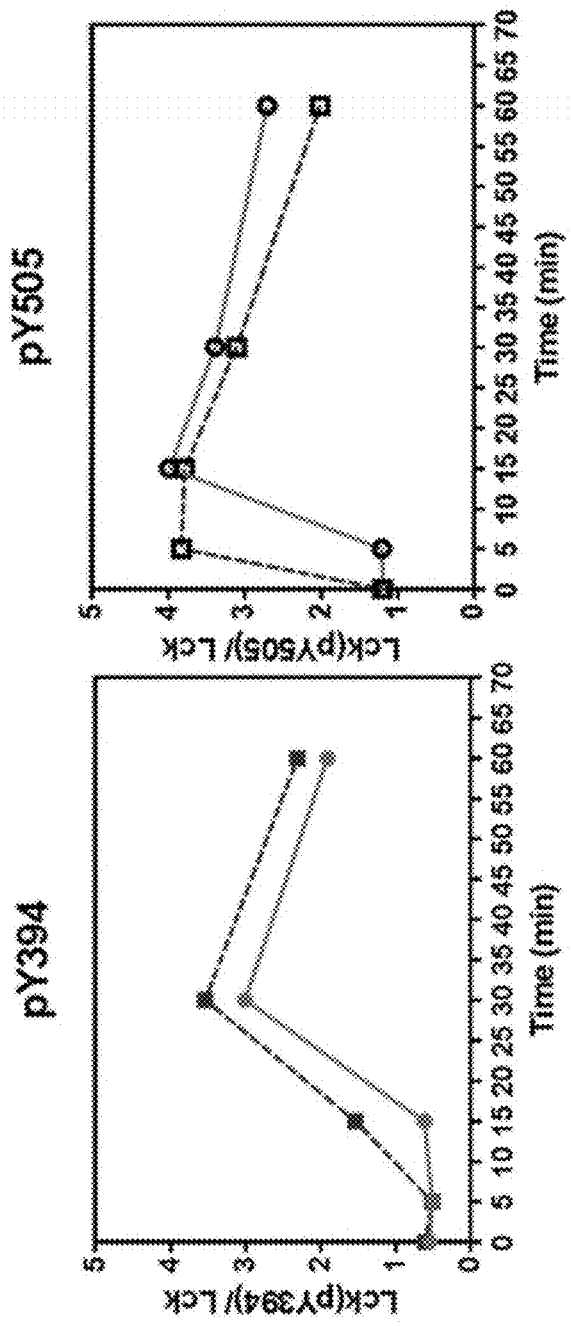

FIGS. 22A to 22D. Western blot analysis of Lck phosphorylation on tyrosine 394 (Y394) and tyrosine 505 (Y505) in Jurkat T cells. FIG. 22A are Western blot images of Lck Y394 phosphorylation (top) and Y505 phosphorylation (middle), and total Lck protein level after stimulation (bottom) with anti-CD3 (OKT3) antibody as a positive control. FIG. 22B are graphs showing the Lck Y394 and Y505 phosphorylation level normalized with total Lck of each time point shown in FIG. 22A. FIG. 22C are Western blot images of Lck Y394 phosphorylation (top), Y505 phosphorylation (middle), and total Lck protein level (bottom) with UB-421 stimulation with or without crosslinking. FIG. 22D are graphs showing Lck Y394 and Y505 phosphorylation levels normalized with total Lck of each time point shown in FIG. 22C, where dashed lines represent data obtained under crosslinking condition and solid lines represent data obtained under conditions without crosslinking.

Figure 23A:
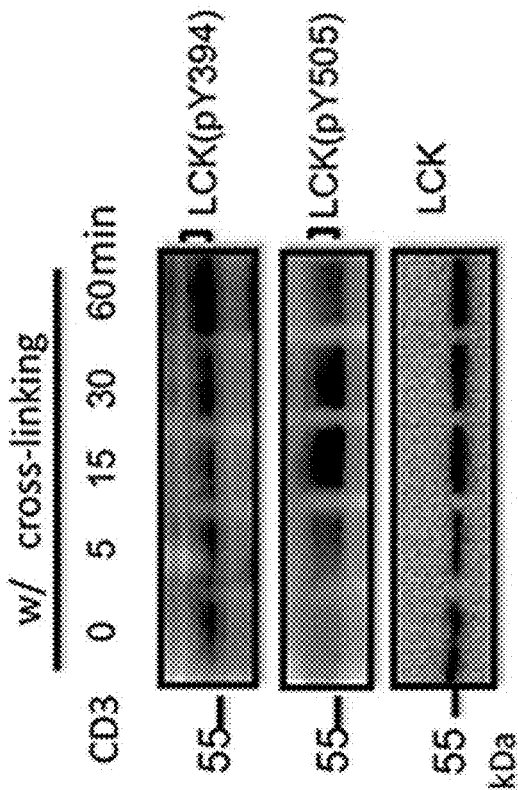
Figure 23B:
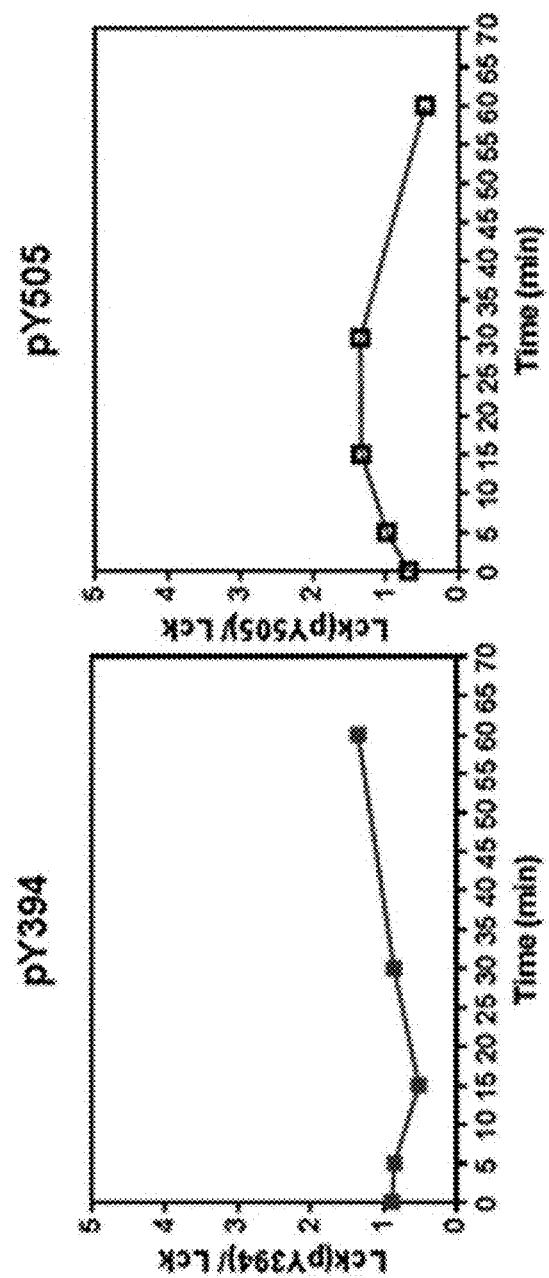

FIGS. 23A to 23B. Western blot analysis of Lck phosphorylation with anti-CD3 (OKT-3) stimulation in primary CD4$^+$ T cells from normal blood Donor 3. FIG. 23A are Western blot images of Lck Y394 phosphorylation (top), Y505 phosphorylation (middle), and total Lck protein level (bottom) with anti-CD3 (OKT3) antibody stimulation. FIG. 23B are graphs showing Lck Y394 and Y505 phosphorylation levels normalized with total Lck of each time point in FIG. 23A.

Figure 24B:
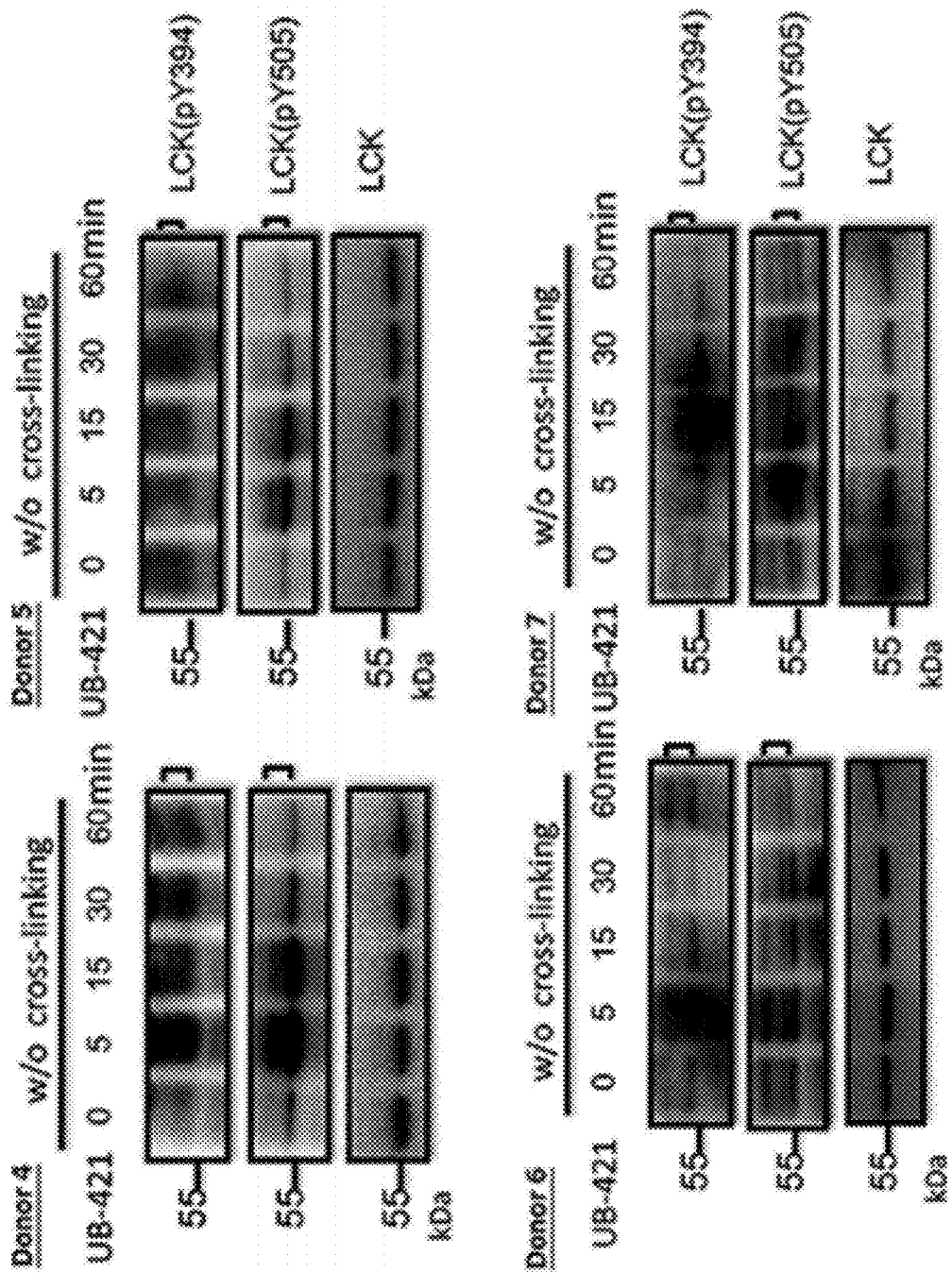
Figure 24C:
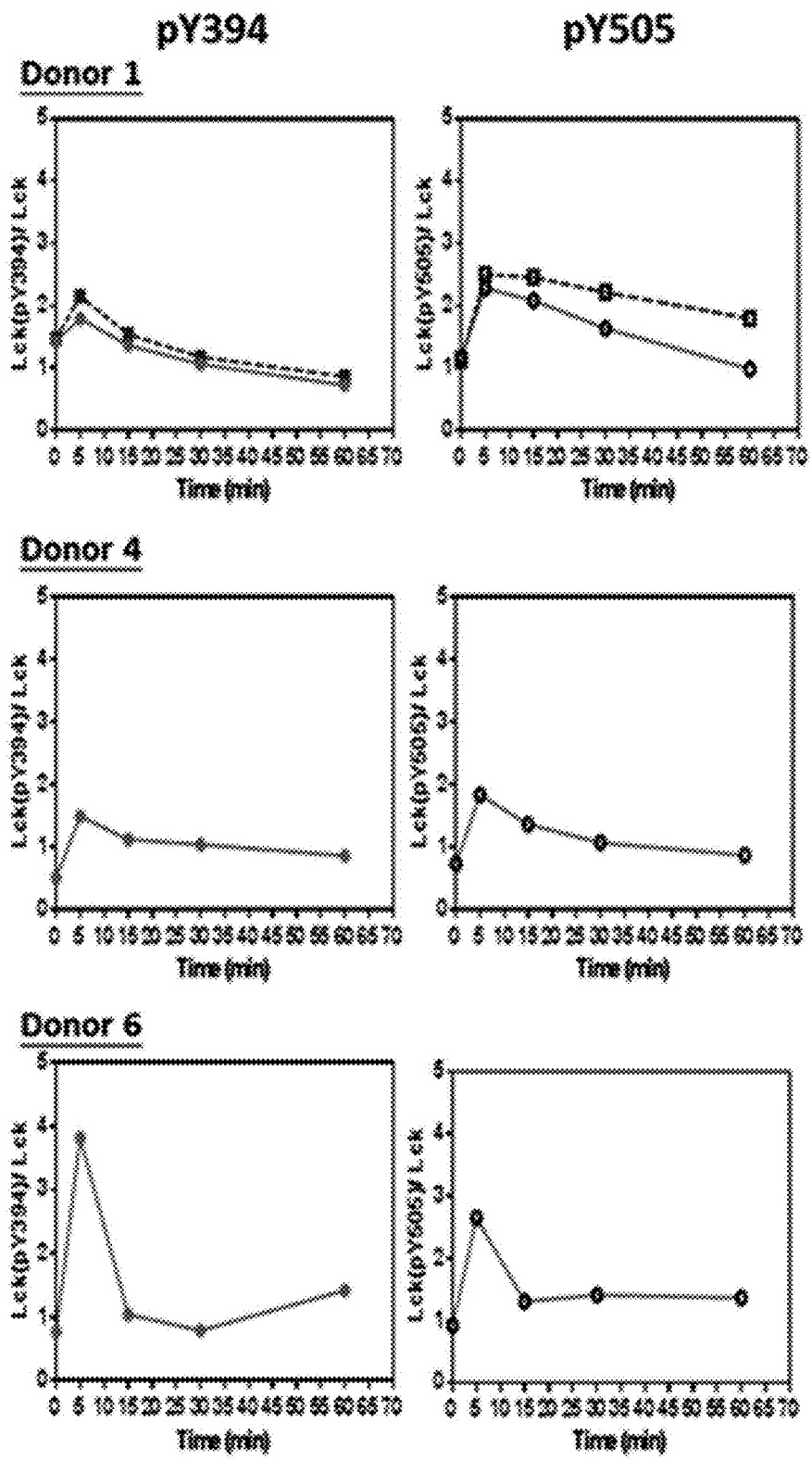
Figure 24D:
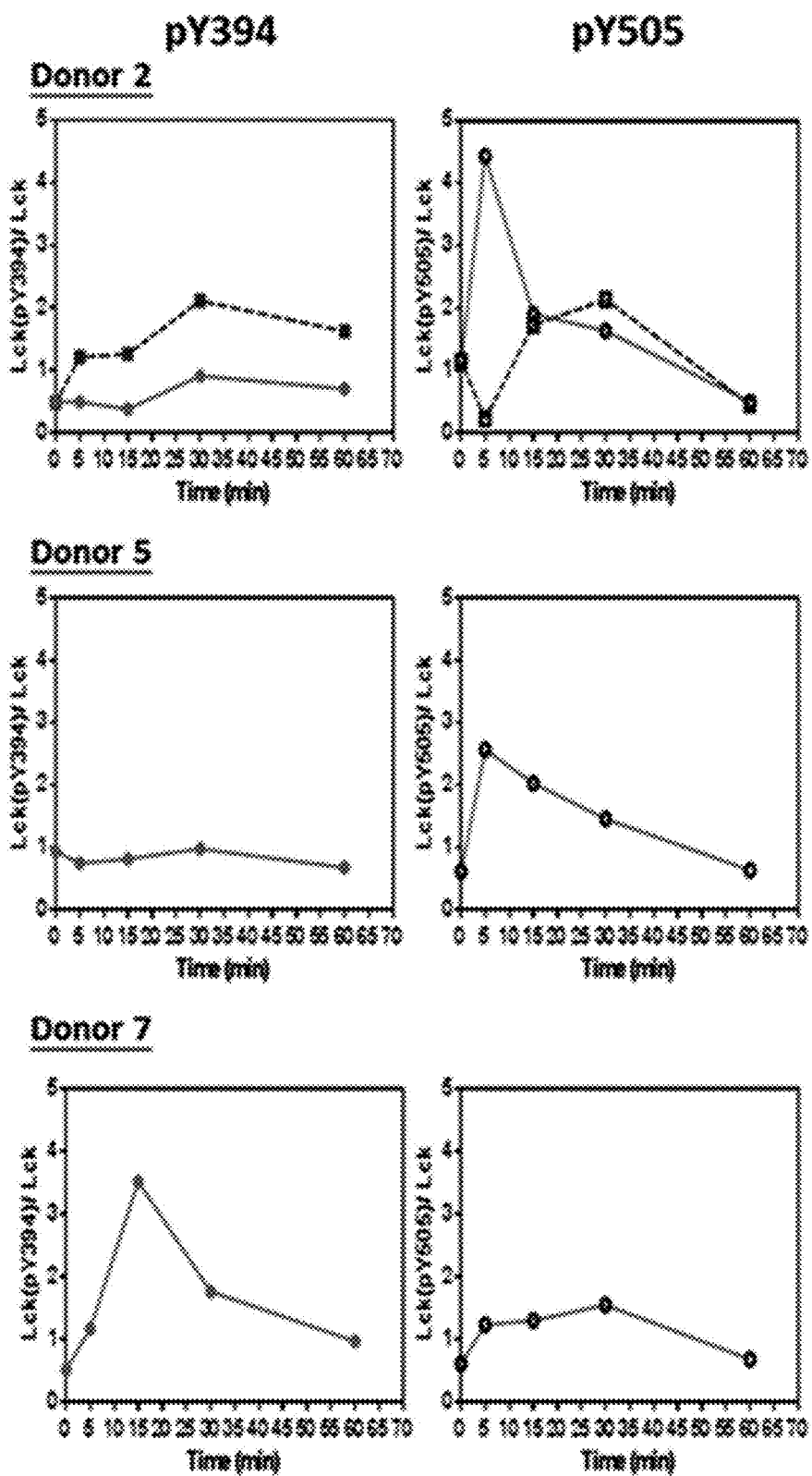

FIGS. 24A to 24D. Western blot analysis of Lck phosphorylation with UB-421 stimulation in primary CD4$^+$ T cells from normal blood Donors 1, 2, 4, 5, 6, and 7. FIG. 24A are Western blot images of Lck Y394 phosphorylation (top), Y505 phosphorylation (middle), and total Lck protein level (bottom) with UB-421 stimulation with or without crosslinking in healthy Donors 1 and 2. FIG. 24B are Western blot images of Lck Y394 phosphorylation (top), Y505 phosphorylation (middle), and total Lck protein level (bottom) with UB-421 stimulation without crosslinking in healthy Donors 4, 5, 6, and 7. FIG. 24C and FIG. 24D are graphs showing Lck Y394 and Y505 phosphorylation levels normalized with total Lck of each time point in FIGS. 24A and 24B, where the dashed lines represent data obtained under crosslinking condition and solid lines represent data obtained under conditions without crosslinking.

Figure 25A:
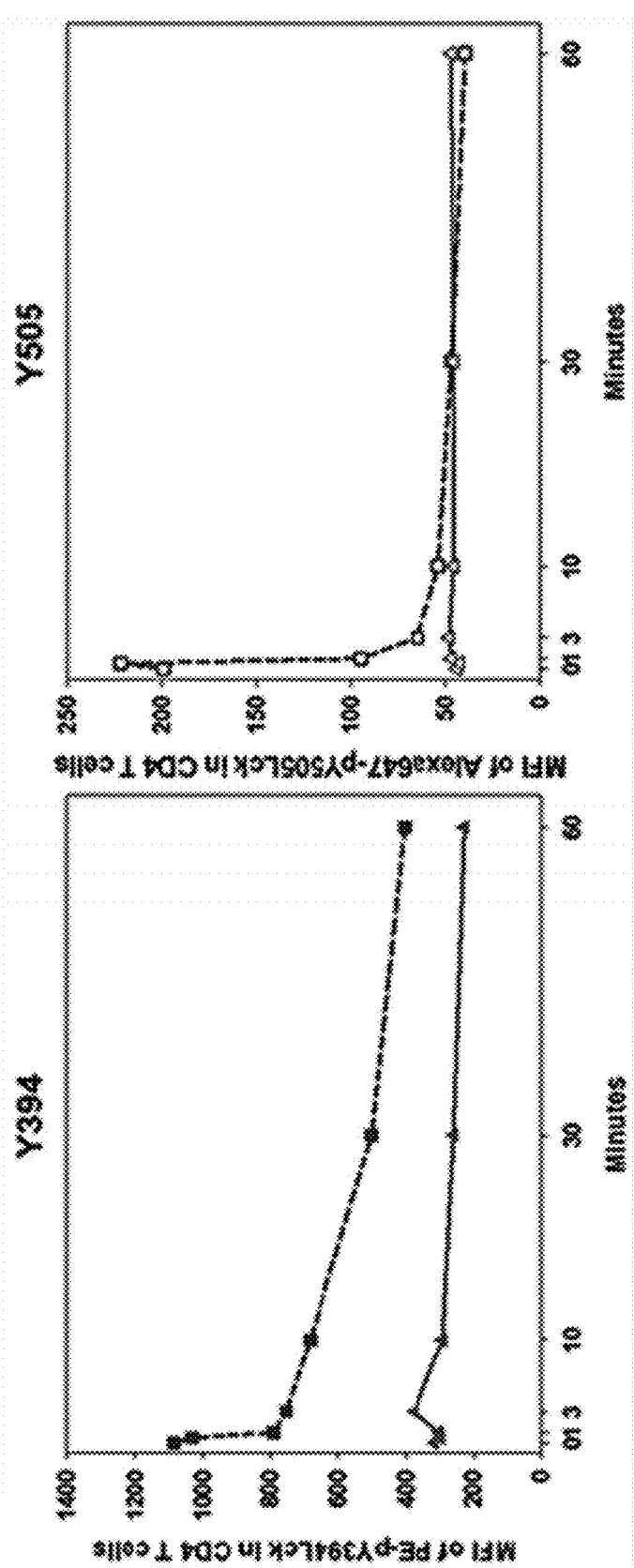

FIGS. 25A to 25B. Flow cytometry analysis of Lck phosphorylation in primary CD4$^+$ T cells from normal blood Donors 8 and 9. FIG. 25A shows the MFI of PE-anti-Lck pY394 (left) and Alexa647-anti-LckpY505 (right) with either anti-CD3 stimulation (dashed line) as a positive control or without any treatment (solid line) as a negative control. FIG. 25B shows the MFI of PE-anti-Lck pY394 (left) and Alexa647-anti-LckpY505 (right) of primary CD4+ T cells from normal blood Donors 8 and 9 stimulated with UB-421 under crosslinking conditions (dashed line) or under conditions without crosslinking (solid line).

DETAILED DESCRIPTION OF THE INVENTION

The present disclosure is directed to antibodies, compositions, and methods for the treatment and sustained virologic remission of HIV infection in HAART stabilized patients. One aspect of the present disclosure relates to antibodies directed against CD4, compositions thereof, and methods of making and employing such compositions for the treatment and sustained virologic remission of HIV infection in HAART stabilizied patients in the subsequent absence of other treatments, including cART.

The section headings used herein are for organizational purposes only and are not to be construed as limiting the subject matter described. All references or portions of references cited in this application are expressly incorporated by reference herein in their entirety for any purpose.

CD4

Human CD4 (cluster of differentiation 4) is a 458 amino acid glycoprotein (UniProtKB/Swiss-Prot: P01730.1) found on the surface of immune cells such as T helper cells, monocytes, macrophages, and dendritic cells (website: en.wikipedia.org/wiki/CD4). The amino acid sequence of CD4 is shown as SEQ ID NO: 22 in the Sequence Listing. CD4+ T helper cells are white blood cells that are an essential part of the human immune system. They are often referred to as CD4 cells, T-helper cells or T4 cells. They are helper cells because they send signals to other types of immune cells, including CD8 killer cells, which destroy infectious particles. If CD4 cells become depleted, for example in untreated HIV infection, or following immune suppression prior to a transplant, the body is left vulnerable to a wide range of infections that it would otherwise have been able to fight.

CD4 is a co-receptor that assists the T cell receptor (TCR) in communicating with an antigen-presenting cell. CD4 interacts directly with Major Histocompatibility Complex (MHC) class II molecules on the surface of the antigen-presenting cell using its extracellular domain. The extracellular domain adopts an immunoglobulin-like beta-sandwich with seven strands in 2 beta sheets. Using its intracellular domain, CD4 amplifies the signal generated by the TCR by recruiting the tyrosine kinase Lck, which is essential for activating many molecular components of the signaling cascade of an activated T cell. Various types of T helper cells are thereby produced.

The major structural features of CD4 are shown in the Sequence Listing and discussed in further detail below.

CD4 is a member of the immunoglobulin superfamily and has four immunoglobulin domains (D1 to D4) that are exposed on the extracellular surface of the cell. CD4 domains D1 and D3 resemble immunoglobulin variable (IgV) domains; whereas D2 and D4 resemble immunoglobulin constant (IgC) domains.

CD4 Domain 1 (D1)

The D1 core domain (approx. aa 26-125) consists of two β-sheets formed by β-strands that are linked by a disulfide bond bridge. The amino acid sequence of D1 shares homologies with immunoglobulin at three complimentarily determining regions (CDRs) similar to that of immunoglobulin chains. The CDR1-, CDR2-, and CDR3-like regions are located in the D1 domain of CD4.

The D1 domain of CD4 interacts directly with MHC class II molecules on the surface of antigen presenting cells and recruits lck to facilitate the activation of helper T cells, thus modulating the adaptive immune response. Both domain 1 and domain 2 of the extracellular region of the CD4 molecule were found to contribute to the binding sites for class II MHC molecules; however, domain 1 alone was found to be involved with HIV binding and syncytia formation. In particular, the binding site for the HIV envelope glycoprotein gp120 was found to be localized to the CDR2-like loop of D1.

Several anti-CD4 antibodies have been produced that recognize the D1 domain of CD4. For example, HIV RC, B4, M2, and dB4C7 (e.g., Wang, C. Y. 1999; Lynn. S. and Wang, C. Y. 2009; and Wang, C. Y., WO2016/043788); Leu3a (Chiba, Y. 1992); OKT4A (Jameson, B. D., et al., 1988); ST4 and 13B8.2 (Briant, L, 1999); 6H10 (e.g., Moore, et al., 1992); 15A7, 2D5, and 2F2 (e.g., Yuan R, et al., 2016); and F91-55 and BL4, which recognize the region between D1 and D2 (Briant, L, et al., 1999; Celada F, et al., 1990; and Moore, et al., 1992);

CD4 Domain 2 (D2)

The D2 domain of CD4 (approx. aa 126-203) connects with D1 through its hydrophobic interface. D2 contributes to the binding sites for class II MHC molecules. Several anti-CD4 antibodies have been produced that recognize the D2 domain of CD4. For example, ibalizumab (TMB-355; formerly known as TNX-355 or Hu5A8; e.g., Kuritzkes, D. R., et al., 2004); M-T441 (König R, et al., 1995).

CD4 Domain 3 (D3)

The D3 domain of CD4 is located at approx. aa 204-317. D3 connects to D4 through its hydrophobic interface, similar to the way D2 interacts with D1. The antibody OKT4 recognizes D3 (e.g., Yuan R, et al., 2016; Moore, et al., 1992).

CD4 Domain 4 (D4)

The D4 domain (approx. aa 318-374) is the last extracellular domain on the CD4 molecule before the transmembrane domain. D4, structurally resembling D2, is widely believed to activate T cells and CD4 function through the dimerization of CD4 molecules. The antibody OKT4 and L120 recognize D4 (e.g., Yuan R, et al., 2016; Moore et al., 1992).

CD4—Transmembrane Region and Cytoplasmic Region

The transmembrane region (approx. aa 397-418) is hydrophobic whereas the intracellular/cytoplasmic region (approx. 419-458) comprises three serine residues (S433, S440 and S456) that are phosphorylated to mediate signal transduction. These serine residues connect directly with the Src Tyrosine Kinase (TK) family member P56lck, which can increase the level of P56lck tyrosine phosphorylation and regulate signal transduction.

CD4—the Role in HIV Infection

HIV-1 uses CD4 to gain entry into host T-cells and achieves this through its viral envelope protein known as gp120. Gp120 is one of the two domains of the maturing HIV-1 membrane envelope glycoprotein precursor gp160; the other is gp41. The binding of gp120 to CD4 constitutes the first step in HIV-1 attachment and the CD4-gp120 interaction creates a shift in the conformation of gp120 allowing it to bind to chemokine receptors CCR5 or CXCR4 expressed on the host cell. This secondary binding allows the gp41 (fusion peptide) molecule of HIV-1 to insert into the host cell membrane, eventually mediating membrane fusion of the virus with the host. HIV infection leads to a progressive reduction in the number of T cells expressing CD4.

CD4 thus has a key role in the initiation of HIV-1 infection. Comparing bound and unbound crystal structures of gp120 with CD4 shows that a "bridging sheet"—a four-stranded β-sheet formed by two β-hairpins—fixes the relative orientations of the two closely associated "inner" and "outer" domains of the gp120 core during CD4 binding. The CD4 D1 domain interacts with these inner and outer domains as well as the bridging sheet, which leads to the rearrangements of the gp120 inner domain. Furthermore, with additional interactions with the gp120 V3 variable loop, the bridging sheet exposes the co-receptor binding site (e.g., Yuan R, et al., 2016).

Antibody

One aspect of the present disclosure relates to an antibody directed against CD4, compositions thereof, and methods employing such compositions for the treatment and sustained virologic remission of HIV infection.

The antibody of the present disclosure broadly encompasses intact antibody molecules, which include intact polyclonal, monoclonal, monospecific, polyspecific, chimeric, deimmunized, humanized, human, primatized, single-chain, single-domain, synthetic and recombinant antibodies. The present disclosure also includes portions of intact antibodies that have a desired activity or function (e.g., immunological fragments of antibodies).

The antibody of the present disclosure is directed against CD4. In some embodiments, the antibody specifically binds to the extracellular region of CD4. In certain embodiments, antibody specifically recognizes and binds to at least one of the immunoglobulin domains (D1 to D4) of CD4. In certain embodiments, the antibody binds to only one of the immunoglobulin domains of CD4 (i.e., D1, D2, D3, or D4). In specific embodiments, the antibody binds to the D1 domain of CD4. In some embodiments, the antibody binds to CD4 at or nearby a complimentarily determining region (CDR1, 2, or 3) in the D1 domain. In specific embodiments, the antibody binds to CD4 at or nearby the CDR2 region of the D1 domain.

The antibody of the present disclosure can be produced by any standard method. In some embodiments, the disclosed antibody is produced by immunizing an animal (e.g., mouse, dog, guinea pig, pig, goat, horse, etc.) with a recombinant CD4 protein, fragments of the CD4 protein, fusion proteins containing immunological portions of CD4, and/or analogues or homologues of CD4. In other embodiments, the antibody can be produced by immunizing an animal with cells that express CD4 on the surface. In yet other embodiments, the antibody can be chemically synthesized.

In certain embodiments, the antibody is produced by immunizing an animal with a CD4 protein, fragments of the CD4 protein, fusion proteins containing immunological portions of CD4, and/or analogues or homologues of CD4. In some embodiments, the antibody is produced by immunizing an animal with a peptide containing the full-length CD4 protein. In other embodiments, the antibody is produced by immunizing an animal with a peptide containing a portion of the CD4 protein. For example, the peptide can contain a portion of the CD4 protein representing the extracellular region (e.g., D1 to D4), an immunoglobulin domain (D1, D2, D3, and/or D4), a complimentarily determining region (CDR1, 2, or 3) within the D1 domain, etc. The antibody can be produced by immunizing an animal with a single peptide comprising at least a portion of CD4 or a combination of peptides containing the amino acid sequence of CD4. In some embodiments, the peptide immunogen contains aa39-66 of CD4, which is also known to as the HIV receptor complex ("HIV RC"), as HIV binds to this portion of CD4. In a specific embodiment, the HIV RC peptide is made cyclic through a disulfide bond. In some embodiments, polyclonal antibodies are produced by immunizing an animal with the cyclic HIV RC peptide. The term "anti-HIV RC polyclonal antibodies", as used herein, refers to immune sera directed against a cyclic peptide containing aa39-66 of the CDR2 region of CD4 domain 1.

In other embodiments, the antibody is produced by immunizing an animal with CD4 positive cells. The cell lines can be any cell line that expresses CD4, such as Jurkat cells, HPB-ALL cells, U87MG cells, NIH-3T3 cells, HOS cells, CCRF-CEM cells (ATCC® CCL-119™), HuT 78 (ATCC® TIB-161™), MJ (G11) (ATCC® CRL-8294™), and the like. In certain embodiments, the antibody can be produced by immunizing BALB/c mice with intact, uninfected CD4+ human HPB-ALL cells, a T-acute lymphoblastic leukemia cell line or purified peripheral blood mononuclear T cells (PBL T cells). Such antibodies are discussed in further detail in U.S. Pat. Nos. 5,912,176, 6,090,388 and WO/2016/043788 by Wang and the journal article by Wang et al., 1999, all of which are incorporated by reference in their entireties.

In certain embodiments, the antibody of the present disclosure is tagged or labeled with a chemical. For example, the antibody can be labeled with biotin, spacer arms, probes (e.g., FITC, PE, TRITC, DyLight Fluors, Alexa, GFP, R-Phycoerythrin, quantum dots, etc.), enzyme conjugates, and combinations thereof. In a specific embodiment, the antibody is labeled with a biotin or fluorescent probe.

In specific embodiments, the antibody can be modified through a process known as deimmunization. The term "deimmunization", as used herein, generally refers to a process for modifying portions of an antibody so that it can be administered to an animal without triggering an immune response within the animal. Specifically, deimmunization involves a process for locating and removing portions of the amino acid sequence of the antibody that would be immunogenic (e.g., T-cell epitopes) in the particular animal that is being administered the antibody. This process can be accomplished through the combined use of immunological and molecular biology techniques. This process has been described previously (e.g., Jones, T. D., et al. 2009). In the case of deimmunization of antibodies, mutations to remove T-cell epitopes can generally be introduced without significantly reducing the binding affinity of the antibody.

The term "humanized", as used herein, refers to an antibody that was originally produced by a non-human species whose protein sequence has been modified (deimmunized), in a manner that removes the immunogenicity of the antibody when it is administered to a human. In certain embodiments, the disclosed antibody is deimmunized for human use by replacing the constant regions with human constant regions and/or by expression of genes encoding these antibodies in mammalian cells.

The term "mAb B4" or "B4" or "murine B4" as used herein, refers to a murine monoclonal antibody which has been shown to recognize CD4 and can inhibit HIV entry. The structural and functional characteristics of this antibody are discussed in further detailed in the Examples that follow.

The term "mAb dB4" or "dB4", as used herein, refers to the human deimmunized antibody derived from mAb B4. In one embodiment, mAb B4 is deimmunized for human use according to the method described in U.S. Pat. Nos. 7,501,494 and 7,872,110, which are incorporated by references in their entireties. In a particular embodiment, the human deimmunized mAb dB4 is produced by removing and replacing the constant regions of the murine antibody (CH and Cκ) of mAb B4 and with the constant regions of human IgG1. MAb dB4 encompasses the dB4 produced by any suitable cellular clone. In a specific embodiment, mAb dB4 is produced by clone 7.

The term "mAb dB4C7" or "dB4C7", as used herein, refers to mAb dB4 expressed by clone 7 containing the recombinant genes B4DIVHv1/VK1CHO#7 that was described previously in U.S. Pat. Nos. 7,501,494 and 7,872,110, and WO/2016/043788 by Wang which are incorporated by references in their entireties. The C7 clone has been shown to produce high quantities of mAb dB4 antibody. Additionally, the Asn (N) residue at position 298 in mAb dB4C7 has been substituted with His (H), to remove the N-glycosylation site, thus eliminating the IgG mediated complement dependent cytotoxicity (CdC) to prevent depletion of CD4 positive T cells in the presence of antibody B4.

The term "UB-421", as used herein, refers to the mAb dB4C7 that is used in a suitable form to be administered to human subjects.

The antibody can contain post-translational modifications, including sites for glycosylation, methylation, and/or phosphorylation. In certain embodiments, the antibody has a sugar binding residue. In specific embodiments, the antibody contains an asparagine (Asn) residue that serves as a glycosylation site. In particular embodiments, the Asn residue is on the heavy chain, and in specific embodiments, the Asn is in the Fv region and/or in a CDR.

The antibody of the present disclosure can also be described by its interesting and unique functional characteristics.

For example, the disclosed antibody exerts potent competitive HIV entry inhibition through its binding to domain 1 of CD4. In particular, the disclosed antibody has nearly 100% maximum percent inhibition (MPI) in all Env pseudotype viruses tested, with $IC_{50}$s clustered around two concentrations; one between 0.01 to 1 μg/mL and the second one around 10 μg/mL. The binding activity of the disclosed antibody is about two logs higher (i.e. 100× tighter binding) than the CD4 binding affinity exhibited by HIV gp120 envelope protein. Additionally, the mean Kd of the disclosed antibody was estimated to be $5.6 \times 10^{-11}$M (range: 3.1 to $8.1 \times 10^{-11}$M), and the Bmax was estimated to be $1.2 \times 10^6$ Ab per cell (range: $0.93$-$1.4 \times 10^6$).

The competitive inhibition property for the disclosed antibody has been shown in both cell-free and cell-to-cell systems. The disclosed antibody binds to CD4 receptors with an affinity at least 50-fold higher than that for HIV-1 envelope protein gp120 MN. Also, the disclosed antibody binds to CD4 with greater affinity and specificity compared to other commercially available antibodies, such as Leu3a.

The disclosed antibody can also inhibit antigen induced T cell proliferation and cytokine production (IL2 and IFN-gamma) of CD4 positive T cells, which is implicated in the pathogenic cycle of pyroptosis. Such high affinity monoclonal antibodies to CD4 inhibit antigen such as superantigen SEB (staphylococcal enterotoxin B, SEB) induced CD4 positive T cell activation and cytokine (e.g. IL2 and IFN-γ) production. Such antigen induced activation leading to cytokine production in quiescent CD4+ T cells having abortive HIV infection would lead to pyroptosis of these quiescent CD4+ T cells and nearby normal resting CD4 positive cells resulting in ensuing mass depletion of CD4+ T cells, thus AIDS.

The disclosed antibody also has the ability to reactivate resting CD4 positive T cells. This property is particularly useful for reactivating latent reservoirs of HIV in resting T cells to make these cells susceptible to treatment with antiretroviral agents. Such high affinity antibodies to CD4 are capable of activating resting HIV infected cells for the release of HIV. Reactivation of HIV infected resting CD4+ T cells allows combinational treatment incorporating antibody of the current invention with HAART in HIV infected patients leading to functional cure.

Additional structural and functional characteristics of the disclosed antibodies are provided in the Examples that follow.

Formulation

The present disclosure is also directed to pharmaceutical formulations that can be used for the prevention, treatment, and/or functional cure of HIV infection. In certain embodiments, the formulations contain antibodies directed against CD4. In specific embodiments, the present disclosure relates to pharmaceutical compositions comprising high affinity monoclonal antibodies to CD4 that are directed to sites within or nearby CDR2 region of CD4 domain 1. The binding activity ($EC_{50}$) of such antibodies is about two logs higher (i.e. 100× tighter binding) than the CD4 binding affinity exhibited by HIV gp120 envelope protein ($EC_{50}$ for gp120=97 nM).

Pharmaceutical formulations of the antibody proteins disclosed can be prepared by mixing an antibody protein with optional pharmaceutically acceptable carriers. Pharmaceutically acceptable carriers include solvents, dispersion media, isotonic agents and the like. The carrier can be liquid, semi-solid, e.g. pastes, or solid carriers. Examples of carriers include water, saline solutions or other buffers (such as phosphate, citrate buffers), oil, alcohol, proteins (such as serum albumin, gelatin), carbohydrates (such as monosaccharides, disaccharides, and other carbohydrates including glucose, sucrose, trehalose, mannose, mannitol, sorbitol or dextrins), gel, lipids, liposomes, resins, porous matrices, binders, fillers, coatings, stabilizers, preservatives, antioxidants including ascorbic acid and methionine, chelating agents such as EDTA; salt forming counter-ions such as sodium; non-ionic surfactants such as TWEEN™, PLURONICS™ or polyethylene glycol (PEG), or combinations thereof.

The formulation can contain more than one active compound. For example, the formulation can contain one or more antibody and/or one or more additional beneficial compound for preventing and treating HIV infections. The active ingredients can be combined with the carrier in any convenient and practical manner, e.g., by admixture, solution, suspension, emulsification, encapsulation, absorption and the like, and can be made in formulations such as tablets, capsules, powder (including lyophilized powder), syrup, suspensions that are suitable for injections, ingestions, infusion, or the like. Sustained-release preparations can also be prepared.

In certain embodiments, the pharmaceutical formulation contains mAb dB4C7 for human use. The pharmaceutical formulation containing mAb dB4C7 can be prepared in an appropriate buffer including, but not limited to, citrate, phosphate, Tris, BIS-Tris, etc. at a pH between 6.0 to 7.0 and can also contain excipients such as sugars (50 mM to 500 mM of sucrose, trehalose, mannitol, or mixtures thereof), surfactants (e.g., 0.025%-0.5% of Tween 20 or Tween 80), and/or other reagents. In a specific embodiment, the formulation contains mAb dB4C7 in 20 mM glycine, and 0.05% (v/v) Tween (polysorbate 20) in phosphate buffer saline (PBS), pH 6.5. In another specific embodiment, high concentration formulations of mAb dB4 were also prepared for use in certain applications including subcutaneous injections, which included 10 mM histidine.

The formulation can be prepared to contain various amounts of antibody. In general, formulations for administration to a subject contain between about 0.1 mg/mL to about 200 mg/mL. In certain embodiments, the formulations can contain between about 0.5 mg/mL to about 50 mg/mL; between about 1.0 mg/mL to about 50 mg/mL; between about 1 mg/mL to about 25 mg/mL; or between about 10 mg/mL to about 25 mg/mL of antibody. In specific embodiments, the formulations contain about 1.0 mg/mL, about 5.0 mg/mL, about 10.0 mg/mL, or about 25.0 mg/mL of antibody.

In specific embodiments, the present invention relates to pharmaceutical compositions comprising human, humanized or chimeric, monoclonal anti-CD4 antibodies with the above described binding characteristics which exhibit competitive HIV entry inhibition as well as activation of CD4+ T cells, as an immunotherapy in patients with HIV infection.

In another embodiment, the present invention relates to pharmaceutical compositions comprising monoclonal human, humanized or chimeric, anti-CD4 antibodies with the above described binding characteristics that serve as a monotherapy that can reduce viral load down to non-detectable level in treated subjects at a serum antibody level higher than 10 μg/mL.

In another embodiment, the present invention relates to pharmaceutical compositions comprising monoclonal human, humanized or chimeric, anti-CD4 antibodies with the above described binding characteristics that serve as a monotherapy that can reduce viral load down to non-detectable level in treated subjects at a serum antibody level higher than 10 μg/mL and maintained stable CD4 T cell counts during a 12-weeks treatment period.

In certain embodiments, the present invention relates to pharmaceutical compositions comprising monoclonal human, humanized or chimeric) anti-CD4 antibodies with the above described binding characteristics that when given, at a dose of about 10 mg/kg or higher on a weekly or biweekly schedule, as a monotherapy, such treatment can reduce viral load down to non-detectable level in treated subjects during a 12-weeks treatment period.

In yet another preferred embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to treatment naïve HIV patients, will lead to functional cure of the patients.

In yet another preferred embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to patients with stabilized viral load under HAART, will lead to functional cure of the patients.

Antiviral Agents

The present disclosure also includes antiviral agents that can be used in the methods for the treatment, prevention, and functional cure of HIV infection.

Antiviral agents include any agent (compound or biological) that is effective to inhibit the formation and/or replication of HIV in a mammal. Examples of antiviral agents include, but are not limited to, entry/fusion inhibitors (e.g., maraviroc, enfuvirtide); nucleoside reverse transcriptase inhibitors (NRTI) and nucleotide reverse transcriptase inhibitors (NtRTI) (e.g., zidovudine, abacavir, didanosine, lamivudine, emtricitabine, stavudine, and tenofovir); non-nucleoside reverse transcriptase inhibitors (NNRTI) (e.g., nevirapine, efavirenz, etravirine, and rilpivirine); integrase inhibitors also known as integrase nuclear strand transfer inhibitors or INSTIs (e.g., raltegravir, dolutegravir, elvitegravir); protease inhibitors (e.g., saquinavir, saquinavir mesylate, fosamprenavir, tipranavir, lopinavir, indinavir, nelfinavir, amprenavir, ritonavir, darunavir, atazanavir, bevirimat, vivecon); viral maturation inhibitors; agents targeting the expression of HIV genes; agents targeting key host cell genes and gene products involved in HIV replication; and other anti-HIV agents; iRNA agents; antisense RNA; vectors expressing iRNA agents or antisense RNA; PNA and antiviral antibodies; and combinations thereof.

The antiviral agents can be used individually or in combination. Use of antiviral agents in combination is known as anti-retroviral therapy (ART), combination anti-retroviral therapy (cART) or highly active anti-retroviral therapy (HAART). Anti-retroviral (ARV) drugs are broadly classified by the phase of the retrovirus life-cycle that the drug inhibits. Typical combinations include 2 NRTIs as a "backbone" along with 1 NNRTI, PI or INSTI as a "base". In certain embodiments combinations of antiviral agents are used, such as Combivir, Trizivir, Kaletra, Epzicom, Truvada, Atripla, Complera, Stribild, Triumeq.

Methods of Treatment and Sustained Virologic Remission of HIV Infection

The present disclosure is also directed to methods for the treatment, prevention, and functional cure of HIV infection. In certain embodiments, the formulations contain antibodies directed against CD4.

In a further aspect, the antibody disclosed herein, optionally provided in pharmaceutically acceptable carrier, can be employed for the treatment, prevention, and/or functional cure of HIV infection in a subject, as well as prevention of HIV transmission.

The term "treatment" of HIV infection refers to effective inhibition of the HIV infection so as to delay the onset, slow down the progression, reduce viral load, and/or ameliorate the symptoms caused by HIV infection. Treatment include both pre- and post-exposure to HIV.

The term "prevention" of HIV infection means the onset of HIV infection is delayed, and/or the incidence or likelihood of HIV infection is reduced or eliminated. The term "prevention" of HIV transmission means the incidence or likelihood of HIV being transmitted from one individual to another (e.g., from an HIV-positive woman to the child during pregnancy, labor or delivery, or breastfeeding) is reduced or eliminated.

The term "subject" refers to any primate subject, including human, rhesus, baboon, and chimpanzee subjects.

To treat and/or prevent HIV infection, a therapeutic amount of an antibody disclosed herein is administered to a subject in need.

The term "therapeutically effective amount" means the dosage required to effect an inhibition of HIV infection so as to treat and/or prevent HIV infection. The dosage of an antibody depends on the disease state and other clinical factors, such as weight and condition of the subject, the subject's response to the therapy, the type of formulations and the route of administration. The precise dosage to be therapeutically effective and non-detrimental can be determined by those skilled in the art.

Generally, a suitable dose of an antibody for the administration to adult humans is in the range of about 3 to 50 mg/kg of the subject's body weight, with the typical initial range used being in the range of about 5 to 25 mg/kg of the subject's body weight. Suitable dosages also include about 5.0 mg/kg, about 10.0 mg/kg, or about 25.0 mg/kg of the patient's body weight.

The therapeutic compositions containing a human monoclonal antibody of this invention are conventionally administered intravenously, as by injection of a unit dose, for example. A unit dose generally refers to a therapeutic composition of the present invention which further refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The method for the treatment, prevention, and/or functional cure of HIV infection in a subject includes administering to the subject an effective amount of a formulation containing the antibody. In certain embodiments, the formulation is provided to the subject in a single administration. In other embodiments, the formulation is provided to the subject in multiple administrations. When the formulation is provided in multiple administrations, the formulation can be administered once per day, once a week, bi-weekly (every other week), or once a month. In a specific embodiment, when the treatment schedule is once a week, the formulation is administered to the subject in a dosage of about 5.0 mg/kg of the subject's body weight. In another embodiment, when the treatment schedule is bi-weekly, the formulation is administered to the subject in a dosage of about 25.0 mg/kg of the subject's body weight.

In certain embodiments, formulations containing the monoclonal antibody show high safety factor and was well tolerated when subjects were given repeatedly on a weekly basis at 5 mg/kg or 25 mg/kg for a total of 8 weeks. In specific embodiments, the monoclonal antibody can be given to subjects within hours of HIV infection at 5 mg/kg to provide sterilizing cure of HIV infection. In other embodiments, the monoclonal antibody can be given to a subject within days after HIV infection at 5 mg/kg to provide a functional cure of HIV infection.

In certain embodiments, the present invention relates to pharmaceutical compositions comprising monoclonal human, humanized or chimeric, anti-CD4 antibodies with the above described binding characteristics that can be administered to HIV patients through intravenous (IV), intramuscular (IM) or subcutaneous (SC) route as an immunotherapy for reduction of viral load. In specific embodiments, the present invention relates to pharmaceutical compositions comprising human, humanized or chimeric, monoclonal anti-CD4 antibodies, with the above described binding characteristics which exhibit competitive HIV entry inhibition as well as activation of CD4+ T cells, as an immunotherapy in patients with HIV infection.

In other certain embodiments, the present invention relates to pharmaceutical compositions comprising monoclonal human, humanized or chimeric, anti-CD4 antibodies with the above described binding characteristics that can be administered to HIV patients through IV, IM or SC route as an immunotherapy for reduction of viral load at a dose of about 10 mg/kg or higher on a weekly or biweekly schedule.

In another embodiment, the present invention relates to pharmaceutical compositions comprising monoclonal human, humanized or chimeric, anti-CD4 antibodies with the above described binding characteristics that serve as a monotherapy that can reduce viral load down to non-detectable level in treated subjects at a serum antibody level higher than 10 µg/mL.

In another embodiment, the present invention relates to pharmaceutical compositions comprising monoclonal human, humanized or chimeric, anti-CD4 antibodies with the above described binding characteristics that serve as a monotherapy that can reduce viral load down to non-detectable level in treated subjects at a serum antibody level higher than 10 µg/mL and maintained stable CD4 T cell counts during a 12-weeks treatment period.

In another embodiment, the present invention relates to pharmaceutical compositions comprising monoclonal human, humanized or chimeric) anti-CD4 antibodies with the above described binding characteristics that when given, at a dose of about 10 mg/kg or higher on a weekly or biweekly schedule, as a monotherapy, such treatment can reduce viral load down to non-detectable level in treated subjects during a 12-weeks treatment period.

In another embodiment, the present invention relates to pharmaceutical compositions comprising monoclonal human, humanized or chimeric, anti-CD4 antibodies with the above described binding characteristics that when given, at a dose of about 10 mg/kg or higher on a weekly or biweekly schedule, as a monotherapy, such treatment can reduce viral load down to non-detectable level in treated subjects with no viral load rebound as long the serum antibody level is higher than 10 µg/mL.

In another embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to treatment naïve HIV patients, will lead to functional cure of the patients.

In another embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to patients with stabilized viral load under HAART, will lead to functional cure of the patients.

In another embodiment, the present invention relates to pharmaceutical compositions comprising a monoclonal humanized anti-CD4 antibody with the above described binding characteristics that can be administered, in either IV, IM or SC route, as the key ingredient in an HAART replacement therapy, whereby each treatment cycle begins with anti-CD4 antibody treatment for 2 to 4 months as a treatment holiday for patients experiencing stabilized undetectable viral load under HAART followed by HAART treatment over one to four or more cycles leading to functional cure.

In another embodiment, the present invention relates to pharmaceutical compositions comprising a monoclonal humanized anti-CD4 antibody with the above described binding characteristics that can be administered, in either IV, IM or SC route, as the key ingredient in an HAART replacement therapy, whereby each treatment cycle begins with anti-CD4 antibody treatment for 2 to 4 months for treatment naïve HIV patients followed by 2 to 4 months of HAART treatment over one to four or more cycles leading to functional cure.

In another embodiment, the present invention relates to pharmaceutical compositions comprising a monoclonal humanized anti-CD4 antibody with the above described binding characteristics that can be administered, in either IV, IM or SC route, as the key ingredient in an HAART replacement therapy, whereby each treatment cycle begins with anti-CD4 antibody treatment for 2 to 4 months as a treatment holiday for patients experiencing stabilized undetectable viral load under HAART followed by HAART treatment over one to four or more cycles at a dose of about 5 mg/kg or higher on a weekly or biweekly schedule, leading to functional cure.

In another embodiment, the present invention relates to pharmaceutical compositions comprising a monoclonal humanized anti-CD4 antibody with the above described binding characteristics that can be administered, in either IV, IM or SC route, as the key ingredient in an HAART replacement therapy, whereby each treatment cycle begins with anti-CD4 antibody treatment for 2 to 4 months for treatment naïve HIV patients followed by 2 to 4 months of HAART treatment over one to four or more cycles at a dose of about 5 mg/kg or higher on a weekly or biweekly schedule, leading to functional cure.

In another embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to treatment naïve HIV patients, will lead to functional cure of the patients.

In another embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to patients with stabilized viral load under HAART, will lead to functional cure of the patients.

In another embodiment, the present invention relates to pharmaceutical compositions comprising a monoclonal humanized anti-CD4 antibody with the above described binding characteristics that can be administered in either IV, IM or SC route, to patients who failed HAART treatment in an adjunct therapy to HAART at a dose of about 10 mg/kg or higher on a weekly or biweekly schedule, leading to further viral reduction.

In another embodiment, the present invention relates to pharmaceutical compositions comprising a monoclonal humanized anti-CD4 antibody with the above described binding characteristics that can be administered, in either IV, IM or SC route, as the key ingredient in an adjunct therapy with HAART, in an intermittent mode beginning with a treatment period for 2 to 4 months and a treatment holiday for 1 to 2 months per cycle over one to four or more cycles, to treatment naïve HIV patients as an adjunct therapy in an intensive HAART treatment mode, leading to functional cure of the patients.

In another embodiment, the present invention relates to pharmaceutical compositions comprising a monoclonal humanized anti-CD4 antibody with the above described binding characteristics that can be administered, in either IV, IM or SC route, as the key ingredient in an adjunct therapy with HAART, in an intermittent mode beginning with a treatment period for 2 to 4 months and a treatment holiday for 1 to 2 months per cycle over one to four or more cycles, at a dose of about 5 mg/kg or higher on a weekly or biweekly schedule, to treatment naïve HIV patients as an adjunct therapy in an intensive HAART treatment mode, leading to functional cure of the patients.

In another embodiment, the present invention relates to pharmaceutical compositions comprising a monoclonal humanized anti-CD4 antibody with the above described binding characteristics that can be administered, in either IV, IM or SC route, as the key ingredient in an adjunct therapy with HAART, in an intermittent mode beginning with a treatment period for 2 to 4 months and a treatment holiday for 1 to 2 months per cycle over one to four or more cycles, at a dose of about 5 mg/kg or higher on a weekly or biweekly schedule, to patients experiencing stabilized undetectable viral load under HAART, as an adjunct therapy in an intensive HAART treatment mode, leading to functional cure of the patients.

In another embodiment, the present invention relates to pharmaceutical compositions comprising monoclonal human, humanized or chimeric, anti-CD4 antibodies with the above described binding characteristics that can be administered to HIV patients through IV, IM or SC route as an immunotherapy for reduction of viral load.

In another embodiment, the present invention relates to pharmaceutical compositions comprising monoclonal human, humanized, or chimeric anti-CD4 antibodies with the above described binding characteristics that can be administered to HIV patients through IV, IM or SC route as an immunotherapy for reduction of viral load at a dose of about 5 mg/kg or higher on a weekly or biweekly schedule.

Specific Embodiments (1) An antibody directed against a CD4 molecule, wherein
the antibody specifically binds to an extracellular region of the CD4 molecule, and wherein
when the antibody is bound to the CD4 molecule on the surface of a CD4+ cell, the antibody:
a) competitively inhibits HIV entry into the CD4+ cell;
b) activates latent HIV reservoirs in a resting CD4+ cell infected with HIV;
d) reduces levels of cellular HIV DNA; and
e) provides sustained virologic remission of HIV infection without viral load rebound.

(2) The antibody according to (1), wherein the antibody competitively inhibits cell-free and cell-to-cell transmission of HIV.

(3) The antibody according to (1), wherein the antibody reduces the percentage of regulatory T cells when administered to a subject.

(4) The antibody according to (1), wherein the antibody increases the amount of CD8+ cells when administered to a subject.

(5) The antibody according to (1), wherein the antibody increases CD8+ proliferating cells in response to HIV gag motif peptide stimulation when administered to a subject.

(6) The antibody according to (1), wherein the antibody enhances functional HIV specific CD8+ CTL cells that target an HIV infected CD4+ cell when administered to a subject.

(7) The antibody according to (1), wherein the antibody enhances TNF-alpha production in CD4+ cell.

(8) The antibody according to (1) wherein the antibody activates a resting CD4+ cells with or without crosslinking.

(9) The antibody according to (1), wherein the antibody reduces HIV viral load in an HIV positive patient to less than 50 copies per milliliter of blood without viral load rebound.

(10) The antibody of (1), wherein the antibody binds to a region around domain 1 of the CD4 molecule.

(11) The antibody of (1), wherein the antibody binds to a region around the CDR2 region in domain 1 of CD4.

(12) The antibody of (1), wherein the antibody comprises
a heavy chain variable region amino acid sequence comprising:
CDR1 of SEQ ID NO: 1,
CDR2 of SEQ ID NO: 2, and
CDR3 of SEQ ID NO: 3; and
a light chain variable region amino acid sequence comprising:
CDR1 of SEQ ID NO: 4,
CDR2 of SEQ ID NO: 5, and
CDR3 of SEQ ID NO: 6.

(13) The antibody of (1), wherein the antibody is a monoclonal antibody.

(14) The antibody of (1), wherein the antibody is a humanized monoclonal antibody.

(15) The antibody of (1), wherein the antibody is a humanized monoclonal antibody comprising:
a heavy chain variable region comprising an amino acid sequence of SEQ ID NO: 11; and
a light chain variable region comprising an amino acid sequence of SEQ ID NO: 13.

(16) The antibody of (1), wherein the antibody is a humanized monoclonal antibody comprising:
a heavy chain comprising an amino acid sequence of SEQ ID NO: 10; and
a light chain comprising an amino acid sequence of SEQ ID NO: 8.

(17) The antibody of (1), wherein the antibody is a humanized monoclonal antibody comprising:
a heavy chain comprising an amino acid sequence of SEQ ID NO: 9; and
a light chain comprising an amino acid sequence of SEQ ID NO: 8.

(18) The antibody of (1), wherein the antibody is a humanized monoclonal antibody comprising:
a heavy chain comprising an amino acid sequence of SEQ ID NO: 7; and
a light chain comprising an amino acid sequence of SEQ ID NO: 8.

(19) The antibody of (1) having an absolute binding affinity (Kd) to membrane-bound CD4 on HPB-ALL cells between about $3.1 \times 10^{-11}$ M to about $8.1 \times 10^{-11}$ M.

(20) The antibody of (1) bound to a CD4 molecule.

(21) A composition comprising the antibody of (1).

(22) A pharmaceutical composition comprising the antibody of (1) and a pharmaceutically acceptable carrier.

(23) A pharmaceutical composition comprising the antibody of (1) in phosphate buffer saline (PBS), 20 mM glycine, and 0.05% (v/v) polysorbate 20.

(24) A pharmaceutical composition comprising the antibody of (1) in phosphate buffer saline (PBS), 20 mM glycine, 0.05% (v/v) polysorbate 20, and 10 mM histidine.

(25) A pharmaceutical composition comprising about 1.0 mg/mL to about 200.0 mg/mL of the antibody of (1) in phosphate buffer saline (PBS), 20 mM glycine, and 0.05% (v/v) polysorbate 20.
(26) A pharmaceutical composition comprising about 1.0 mg/mL to about 200.0 mg/mL of the antibody of (1) in phosphate buffer saline (PBS), 20 mM glycine, 0.05% (v/v) polysorbate 20, and 10 mM histidine.
(27) A pharmaceutical composition comprising about 10.0 mg/mL of the antibody of (1) in phosphate buffer saline (PBS), 20 mM glycine, and 0.05% (v/v) polysorbate 20.
(28) A pharmaceutical composition comprising about 10.0 mg/mL of the antibody of (1) in phosphate buffer saline (PBS), 20 mM glycine, 0.05% (v/v) polysorbate 20, and 10 mM histidine.
(29) A pharmaceutical composition comprising the antibody of (12) and a pharmaceutically acceptable carrier.
(30) A pharmaceutical composition comprising the antibody of (16) and a pharmaceutically acceptable carrier.
(31) A method for treating a subject exposed to HIV comprising:
administering to the subject a pharmacologically effective amount of the antibody of (1).
(32) The method of (31), wherein the antibody is administered to the subject prior to exposure to HIV.
(33) The method according to (31), wherein the antibody is administered to the subject after exposure to HIV.
(34) The method according to (31), wherein the antibody is administered within 48 hours after exposure to HIV.
(35) The method according to (31), wherein the antibody is administered to the subject at a dosage of at least about 5 mg/kg body weight.
(36) The method according to (35), wherein the antibody is administered to the subject multiple times.
(37) The method according to (36), wherein the antibody is administered to the subject in a weekly, bi-weekly, or monthly interval.
(38) The method according to (36), further comprising a step of administering an antiviral agent to the subject.
(39) The method according to (38), wherein the antiviral agent is a highly active antiretroviral therapy (HAART).
(40) The method according to (39), wherein HAART comprises a nucleoside analogue reverse transcriptase inhibitor in combination with a protease inhibitor or a non-nucleoside reverse transcriptase inhibitor.
(41) The method according to (39), wherein the antibody is administered concurrently with HAART.
(42) The method according to (39), wherein the antibody and HAART are administered to the subject over the course of a cycle, wherein the cycle comprises:
  i) administering the antibody to the subject for a first period of time followed by a treatment holiday for a second period of time; and
  ii) administering HAART to the subject continuously during the first period of time and the second period of time in (i).
(43) The method according to (39), wherein the antibody and HAART are administered to the subject over the course of a cycle, wherein the cycle comprises:
  i) administering the antibody to the subject for a period of four months in a weekly, bi-weekly, or monthly interval followed by a two month treatment holiday; and
  ii) administering HAART to the subject continuously during the six-month period in (i).
(44) The method according to (42), wherein the subject is treated over the course of two cycles.
(45) The method according to (43), wherein the subject is treated over the course of two cycles.
(46) The method according to (39), wherein the antibody is administered at a time that is not concurrent with HAART.
(47) The method according to (39), wherein the antibody and HAART are administered to the subject over the course of a cycle, wherein the cycle comprises:
  i) administering the antibody to the subject for a first period of time followed by a treatment holiday for a second period of time; and
  ii) administering HAART to the subject during the second period of time and not during the first period of time.
(48) The method according to (47), wherein the antibody is administered in regular intervals during the first time period.
(49) The method according to (47), wherein the antibody is administered in weekly, bi-weekly, or monthly intervals during the first time period.
(50) A method for treating a subject with HIV infection, comprising administering to the subject a treatment regimen comprising:
  a) a pharmacologically effective amount of the antibody of (1); and
  b) a highly active antiretroviral therapy (HAART).
(51) The method of (50), wherein the antibody is administered to the subject at a dosage of at least about 5 mg/kg body weight.
(52) The method according to (50), wherein the antibody and HAART are administered to the subject over the course of a cycle, wherein the cycle comprises:
  i) administering the antibody to the subject for a first period of time followed by a treatment holiday for a second period of time; and
  ii) administering HAART to the subject continuously during the first period of time and the second period of time in (i).
(53) The method according to (50), wherein the antibody and HAART are administered to the subject over the course of a cycle, wherein the cycle comprises:
  i) administering the antibody to the subject for a period of four months in a weekly, bi-weekly, or monthly interval followed by a two-month treatment holiday; and
  ii) administering HAART to the subject continuously during the six-month period in (i).
(54) The method according to (52), wherein the subject is treated over the course of two or more cycles.
(55) The method according to (53), wherein the subject is treated over the course of two or more cycles.
(56) The method according to (53), wherein the antibody and HAART are administered to the subject over the course of a cycle, wherein the cycle comprises:
  i) administering the antibody to the subject for a period of four months in a weekly, bi-weekly, or monthly interval followed by a two-month treatment holiday; and
  ii) administering HAART to the subject continuously during the six-month period in (i).
(57) The method according to (50), wherein the antibody in (a) is administered at a time that is not concurrent with HAART in (b).
(58) The method according to (50), wherein the antibody in (a) and HAART in (b) are administered to the subject over the course of a cycle, wherein the cycle comprises:
  i) administering the antibody to the subject for a first period of time followed by a treatment holiday for a second period of time; and
  ii) administering HAART to the subject during the second period of time and not during the first period of time.

(59) The method according to (58), wherein the antibody is administered in regular intervals during the first time period.
(60) The method according to (58), wherein the antibody is administered in weekly, bi-weekly, or monthly intervals during the first time period.
(61) A method for inhibiting HIV entry into a CD4+ cell, comprising
exposing the antibody of (1) to the cell.
(62) A method for inhibiting gp120 binding to a CD4+ cell, comprising
exposing the antibody of (1) to the cell.
(63) A method for activating a resting CD4+ T cell, comprising
exposing the antibody of (1) to the cell.
(64) A method for activating a latent reservoir of HIV in a resting T cell, comprising
exposing the antibody of (1) to the cell.
(65) A method for reducing latent HIV reservoirs in a sample of cells infected with HIV, comprising
a) exposing the antibody of (1) to the sample of cells; and
b) exposing HAART to the sample of cells.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all amino acid sizes, and all molecular weight or molecular mass values, given for polypeptides are approximate, and are provided for description. Although methods and materials similar or equivalent to those described herein can be used in the practice or testing of the disclosed method, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

The following illustrative explanations of the figures and related examples are provided to facilitate understanding of certain terms used frequently herein, particularly in the examples. The explanations are provided as a convenience and are not limitative of the invention.

Example 1

Immunological and Functional Properties of MAB B4

Monoclonal antibody B4 (mAb B4) or M2 (mAb M2) is a monoclonal antibody that recognizes a complex HIV receptor site on the T cell surface (CD4). MAb B4 or M2 can influence and interfere with CD4's interaction with HIV co-receptors. MAb B4 or M2 preferentially neutralized primary HIV-1 isolates (both antibodies were discussed in further detail in U.S. Pat. Nos. 5,912,176, 6,090,388).

The information below summarizes the discovery and preliminary characterization studies of murine mAb B4 including data excerpted from two US patents (U.S. Pat. Nos. 5,912,176 and 6,090,388 by Wang) and the journal article by Wang et al., 1999, all of which are incorporated by reference in their entireties.

1. Murine Monoclonal Antibodies Derived from Immunization with HPB ALL Cells or Purified PBL T Cells MAb B4 was obtained by immunizing BALB/c mice with intact, uninfected CD4+ human HPB-ALL cells, a T-acute lymphoblastic leukemia cell line.

MAb M2 was obtained by immunizing BALB/c mice with intact, uninfected CD4+ cells isolated from PBL.

A novel class of anti-CD4 antibodies, represented by mAb B4 or M2, were obtained having specificity for CD4 on the cell surface and with broad neutralizing activity against primary isolates of HIV-1. In the subsequence discussion and examples, only Mab B4 will be further illustrated and discussed for purpose of focusing on important property disclosure.

2. Characterization of the mAb B4 Recognition Site

MAb B4 has been found to preferentially recognize membrane-bound CD4 on the surface of cells compared to recombinant soluble CD4 (rsCD4).

MAb B4 binding to membrane-bound CD4 prior to exposure of HIV has been shown to block subsequent attachment of gp120 and whole virus to CD4. However, membrane-bound CD4 that has been bound to gp120 prior to exposure to the antibody can still bind mAb B4. Thus, mAb B4 can affect the binding of gp120 to membrane-bound CD4, but gp120 does not affect the binding of mAb B4 to CD4.

3. In Vitro Neutralization Activity of mAb B4

Murine mAb B4 is not, by common definition, a neutralizing antibody. Instead, mAb B4 inhibits viral entry by coating the host cell receptor rather than by attaching to the virus. MAb B4's effect on HIV infection can be readily observed by viral neutralization assays used in the field (e.g., MT-2 Microplaque Neutralization Assay (Sawyer et al., 1994)). The neutralization activity of murine mAb B4 was evaluated by our collaborator Dr. Carl Hanson (California Department of Health Services) and was also independently evaluated in the laboratories of Dr. John Mascola, (Henry Jackson Foundation, WRAIR), Dr. David Montefiori (Duke University) and Dr. Malcolm Martin (NIAID). The following HIV neutralizing features, extensively characterized from 1995 to 2010, are associated with mAb B4:

1. PBMC-grown primary isolates are more sensitive to neutralization by mAb B4 than T cell line-adapted isolates HIV-1$_{IIIB}$ and HIV-1$_{MN}$.
2. mAb B4 neutralizes infection by primary isolates of co-receptor usage CCR5/CXCR4 (dual) and CCR5.
3. mAb B4 has low activity against T cell line-adapted HIV-1 isolates of CXCR4 co-receptor usage.
4. mAb B4 neutralizes a diverse range of Syncytial Inducing (SI) and Non-Syncytial Inducing (NSI) primary isolates representing HIV-1 subtypes A-G, to 90% endpoints and up to 3 logs of infectivity.
5. mAb B4 neutralizes HIV-2, SIV, and SHIV having a dual co-receptor HIV-1 envelope.
6. In the tonsil histoculture system, mAb B4 reduces the infectivity of HIV-1 primary isolate VL135 (HIV-1$_{VL135}$) by two logs. As little as 12.5 µg/mL of mAb B4 completely neutralizes>100 TID$_{50}$ (50% tonsil infectious doses) of the monocytotropic isolate JR-CSF in the presence of active human complement, which is a condition under which many anti-viral antibodies show antibody-dependent enhancement.
7. mAb B4 exerts neutralizing activity on HIV-1$_{VL135}$ when added up to 48 hours post-infection, with significant anti-viral effect when added up to 72 hours later.
   a. it is equally effective whether pre-incubated with cells or virus.

b. it acts by blocking foci of infection from spreading to new cells rather than by a post-entry mechanism.

c. in these assays, mAb B4 did not contribute to cytotoxicity.

Example 2

HIV-1 Neutralization and Resistance Assays

The following viral neutralization and resistance assays were performed at the laboratories of Dr. Carl Hanson and Monogram Biosciences, Inc. for multiple HIV isolates of various clades during the period 1998 to 2011. Detailed descriptions of the assays are described below.

1. HIV-1 Neutralization Assays.

Blood or antibody samples were collected as indicated in each of the studies. Serum or antibody samples were evaluated on a multi-clade panel of HIV-1 isolates using either MT-2 microplaque assay or mitogen (PHA)-stimulated PBMC assay.

1.1. MT-2 Microplaque Assay

The MT-2 microplaque assay was limited to syncytium-inducing isolates of HIV. The assay was performed in 96-well plates, in which up to 25 small plaques per well could be enumerated by fluorescence staining of the syncytia on the microplaques. In this assay, infected MT-2 cells formed into monolayers by centrifugation through molten agarose, which gels during centrifugation. The assay was found to be sensitive and has a dynamic range extending over many orders of magnitude. The assay has also been found to be uniquely efficient for processing large number of specimens. The use of computerized statistical analysis, made possible by the large number of replicate wells, was found to provide a degree of quality control and standardization that has been difficult to achieve using other formats.

1.2 the PBMC Assay

The PBMC assay is a standard antigen-reduction assay in which expression of p24 antigen in PBMCs is quantified by antigen-capture ELISA following growth of infected cells in 96-well microtiter plates. An advantage of this assay is its applicability to all HIV strains and isolates.

1.3 Virus Stocks.

HIV-1 stocks for neutralization, ex vivo and in vivo studies are listed in Tables 3, 5, and 6 as well as in FIGS. 1a, 1b, 3, 22 and 23. Primary HIV-1 viruses from subtypes A to G and H were: (a) isolated from homosexual men participating in the San Francisco Men's Health Study of the California Department of Health Services, Viral and Rickettsial Disease Laboratory, VRDL; (b) acquired from the World Health Organization Network for HIV Isolation and Characterization, (c) supplied by the U.S. Military HIV Research Program, and (d) as gifts from National Institute of Allergy and Infectious Diseases AIDS Research and Reference Reagent Program. DH-12, a patient isolate passaged in chimpanzee peripheral blood mononuclear cells (PBMCs) was also supplied by the National Institute of Allergy and Infectious Diseases AIDS Research and Reference Reagent Program.

1.4. B4 or dB4 Neutralizing Activity

B4 or dB4 neutralizing activity was defined as the antibody concentration that provided the indicated percentage of reduction (50-95%) in virus when compared to controls containing no antibody. Antibody concentrations for the 50% and 90% endpoints were derived by interpolation between antibody dilutions.

2. The PhenoSense HIV Entry Assay

The PhenoSense HIV Entry Assay for determination of drug resistance was performed at Monogram Biosciences, Inc. (South San Francisco, Calif.).

Recombinant virus generated from vector pools was used to infect cells in the presence of varying concentrations of a drug or antibody (e.g. B4 or dB4). The amount of drug needed to inhibit viral replication of the test vector by 50% ($IC_{50}$) or 90% ($IC_{90}$) was determined.

2.1 Generation of Recombinant Viruses Used in the PhenoSense HIV Assay

Recombinant viruses used in the PhenoSense HIV Assay were generated from samples collected from patients screened in longitudinal studies of HIV infection and identified as HIV seropositive. For individuals with incident HIV infection, clinical and plasma samples were collected for laboratory assessment including HIV viral load and CD4 cell counts. For individuals who were initially seronegative, but became seropositive after approximately 1 year of follow-up, HIV infection was confirmed by two enzyme immunoassays with western blot confirmation.

Samples from participants who had subtype A, BF, C, D, E, EA, F, G, or J at the time of seroconversion (based on previous HIV subtyping using a multiple hybridization assay) were collected for construction of recombinant viruses, as shown in Table 3. The HIV env, pol regions were amplified from a test sample and the amplified DNAs were cloned into a test vector. In the GeneSeq HIV, vector pools were sequenced to determine the HIV genotype. In the PhenoSense HIV assay, recombinant virus generated from the vector pools was used to infect cells in the presence of varying concentrations of a drug.

Example 3

Neutralizing Activities of MAB B4 by Monogram Bioscience Phenosense Assay Against HIV Isolates of all Clades It has been well documented that mAb B4 neutralizes all HIV viruses of the B clade. In one study a total of 73 representative non-B clade HIV isolates from clades A (n=8), BF (n=1), C (n=18), D (n=18), E (n=4), EA (n=10), F (n=8), G (n=4), J (N=2), plus three control viruses 92HT594, JRCSF, JRFL were made into recombinant viruses and tested in a PhenoSense HIV assay for their sensitivity to mAb B4 (Table 3). It was found that all of the recombinant viruses were highly sensitive to mAb B4 with an unprecedented low $IC_{50}$ and $IC_{90}$ concentrations, with an average $IC_{50}$=0.018 µg/mL and $IC_{90}$=0.062 µg/mL. It was noteworthy to find that many of these HIV isolates were derived from multi-drug resistant patients, a clear indication that mAb B4 or its human counterpart would be highly efficient in treating patients who are already HIV drug resistant.

Example 4

Monoclonal Antibody B4 Mediates Competitive HIV Entry Inhibition: An Unexpected Feature which Predicts the Prevention of HIV Resistant Mutants Upon Treatment Competitive inhibition studies can evaluate the ability and efficacy of an inhibitor (e.g., entry inhibitor antibody) to compete with HIV envelope proteins for the same receptor binding site on CD4, thereby, inhibiting entry of HIV into the cell. In a theoretical study, mAb B4 competes with HIV envelope protein (gp120) for binding of CD4. FIG. 1A shows the predicted results of this study, where each line represents a different viral isolate. Specifically, the expected results from this theoretical study demonstrate that, although different viral isolates would have different sensitivities ($IC_{50}$) to mAb B4, entry of all viral isolates would be inhibited by 100% as long as mAb B4 was present in a sufficient concentration.

Figure 2A:
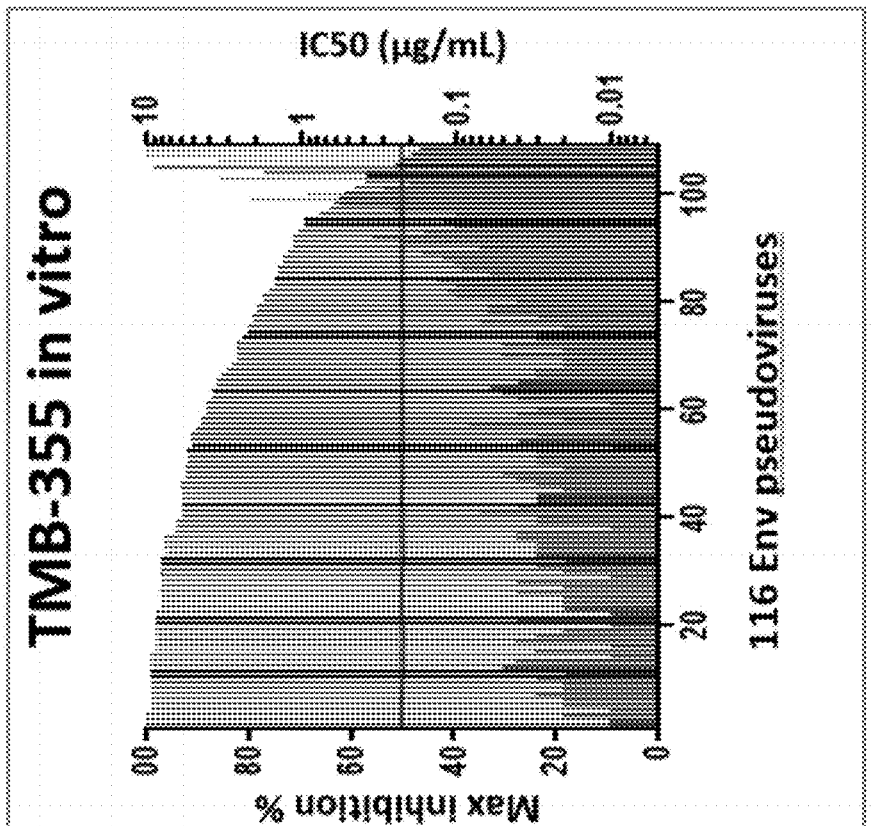
FIG. 2A. A graph illustrating a non-competitive HIV entry inhibition mechanism. The graph shows theoretical results obtained in a non-competitive HIV entry inhibition model, where HIV and an inhibitor bind to different sites on the same target molecule (e.g. domain 2 of CD4 for TMB-355). In this non-competitive inhibition model, HIV binding/entry can be reduced by the inhibitor, but complete inhibition is not achieved regardless of the concentration of the inhibitor. Resistance of HIV to the antibody drug is reflected as a "plateau" in % inhibition regardless of drug concentration.

By comparison, noncompetitive inhibition studies can evaluate the ability and efficacy of an inhibitor (e.g., co-receptor antagonist or antibody that binds to a different portion of CD4) to inhibit or reduce the ability of HIV envelope proteins to bind to CD4, thereby, inhibiting entry of HIV into the cell. In a theoretical study, the ability of a noncompetitive inhibitor (e.g., TMB-355) to inhibit HIV envelope protein (gp120) from binding CD4 is analyzed. FIG. 2A shows the predicted results of this study, where each line represents a different viral isolate. Specifically, the expected results from this theoretical study demonstrate that different viral isolates would have different sensitivities ($IC_{50}$) to TMB-355 and at least some portion of the viral isolates would enter the cell regardless of the amount of TMB-355 present. Based on this theoretical study, it would be expected that HIV resistance would be observed as a "plateau" in maximal percent inhibition regardless of $IC_{50}$.

TMB-355 (formerly TNX-355, also called Ibalizumab) is a humanized IgG4 monoclonal antibody that was designed to bind to extracellular domain 2 of rhesus and human CD4 to prevent post-binding entry of HIV into CD4+ cells (e.g., Burkly, L C, et al., 1992; and Kurizkes, D R, et al., 2004). The TMB-355 antibody binding site on CD4 is distinct from the site required for the binding of HIV-1 envelope gp120 and is distinct from the site needed for interaction with major histocompatibility complex proteins. Accordingly, TMB-355 mediates non-competitive HIV entry inhibition.

Figure 2B:
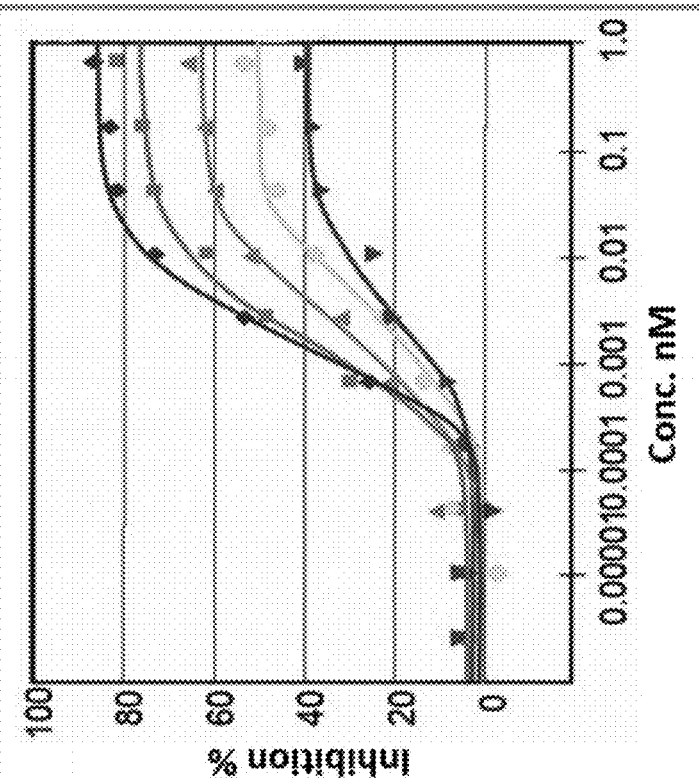
FIG. 2B. HIV-1 entry inhibition results from a panel of 118 diverse HIV-1 Env pseudovirus strains covering 11 clades using TMB-355 (Pace, G., et al., 2011). For each virus, black lines indicate maximum percent inhibition (MPI) when treated at TMB-355 concentrations up to 10 μg/mL (left Y axis); and grey lines indicate the corresponding $IC_{50}$ (right Y axis). TMB-355 neutralized 92% of the viral strains with ≥50% inhibition and only neutralized 31% of the viral strains with ≥95% inhibition.

TMB-355 has been shown to have a strong neutralization activity against some HIV-1 viruses but its inhibitory activity is inconsistent when a broad panel of HIV strains is evaluated. FIG. 2B shows that the MPI of TMB-355 ranges between 100% to 15% (left Y axis), coupled with an increasing $IC_{50}$ from 0.01 µg/mL to 10 µg/mL (right Y axis), against a panel of 118 Env pseudotype HIV viruses with each bar representing one virus isolate (Song, R., et al., 2013). Of all clades analyzed, clade A and E viruses were significantly more susceptible to TMB-355 than non-clade A and E viruses. In addition, viral resistant mutants were found with mutations identified in the V5 region of gp120 from patients receiving TMB-355 treatment for viral load reduction (Toma, J., et al., 2011; Pace, C. S., et al., 2013). The non-competitive inhibitory effect demonstrated by TMB-355 (Ibalizumab) suggests that there would be a high likelihood for development of resistant HIV mutants during the antibody treatment period because viral replication will take place for isolates that have less than 100% inhibition.

In contrast, data collected over a 10 year period from a panel of over 850 Env pseudotype HIV viruses shows that mAb B4 offers an unexpected breadth and potency in HIV entry inhibition (FIG. 1B). From this collection of data, it can be seen that mAb B4 has nearly 100% MPI with an $IC_{50}$ clustered around two concentrations, one between 0.01 to 1 µg/mL, and the other around 10 µg/mL. The HIV entry inhibition profile for mAb B4 has the typical characteristics of a competitive inhibition mechanism with an MPI for each of the HIV viruses at ~100% regardless of $IC_{50}$. In view of mAb B4's notably strong competitive HIV entry inhibition characteristics, viral resistant mutants are unlikely to develop during the mAb B4 treatment period. Such tight competitive inhibition, as exerted by mAb B4, has never been observed with any other HIV inhibitor tested thus far.

The MPI and $IC_{50}$ data from this Example, combined with the data showing that many of the HIV isolates derived from multi-drug resistant patients were highly sensitive to mAb B4 discussed in Example 3, suggested that mAb B4 or its human counterpart would be highly efficient in treating drug resistant HIV patients who are failing HAART treatment. The mode of neutralization mediated by mAb B4 offers a unique HIV drug that would prevent the generation of drug resistant viral mutants in HIV patients receiving treatment with mAb B4 or its human counterpart analogues carrying similar Fv regions. Competitive HIV binding inhibition is a unique property that would allow anti CD4 antibodies to exert the clinical efficacy in treatment of HIV patients as described in this invention.

Example 5

Antibody B4 Inhibits Effectively Both Cell-Free and Cell-to-Cell Transmission of HIV HIV particles classically spread throughout the body by cell-free transmission, where the virus diffuses in the blood-stream and local environment to infect cells. The virus also has the ability to transfer from infected to uninfected cells directly by a mechanism that requires intimate cell-to-cell contact. Such spread occurs when an infected cell forms a stable point of contact with an uninfected cell and transmits HIV particles directly to the uninfected cell. Cell-to-cell spread is more efficient, quicker, and does not require diffusion in the bloodstream, compared to cell-free spread.

Sigal, A., et al., 2011 reported that infections originating from cell-free virus decrease strongly in the presence of the antiretroviral drug tenofovir whereas infections involving cell-to-cell spread are markedly less sensitive to the drug in a co-culture assay. The reduction in sensitivity was sufficient to keep multiple rounds of infection from terminating in the presence of drug. The authors examined replication from cell-to-cell spread in the presence of clinical drug concentrations using a stochastic infection model and found that replication was intermittent, without substantial accumulation of mutations. If cell-to-cell spread has the same properties in vivo, it may have adverse consequences for the immune system, leading to therapy failure in individuals with risk factors, and potentially contribute to viral persistence and, hence, be a barrier to curing HIV infection.

It is therefore important to assess the ability and potency of mAb B4 and mAb dB4 related antibodies to inhibit cell-to-cell transmission of HIV for assessment of its potential effect in treatment.

1. Assay to Measure Antibody Mediated Inhibition of Cell-to-Cell Transmission of HIV 1.1 Materials and Methods 1.1.1 Cells and Viruses.

The Jurkat-inGLuc clone (NIH AIDS Research and Reagents Program) with a reporter gene luciferase engineered into HIV-1 genome was selected as donor cells due to low expression of surface CD4 to minimize donor-to-donor infection in co-culture experiments with target primary CD4+ T cells. The reporter gene luciferase can be expressed in infected cells and used as a marker for viral infection. These virally expressed reporters in the infected cells can be measured to quantify HIV-1 infection. Primary CD4 T cells were used as the target cells. Viruses UG266 and UG046 of clade D were used in the study.

1.1.2 Viral Cell-to-Cell Transmission Assay.

In this assay, donors were preincubated with the antibody B4 in serial dilutions prior to mixing with the indicated HIV-1 strains and used a few days later, when ~10-75% of the cells were Gag+. Donor and CD4 positive PBMC target cells were then mixed at a 1:2 ratio in 96-well plates at a final concentration of $1.5 \times 10^6$ cells/ml in 200 µl. After 48 hrs, cells were stained for intracellular Gag and analyzed by flow cytometry. GLuc accumulated in the culture supernatant was detected using the BioLux *Gaussia* Luciferase Assay Kit (New England Biolabs) and a Berthold Technologies luminometer.

1.1.3 Calculation of $IC_{50}$ and $IC_{90}$.

Dose-response inhibition curves were drawn by fitting data to sigmoid dose-response curves (variable slope). Percentage of inhibition was defined as (percent signal in nontreated target cells–percent signal in antibody-treated cells)/(percent signal in nontreated target cells)×100. The $IC_{50}$ and $IC_{90}$ were calculated accordingly.

2. Results and Discussion

Table 4 shows that antibody B4 was able to inhibit cell-to-cell and cell-free transmission of HIV (viral strains UG266 and UG046 of clade C) equivalently when measured by a stringent 90% entry inhibition criteria. Specifically, the fusion inhibition titers were found to be 1:140 and 1:245 for UG266 and UG046 viral strains in cell-to-cell transmission assays, which was comparable to the neutralization titers of 1:136 and 1:234 in cell-free transmission neutralization assays, respectively. Higher fusion inhibition titers for the two strains were observed for cell-to-cell transmission compared to the corresponding cell-free transmission when measured by a 50% entry inhibition criteria.

These results demonstrate that antibody B4 has an unusual property in its capability to inhibit both cell-to-cell and cell-free transmission of HIV when compared to all other neutralizing monoclonal antibodies targeting HIV Env proteins and other ART-drugs measured thus far. These results suggest that mAb B4 and mAb dB4 related antibodies are uniquely qualified to prevent cell-free and cell-to-cell spread of HIV virus in an individual.

Example 6

Antibody UB-421 (DB4C7 or DB4) Mediates Reactivation of Resting PBMCS for Enhanced Viral Replication in HIV Infected Individuals 1. Background HIV-1 infects resting peripheral blood mononuclear cells (PBMCs) but remains inactive until subsequent cell activation. An in vitro model using cell culture condition and a protocol that allows nonproductive infection of resting T cells mimicking latent HIV-1 harbored in quiescent PBMCs was used to investigate the stimulation effect of heat-inactivated HIV-1 (iHIV-1) or gp120-anti-gp120 immune complexes on these resting PBMCs (Briant, L., et al., 1996).

It was demonstrated that CD4 engagement with the envelope glycoproteins of heat-inactivated HIV-1 (iHIV-1) or gp120-anti-gp120 immune complexes was sufficient, through crosslinking, to stimulate a signal transduction pathway controlling activation of NF-kB (i.e. nuclear translocation) and AP-1 which in turn involves extracellular domain 1 (D1) and the intracytoplasmic domain of CD4 and several kinases (Lck, Raf-1, MEK and ERK) to induce cell cycle progression, promote cell-surface expression of activation marker CD25, and stimulate provirus integration and commit cells to produce virus.

A separate scientific finding by Than, et al. (Than, et al., 1997) further confirmed that crosslinking of CD4 molecules at the gp120 binding site by anti-CD4 monoclonal antibody induces latently infected PBMCs from HIV infected patients to promote virus replication. The anti-CD4 mAb used in this study was Leu3a which binds the CDR2-loop of D1 of CD4. Specifically, Leu3a is directed to a linear epitope represented by peptide with aa47-64 within domain 1 of CD4 (Chiba, Y. 1992).

Additionally, virus reactivation in resting PBMCs was found to be specifically induced by monoclonal antibodies directed against the CDR2-loop in domain 1 (D1) of CD4 and not by antibodies directed against other epitopes, such as CDR3 in D1 or the nearby D1/D2 junction region (Briant, L., et al., 1999) (FIG. 3, compare lane 4 with lanes 5 and 6). Such virus reactivation can be prevented by prior absorption of CDR2-loop ligands with soluble CD4 (sCD4) (FIG. 3, compare lane 4 and lane 8).

It was, therefore, important to assess whether antibody dB4C7 (UB-421) with high binding affinity with CD4 around domain 1 region can mediate reactivation of resting PBMCs for enhanced viral replication in HIV infected individuals.

2. Refinement of B4/dB4 Conformational Binding Site Around D1 of CD4

2.1 Competitive Sequential Binding Inhibition of Leu3a Binding to Chimp CD4 Positive PBMCs by mAb B4 but not in the Reverse Order Chimp PBMC cells isolated from two subjects (X282 and X301) were used in this study as well as mAb B4 (labeled by FITC) and Leu3a (labeled by PE). PBMCs were sequentially stained with the respective antibodies and analyzed by cytofluorography. The data obtained from this experiment is reported in Table 5 and FIG. 4 and discussed below.

Figure 4:
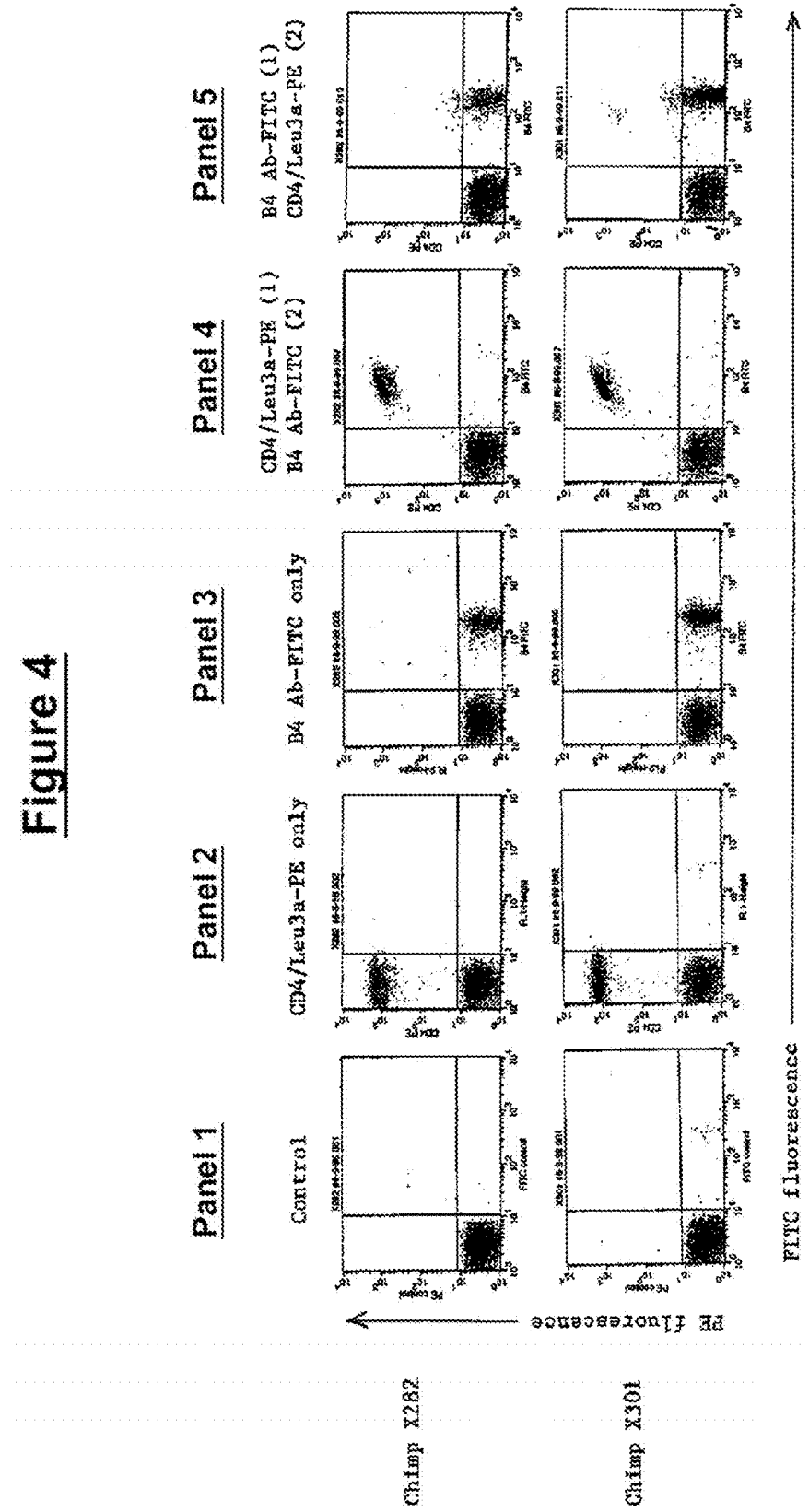
FIG. 4. Antibody B4 recognizes conformational epitopes covering CDR2 region of CD4 domain 1 bound by antibody Leu3a. Competitive binding inhibition to CD4 positive cells was found by monoclonal antibody B4 and Leu3a (directed against CDR2 region of CD4 domain 1). Chimp PBMC cells from two subjects (X282 and X301) were used for the study. Monoclonal antibody B4 was labeled by FITC. Antibody Leu3a was labeled by PE. Cytofluorograph analysis of PBMC cells indicated a positive binding by Leu3a-PE as shown in the second panel from the left (Panel 2), by antibody B4-FITC as shown in the third panel from the left (Panel 3), and a double stained population as shown in the fourth panel from the left when the PBMCs were first stained by Leu3a-PE followed by staining with antibody B4-FITC (Panel 4); whereas prior binding by antibody B4-FITC would block the sequential binding by Leu3a-PE as shown in the fifth panel from the left leaving only B4-FITC binding (Panel 5). This sequential binding inhibition study indicated a one way inhibition by antibody B4-FITC against Leu3a-PE indicating antibody B4 recognizes a larger surface contact area with CD4 positive cells around the region of CDR2 in CD4 domain 1 which is recognized by Leu3 in a shorter stretch of peptides from AA47-64 within domain 1.

In the single label control samples, cells stained with Leu3a only tested positive for Leu3a-PE binding (FIG. 4, Panel 2); and cells stained with mAb B4 only tested positive for B4-FITC binding (FIG. 4, Panel 3). Specifically, CD4+ cells (as detected by Leu3a) in non-infected chimp samples (X282 and X301) were 25.5% and 44.0% respectively, similar to those detected by mAb B4 (26.1% and 45.5%) (Table 5).

Prior binding of Leu3a followed by exposure to mAb B4 led to double stained (Leu3a+/B4+) PBMC cell counts (FIG. 4, Panel 4) similar to the single label control cells stained with Leu3a or B4 alone (i.e., 24.5% and 46.7% for X282 and X301, respectively) (Table 5).

In contrast, prior binding of mAb B4 followed by exposure to Leu3a led to only mAb B4 stained PBMCs with no Leu3a positive staining in either single or double staining procedure (FIG. 4, Panel 5; Table 5).

Collectively, these results demonstrate a one way inhibition by antibody B4-FITC against Leu3a-PE. That is, B4 binding is not blocked by prior Leu3a binding; however, Leu3a binding is blocked by prior B4 binding. These data support the conclusion that mAb B4 recognizes conformational epitopes covering the CDR2 region of CD4 domain 1 recognized by antibody Leu3a and that mAb B4 binds to this region of CD4 with a higher affinity compared to antibody Leu3a.

2.2 Competitive Inhibition by ELISA of B4 Binding to rsCD4 by Immune Sera Directed Against HIV RC Peptide (Aa39-66)

The binding affinity of mAb B4 to full-length recombinant soluble CD4 (rsCD4) was evaluated through a competitive inhibition study using immune sera directed against the CDR2 region of CD4 domain 1.

2.2.1 Anti-HIV RC Polyclonal Antibodies.

Polyclonal antibodies against the CDR2 region of CD4 domain 1 were prepared by immunizing guinea pigs with a cyclic peptide comprising aa39-66 of CD4. This cyclic peptide is referred to in this study as the HIV receptor complex peptide (HIV RC peptide) and was previously described as peptide p2240c in Wang, et al., 2002.

Specifically, guinea pig serum directed against the HIV RC peptide was obtained at the specified time points after intramuscular immunization of 4-6 week old Duncan Hartley guinea pigs with 100 µg in 0.5 ml per dose in Complete Freunds Adjuvant at week 0 and Incomplete Freunds at 3 and 6 weeks, followed by monthly boosts in Incomplete Freunds thereafter.

The polyclonal antibodies obtained are referred to as "anti-HIV RC polyclonal antibodies".

2.2.2 Competitive Inhibition of B4 Binding to rsCD4 by Anti-HIV RC Polyclonal Antibodies.

The competitive inhibition experiment was carried out using 96 well microtiter plates coated with full-length rsCD4 at 0.08 µg/mL at 0.1 mL per well. The wells were incubated with guinea pig sera collected from 0, 3, 6, 9, 12, 14, 16, and 19 weeks post immunization with immunogen directed against the HIV RC peptide (aa39-66 of CD4) at 1:30 dilutions prior to binding by biotinylated B4-antibody followed by binding with conjugated avidin-HRP as a tracer. Negative control sera (RC isotype) from unimmunized guinea pigs collected throughout the same period were tested as well.

Figure 5:
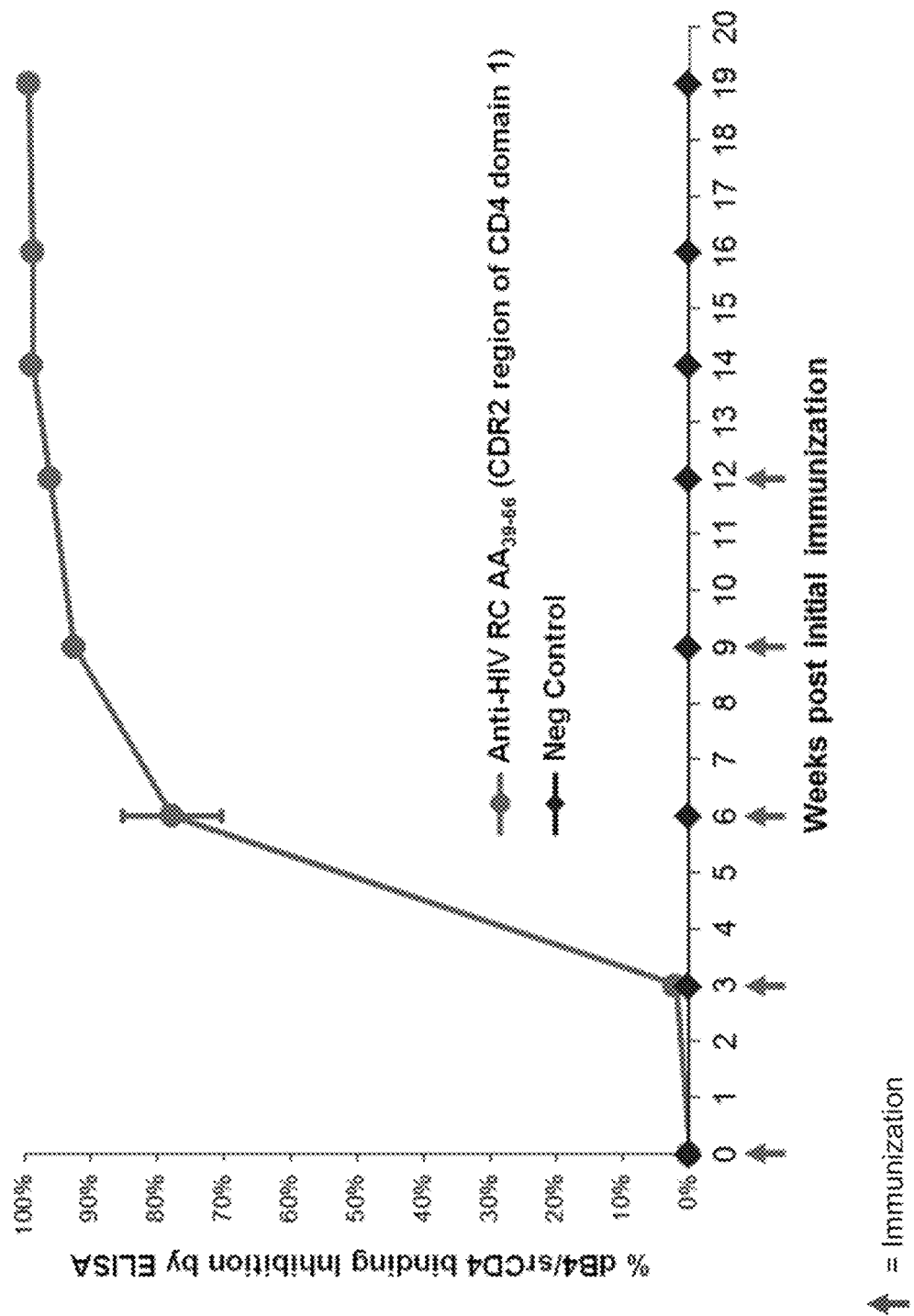
FIG. 5. Graph showing competitive inhibition of biotinylated-B4 binding to rsCD4 by anti-HIV RC polyclonal antibodies, as measured by ELISA.
Figure 8D:
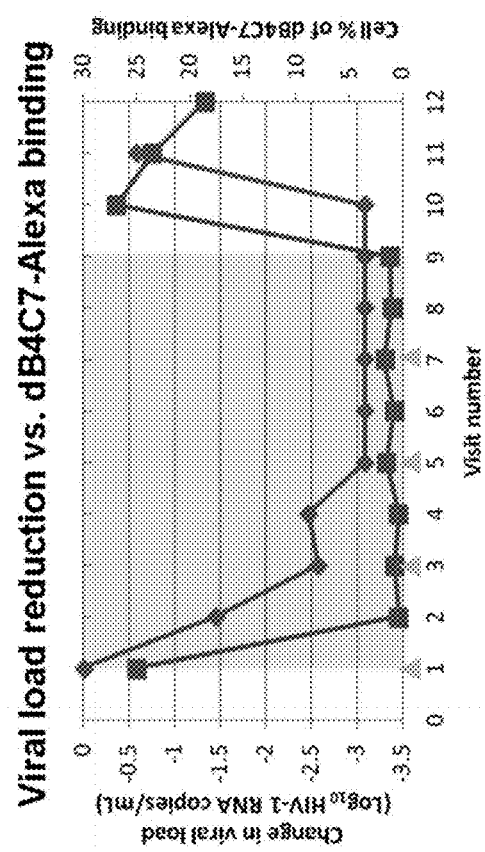

FIG. 5 shows that biotinylated-B4 binding to rsCD4 was significantly inhibited by anti-HIV RC polyclonal antibodies obtained at 6 weeks post initial immunization, reaching near complete inhibition by 9 weeks post initial immunization.

This competitive binding inhibition study further demonstrated the binding site of mAb B4 is around the CDR2 loop of domain 1 of CD4, although direct binding by mAb B4 to this peptide was not significant due to mAb B4's preferential binding to the conformational contour of membrane-bound CD4.

2.3 Reactivation of Resting CD4 Positive T Cells for Enhanced Viral Production in HIV Infected Individual Upon Crosslinking of mAb dB4

The ability of mAb dB4 to activate resting CD4+ cells was assessed by treating cells with mAb dB4 and monitoring TNF-α production, viral load, and cell proliferation.

In this study, 8-well culture plates were coated with human IgG by incubating the plate with 200 µL of Goat anti-Human IgG (Jackson ImmunoResearch) for 1 hour at 37° C. The coated plates were kept in 4° C. refrigerator until further use in this study.

PBMC from HIV patients were thawed for 1.5 hours according to standard practice. Activation of resting CD4+ cells was evaluated by treating the PBMC with either mAb dB4 (experimental), PMA+PHA (positive control), or medium alone (negative control), as set forth below.

2.3.1 MAb dB4 Treatment.

Cells were treated with mAb dB4 at a concentration of 3 µg/$10^6$ cells/mL for 1 hour at 4° C. to initiate cross-linking of the CD4 on the cells. Cells treated with mAb dB4 were then washed and cultured on coated 48-well culture plates for 7 days with RPMI medium and 10% FBS. An uncoated well was also used as a negative control. Aliquots of the culture supernatant were frozen on day 0, day 2 and day 7 for later evaluation. The Day 0 time point for the mAb dB4 sample was obtained by removing supernatant from cells after 30 minutes of treatment at 4° C.

2.3.2 PMA+PHA Treatment.

Cells were treated with 0.1 µM phytohaemagglutinin (PHA) plus 15 µg/mL phorbol myristate acetate (PMA) (Sigma) (PMA+PHA) on coated 48-well culture plates for 7 days with RPMI medium and 10% FBS, as a positive control for reactivating resting CD4+ cells. An uncoated well was also used as a negative control. Aliquots of the culture supernatant were frozen on day 0, day 2 and day 7 for later evaluation. The Day 0 time point for the PMA+PHA sample was obtained by removing supernatant from cells after 30 minutes of treatment at 4° C.

2.3.3 Medium Alone.

As a negative control, cells were incubated on coated 48-well culture plates for 7 days with RPMI medium and 10% FBS (medium alone). An uncoated well was also used as an additional negative control. Aliquots of the culture supernatant were frozen on day 0, day 2 and day 7 for later evaluation. The Day 0 time point for the medium alone sample was obtained by removing supernatant from cells after 30 minutes of incubation in medium at 4° C.

2.3.4 Analysis of CD4+ Reactivation.

Reactivation of CD4+ cells was determined by evaluating TNF-α production, viral load, and cell proliferation. The results from this study are summarized in Table 6.

The aliquots from all samples were assayed for (1) the concentration of TNF-α by quantitative ELISA; (2) HIV viral load by RT PCR; (3) cell count; and (4) viability by trypan blue, using standard methods.

Specifically, the data show that cross-linking of mAb dB4 coated PBMC cells from HIV patients triggered moderate production of TNF-α when compared to the medium alone negative control (non-detectable) and cells stimulated with PMA+PHA (about 3 to 5 times higher than mAb dB4 coated cells).

Also, the mAb dB4 sample proliferated at a rate similar to the medium alone negative control; whereas the PMA+PHA stimulated cells proliferated at a much greater extent compared to cells cross-linked with mAb dB4 (cell counts were 5 times higher in the PMA+PHA culture than the mAb dB4 culture on day 7).

However, the HIV viral load was significantly enhanced in the cells cross-linked with mAb dB4 compared to the medium control and the PMA+PHA stimulated cells. Specifically, cells cross-linked with mAb dB4 showed a 151% and 220% increase in viral load when compared to the medium alone negative control at days 2 and 7, respectively; whereas the PMA+PHA culture displayed suboptimal viral load production (55% and 78% at days 2 and 7, respectively) despite a 5 times increase in cell proliferation.

3. Conclusions

1. Murine mAb B4 was found to recognize a conformational site on CD4 close to the site recognized by antibody Leu3a (aa47-64 in the CDR2 region). MAb dB4 has the same recognition properties as those described here for mAb B4 based on the comparative studies reported in Example 7.
2. Murine mAb B4 binding to full-length rsCD4 was inhibited by polyclonal antibodies directed against a cyclic peptide containing aa39-66 of the CDR2 region of CD4 domain 1 (HIV RC peptide). These results suggest that mAb B4 recognizes aa39-66 of CD4, which corresponds to the CDR2 loop of D1 of CD4. MAb dB4 is expected to have the same recognition properties as those described here for mAb B4 based on the comparative studies reported in Example 7.
3. CD4 cross-linking with mAb dB4 was found to activate virus production in HIV infected PBMC CD4+ T cells.

Specifically, mAb dB4 lead to induction of TNF-α production and enhanced HIV production without induction of cell proliferation, as shown in Table 6.

4. Based on the results obtained in this Example, mAb dB4 (including UB-421) can mediate reactivation of resting PBMCs for enhanced viral production in HIV infected individuals.

Example 7

MAB DB4C7 and Anti-HIV RC Polyclonal Antibodies Inhibit Antigen Induced T Cell Proliferation and Cytokine (IL2 and IFN-γ) Production by CD4 Positive T Cells Thus Breaking the HIV Pathogenic Cycle of Pyroptosis 1. Background Recent reports have shown that when HIV infects permissive, activated CD4+ T cells, cell death occurs silently through caspase-3-dependent apoptosis (Doitsh, G., et al., 2014). Conversely, when either R5 or X4-tropic HIV abortively infects non-permissive, quiescent CD4+ T cells from lymphoid tissue, these cells die by caspase-1-dependent pyroptosis, an intensely inflammatory form of programmed cell death. Interferon inducing factor 16 (IFI16) has been identified as the host DNA sensor that recognizes the incomplete HIV reverse transcripts which, in turn, initiates activation of caspase-1 (Monroe, K. M., et al., 2013). In most human lymphoid tissues including tonsil, lymph node and spleen, the activated and permissive subset of cells represents 5% or less of the total CD4 T-cells, whereas the non-permissive quiescent cells represent 95% or more of the targets encountered by HIV. Thus caspase-1-mediated pyroptosis, not caspase-3-mediated apoptosis, appears predominantly responsible for driving CD4 T-cell death following HIV infection of these lymphoid tissues. These findings are further supported by analysis of fresh lymph nodes from subjects infected with R5-tropic HIV, in which caspase-1 and IL-1β are detected in the paracortical zone that is rich in resting CD4 T cells, whereas caspase-3 activity is detected in the anatomically distinct germinal centers where productively infected cells are found.

Pyroptosis most likely promotes the rapid clearance of various bacterial infections by removing intracellular replication niches and enhancing the host's defensive responses through the release of pro-inflammatory cytokines and endogenous danger signals. However, in pathogenic chronic inflammation, such as in HIV infection, pyroptosis is not a protective response and does not lead to clearance of the primary infection. In fact, pyroptosis appears to create a vicious pathogenic cycle, where dying CD4 T cells release inflammatory signals that attract more cells into the infected lymphoid tissue to die and to produce more inflammation. These events establish a chronic state of inflammation that fuels disease progression and tissue injury. Chronic inflammation might also promote maintenance of the latent HIV reservoir stimulating homeostatic proliferation of memory CD4 T cells.

The depletion of CD4 T cells and the development of chronic inflammation are signature processes in HIV pathogenesis that propel disease progression and pyroptosis provides an unexpected link between these two disease-promoting processes.

The information above suggests that pyroptosis that occurs in lymphoid tissues during HIV infection might be alleviated or reduced by a mechanism that suppresses CD4+ cell proliferation and/or inflammatory cytokine production triggered by antigenic stimulation of CD4+ cells.

2. Experiment

A study was performed to determine if mAb dB4 can break the pathogenic cycle caused by pyroptosis by inhibiting the development of chronic inflammation in HIV infected individuals. Inhibition of cytokine production triggered by antigenic stimulus would help to relieve the burden of pyroptosis by many of the resting T cells, which already have an abortive HIV infection, thus breaking the HIV pathology in CD4 positive T cell depletion due to cytokine production.

An in vitro model employing Staphylococcal Enterotoxin B (SEB) was used to assess the ability of mAb dB4C7 (UB-421) to inhibit PBMC T cell proliferation in both normal and HIV infected individuals. SEB is a superantigen that has the ability to stimulate all T cells bearing a particular T cell antigen receptor (TCR) and induces massive cytokine production.

Through collaboration with Drs. Huyen Cao and Mohamed Elrefaei, functional analyses of normal human donors (n=3) and HIV-infected donors (n=6, ART naïve, CD4+ count>200, viral load>10,000) were conducted to assess if mAb dB4C7 (UB-421) or anti-HIV RC polyclonal antibodies directed against the CDR2 region of D1 of CD4 (described in Example 9) could inhibit cell proliferation and cytokine (IL2 and IFN-γ) production.

2.1 Study Subjects and Samples.

HIV-positive ART treatment naïve volunteers (n=6) were recruited from the REACH cohort (San Francisco). Three age-matched, HIV-seronegative control volunteers were also included in the study. PBMC were separated and cryopreserved in liquid nitrogen until assay time.

2.2 Saturating Concentration of mAb dB4C7 or Purified Anti-HIV RC Polyclonal Antibodies were Used.

CD4+ T lymphocytes were first stained in an indirect immunofluorescence study with mAb dB4C7 IgG or anti-HIV RC polyclonal antibodies IgG followed by Alexa-goat anti-HuIgG or Alexa-goat anti-guinea pig IgG, respectively. The resultant stained cells were analyzed by flow cytometry for the percent positive cells detected. Both mAb dB4C7 and anti-HIV RC polyclonal antibodies were titered between 50 µg/mL and 0.0025 µg/mL in a 2-fold dilution. Antibody titration for mAb dB4 and anti-HIV RC antibodies were determined as % CD4 binding vs antibody concentration in µg/mL. These titrations were assessed prior to use in T cell functional assays performed on HIV infected and normal individuals.

FIG. 6 shows that saturating concentrations for the respective reagents used in the functional studies were found to be 1 µg/mL for mAb dB4 (dB4C7) and 25 µg/mL for anti-HIV RC polyclonal antibodies.

2.3 Proliferation of CD4+ or CD8+ T Cells.

Cell proliferation was analyzed by a CFSE (carboxyfluorescein succinimidyl ester) fluorescence assay, which follows the loss of CFDA-SE (carboxy-fluorescein diacetate, succinimidyl ester) stain upon cell division. CFSE was used as a surrogate for a $^3$H-Thymidine (proliferation) assay.

PBMCs were incubated with saturating concentrations of mAb dB4C7 or purified anti-HIV RC polyclonal antibodies to coat the CD4 receptors on the surface of the cells. Cells were also incubated with anti-HIV RC isotype at 25 µg/mL and PHA (10 µg/ml; Sigma-Aldrich) as negative and positive controls, respectively.

PBMCs were labeled with CFDA-SE (Molecular Probes, Eugene, Oreg.) in PBS, then quenched with 100% FCS (Sigma-Aldrich, St. Louis, Mo.). The cells were then resuspended in RPMI 1640 (Sigma-Aldrich) with 10% FCS after washing with PBS.

Cells were then cultured in the presence of SEB Ag (1 µg/mL) for 5 days at 37° C. in 5% $CO_2$ and analyzed for the expression of surface markers.

Flow cytometry was conducted for analyses of CD3+ (Amcyan) gated CD4+(PE, D2), CD8+ (PercpCY5.5) cell populations which were each further measured for % CFSE positive cells as % of proliferating cells. Forty thousand (40,000) lymphocytes per sample were acquired using an LSR II (BD Biosciences, Mountain View, Calif.), and analysis was performed by FLOWJO software (TreeStar, San Carlos, Calif.). Results were measured as % of dividing CD4 (or CD8) T cells. All study participants demonstrated significant proliferation following PHA stimulation. Proliferation of CD4 T cells without SEB Ag stimulation (negative controls) was <0.5%.

2.4 Intracellular Staining Assay for Measurement of Cytokines (IL2 and IFN-γ Production.

PBMC ($0.5 \times 10^6$ cells) were incubated for 2 hr with SEB Ag (1 µg/mL) at 37° C. in 5% $CO_2$. Cells were washed with PBS containing 0.1% FCS (wash buffer), and fixed by resuspending the cells in lysing solution (BD Biosciences) for 10 min at room temperature. Cells were washed once with wash buffer, then permeabilized by resuspension in 0.5 mL of permeabilizing solution 2 (BD Biosciences), and incubated for 10 min. at room temperature. Cells were subsequently washed with wash buffer and stained with anti-IL-2 APC, anti-IFN-γ (PE CY7), and anti-CD3 (Amcyan), anti-CD4 (PE, D2) or anti-CD8 (Percp CY5.5) (BD Pharmingen). Forty thousand (40,000) lymphocytes per sample were acquired using an LSR II (BD Biosciences), and analysis was performed by FLOWJO software (TreeStar). Percentage of cytokine-producing CD4 or CD8 T cells without Ag stimulation was <0.05% (negative control). Results were expressed as % of CD4+(or CD8+) T cells that express IFN-γ or IL2.

2.5 Statistical Analysis.

Statistical analysis and comparisons were performed with paired t test.

3. Results

The results obtained from this SEB Ag induced T cell proliferation study revealed that both mAb dB4C7 (1 µg/mL) and anti-HIV RC polyclonal antibodies (25 µg/mL), under saturating conditions, decreased CD4+ T cell proliferation but not CD8+ T cell proliferation in both HIV ART treatment naïve patients and in age-matched normal individuals individuals (data not shown).

Both mAb dB4 (1 µg/mL) and purified anti-HIV RC polyclonal antibodies (25 µg/mL), at their respective saturating PBMC surface CD4 binding concentrations, suppressed IL2 production by superantigen SEB induced proliferating CD4+ T cells in HIV negative (FIG. 7a) and HIV positive (FIG. 7b) individuals. Such suppression was not found in CD8+ T cells from the same HIV positive and negative individuals (FIG. 7c).

Both mAb dB4 (1 µg/mL) and purified anti-HIV RC antibodies (25 µg/mL), at their respective saturating concentrations, also suppressed IFN-gamma production by superantigen SEB induced proliferating CD4+ T cells in HIV negative (FIG. 7d) and HIV positive (FIG. 7e) individuals. Such suppression was not found in CD8+ T cells from the same HIV negative (FIG. 7f) and positive (FIG. 7g) individuals.

4. Conclusions

Antibody mAb dB4C7 (UB-421) and anti-HIV RC polyclonal antibodies, both targeting CDR2 region of CD4 domain 1, were found to suppress super antigen SEB induced T cell proliferation and cytokine (IL2 and IFN-γ) production by CD4 positive T cells, but not T cell proliferation and cytokine (IL2 and IFN-γ) production by CD8 positive T cells. The finding that dB4C7 and anti-HIV RC polyclonal antibodies could suppress CD4+ T cell proliferation and the associated cytokine (IL2 and IFN-γ) production suggests that the antibody may exert similar suppressive effects on other CD4 positive cells related cytokine production with the potential of breaking the HIV pathogenic cycle of pyroptosis.

The suppressive effect on CD4 positive T cell proliferation and associated cytokine (IL2 and IFN-γ) production observed in this and preceding Examples is highly significant in that the CDR2 region targeting antibodies described herein may exert simultaneous opposing effects on CD4 cells, including: (1) reactivation of resting HIV infected CD4 positive T cells to trigger the release of HIV from their latent status (as discussed in Example 9); (2) competitive inhibition and prevention of HIV entry into uninfected CD4 positive T cells from new virus released by reactivation of the resting CD4+ T cells (Examples 4 and 6); and (3) inhibition of T cell proliferation and cytokine production by CD4 positive T cells upon (super)antigenic stimulation (this Example).

The unique biological features of mAb dB4 and anti-HIV RC polyclonal antibodies targeting the very site of HIV binding and initiation of immune responses (i.e., the CDR2 region of CD4 domain 1) provide properties required for functional cure of HIV infection, namely the ability (1) to prohibit HIV infection through entry inhibition; (2) to reactivate virus production in resting T cells; and (3) to directly alter cytokine production.

Example 8

A Phase IIA, Open-Label, Multiple-Administration, Dose-Dependent Trial to Investigate the Safety and Efficacy of the UB-421 in Asymptomatic HIV-1 Infected Adults 1. Study Objectives:
1. To evaluate the safety and tolerability of multiple-administrations of two dose regimens of UB-421 in asymptomatic HIV-1 infected subjects.
2. To obtain evidence of antiviral activity of multi-administration of two dose regimens of UB-421 in these subjects.
3. To evaluate the antiviral activity and safety profiles in order to determine the optimal UB-421 administration and dose regimen.
(Clinical Trial Identifier: NCT01668043).

2. Study Design

This was an open-label study with repeated intravenous administrations of UB-421. Subjects who were seropositive for HIV-1 and asymptomatic were screened for eligibility. Twenty-nine (29) enrolled subjects received multiple intravenous infusions of the study drug (UB-421) at one of the two dose levels, 10 mg/kg weekly (Cohort 1) or 25 mg/kg bi-weekly (Cohort 2), for an eight-week treatment period. Subjects were assigned to one of the two study cohorts by site and by turns based on the enrollment sequence. Subjects were followed for an additional eight-week period after the eight-week treatment period. The study ended at week 16.

3. Criteria for Inclusion

Subjects were required to meet the following criteria to be eligible for the phase IIa trial:

1. Asymptomatic, antiretroviral therapy (ART)-naïve, HIV-1 seropositive
2. CD4+ T cell count>350 cells/mm$^3$
3. HIV-1 viral load>5,000 copies/mL
4. No active infection requiring immediate therapy (except HIV-1)
5. No use of immunomodulating drugs or systemic chemotherapy
6. No need for Highly Active Antiretroviral Treatment (HAART).

After completion of this study, subjects followed the routine monitoring schedule (with no antiretroviral agents) at outpatient clinics or received a standard-of-care antiretroviral therapy (e.g. HAART) when deemed necessary by the principal investigator according to current Guidelines for diagnosis and treatment of HIV/AIDS. Individuals who were enrolled in the phase I trial with UB-421 and met the entry criteria of the phase IIa trial were allowed to join this study.

4. Investigational Product(s)

The UB-421 (dB4C7 mAb) were supplied at a concentration of 10 mg/mL (100 mg in 10 mL vial).

Each enrolled subject received multiple intravenous infusions of UB-421 at one of the following dosage levels: 10 mg/kg weekly (Cohort 1) or 25 mg/kg bi-weekly (Cohort 2) for eight weeks. The appropriate volume of UB-421 was based on the specified dose and the subject's body weight. The volume of each individual dose was adjusted using sterile saline so that each individual subject within a cohort was infused with an equivalent infusion volume of drug. The total volume of infusion was approximately 100 mL for 10 mg/kg and 200 mL for 25 mg/kg dose cohorts. The infusion time for each administration was approximately one to two hours.

5. Criteria for Evaluation:

5.1 Primary Safety and Efficacy Endpoints:

The following safety and tolerability parameters of UB-421 were evaluated through week 16 (end of study):

1. Physical examination (PE)
2. Vital signs
3. Clinical Chemistry & Hematology Tests
4. Incidence of adverse event (AE)/serious adverse event (SAE)

The following efficacy parameters of UB-421 were evaluated for each study cohort during the study period (from V2 to V12):

1. Individual maximal viral load reduction
2. Mean maximal viral load reduction 5.2 Secondary Virologic Endpoints The following virologic responses were evaluated during the study period (from V2 to V12):

1. Individual maximal viral load reduction and mean maximal viral load reduction by subgroup within and between each study cohort.
2. The proportion of subjects with viral load<50 copies/mL;
3. The proportion of subjects with viral load<200 copies/mL;
4. The proportion of subjects with viral load reduction>0.5 $\log_{10}$ copies/mL;
5. The proportion of subjects with viral load reduction>1 $\log_{10}$ copies/mL;
6. The proportion of subjects with viral rebound (over 0.5 $\log_{10}$ increase in viral load from the nadir) up to 7 days and 14 days after the last completed study drug administration for cohort 1 and for cohort 2, respectively;
7. Serum concentrations of anti-UB-421 antibodies (immunogenicity of UB-421);
8. Changes in CD4+ and CD8+ T cell counts;
9. Pharmacokinetic parameters of UB-421 ($C_{max}$, $AUC_{(0 \to \infty)}$ and $AUC_{(0 \to last)}$).

6. Analysis Population:

Intent-to-treat (ITT) population: 29 subjects who received at least one administration of the study drug. The ITT population for Cohort 1 and Cohort 2 was 14 subjects and 15 subjects, respectively.

Per-protocol (PP) population: 18 subjects who received all administration of the study drug, with a valid baseline and at least one valid post-treatment efficacy measurement (HIV-1 viral load test), and lack major protocol violations. The PP population for Cohort 1 and Cohort 2 was 7 subjects and 11 subjects, respectively.

Safety and Immunogenicity population: 29 subjects included in the Intent-to-Treat population.

Pharmacokinetic population: was based on a subset population within the safety and immunogenicity populations.

Baseline data and safety endpoints were analyzed on safety and immunogenicity populations, while efficacy analysis was performed on both ITT and PP populations. Pharmacokinetic analysis was conducted on pharmacokinetic population.

7. Duration of Study Period

Screening period: <4 weeks
Treatment period: 8 weeks
Follow-up period: 8 weeks following the end of the Treatment Period Visit 0 represented the initial screening and each visit during the study represents a 1 week period. The Follow-up period was generally performed in weekly intervals.

8. Summary of Results:

8.1 Study Population.

A total of 33 asymptomatic HIV infected adults were screened in two study sites in Taiwan. Of those, 29 subjects passed the screening criteria and were selected for the trial. All 29 eligible subjects were male.

8.2 Safety and Tolerability Results:

All 29 subjects experienced at least 1 AE during the study, totaling 128 AEs. Among which, 114 (89.06% in all 29 subjects) were treatment-emergent adverse event (TEAEs) and 14 (10.94% in 5 subjects) were pre-treatment AEs. No serious adverse events (SAEs) were observed in the 29 subjects. All pre-treatment AEs were unrelated to UB-421 and none of these events were considered SAEs. Most (78.95%) of the TEAEs reported were mild, 17.54% were moderate, and 3.51% (in 1 subject) were severe.

The most frequently observed (>10%) TEAE was skin rash and urticarial. Other than adverse events, abnormalities in hematology (154 events in 22 subjects) and biochemistry (32 events in 6 subjects) laboratory test results were observed in 22 subjects. However, most of the changes were minor and were not clinically significant. Physical examination results and vital signs were mostly normal or non-clinically significant during the study period.

UB-421 was well tolerated during the study period with an overall treatment tolerability for the 8-week Treatment period of 73.84% as specified by the clinical trial protocol.

8.3 Pharmacodynamics 8.3.1 CD4$^+$ T and CD8$^+$ T cell counts. After the 8-week Treatment period and 8-week Follow-up period, mean CD4$^+$ T cell counts decreased slightly from baseline by 55.10±117.97 cells/mm$^3$ while mean CD8+ T cell counts increased from baseline by 193.31±459.34 cells/mm$^3$. Representative CD4$^+$ T cell counts for subjects in Cohort 1 and mean CD4 T cell count are shown in FIG. 9a upper panel. Representative CD4$^+$ T cell counts for subjects in Cohort 2 and mean CD4 T cell count are shown in FIG. 9a lower panel.

8.3.2 Coating of CD4 Receptors with UB-421.

The extent of CD4 receptor coating was detected by flow cytometry with fluorescence-conjugated UB-421. The results obtained from four representative subjects, two patients from Cohort 1 and two patients from Cohort 2, are shown in FIGS. 8a-8b and FIGS. 8c-8d, respectively. The assay's sensitivity is 0.15 µg/mL. Clinical efficacy of UB-421 upon repeated dosing at 10 mg/kg weekly or 25 mg/kg biweekly revealed viral reduction down to non-detectable level in the presence of >10 µg/mL. UB-421 serum level when used as a monotherapy. There is no viral rebound as long as the PBMC CD4+ cells are fully coated (i.e. % dB4C7-Alexa binding approaching 0).

Full coating of CD4 receptors on PBMC with UB-421 was achieved after two to three administrations of UB-421 at both dosage levels. Additionally, full coating of CD4+ T cells with UB-421 was maintained throughout the entire treatment period (FIGS. 8a-8d). In most of the subjects, UB-421 binding to CD4 receptors diminished and returned to baseline values within three weeks of the last UB-421 infusion, as determined by binding of fluorescent dB4C7 mAb (dB4C7-Alexa).

The concentration of UB-421 present in the serum of the subjects during the study was evaluated to determine the serum concentration of UB-421 sufficient to achieve full CD4 coating and HIV-1 viral suppression. Based on the data obtained, constant full coating of CD4+T cells and HIV-1 viral suppression by UB-421 was achieved as long as the serum concentration of UB-421 was maintained above 10 µg/mL (FIGS. 8a-8d).

8.4 Pharmacokinetics:

The mean AUC observed in Cohort 1 increased from 17300±10000 µg×hr/mL (Visit 1-2) to 23900±10700 µg×hr/mL (Visit 8-9) then returned to baseline at Visit 11-12. The mean $AUC_{(0\rightarrow last)}$ observed in Cohort 1 was 171000±70300 µg×hr/mL.

The mean AUC observed in Cohort 2 increased from 56500±19500 µg×hr/mL (Visit 1-3) to 61100±20700 µg×hr/mL (Visit 7-9) then returned to baseline at Visit 11-12. The mean $AUC_{(0\rightarrow last)}$ observed in Cohort 2 was 239000±73900 µg×hr/mL.

These data demonstrate that the mean serum drug concentration, as assessed by $AUC_{(0\rightarrow last)}$, was higher among subjects administered 25 mg/kg bi-weekly UB-421 infusion (Cohort 2, 239000±73900 µg×hr/mL) as compared to those received 10 mg/kg weekly UB-421 infusion (Cohort 1, 171000±70300 µg×hr/mL).

8.5 Efficacy Results:

Twenty-nine (29) HIV-1 infected subjects were recruited in this study and received at least one dose of UB-421 (ITT population). Of the twenty-nine (29) subjects recruited, a total of eighteen (18) subjects completed the 8-week Treatment period, receiving all administrations of the study drug (PP population). The efficacy of the multi-administration of UB-421 was evaluated by assessing individual and mean maximal viral load reduction of the enrolled asymptomatic HIV-1 infected subjects during the study and the results for the ITT and PP populations for Cohorts 1 and 2 are summarized in Table 7.

It was found that the mean maximal viral load reduction did not differ significantly between the two dosage levels in either the ITT or the PP populations. Specifically, viral loads were reduced in the ITT population by 2.27±0.60 log$_{10}$ copies/mL in Cohort 1 and 2.45±0.46 log$_{10}$ copies/mL in Cohort 2. In the PP population, viral loads were reduced by 2.73±0.34 log$_{10}$ copies/mL in Cohort 1 and 2.47±0.45 log$_{10}$ copies/mL in Cohort 2.

During the treatment period, ≥0.5 log$_{10}$ copies/mL of viral load reduction was observed in all (n=29, 100.00%) study subjects; and ≥1 log$_{10}$ copies/mL of viral load reduction was also observed in all (n=29, 100.00%) study subjects.

Further evaluation of the data obtained during the Treatment period revealed the following:

In Cohort 1, 8/14 (57.14%) of subjects in ITT and 5/7 (71.43%) subjects in PP had viral load≤200 copies/mL; moreover, 3/14 (21.43%) of subjects in ITT and 3/7 (42.86%) of subjects in PP had viral load<50 copies/mL.

In Cohort 2, 10/15 (66.67%) subjects in ITT and 7/11 (63.64%) subjects in PP had viral load≤200 copies/mL; and 3/15 (20.00%) subjects in ITT and 2/11 (18.18%) of subjects in PP had viral load<50 copies/mL.

Representative viral load reduction data from subjects in Cohorts 1 and 2 are shown in Table 7 and FIG. 9a. There were no statistically significant differences in the proportion of subjects with viral load reduction within each cohort, between cohorts, or between sub-populations within each cohort. Furthermore, viral loads were reduced to levels below the current assay detection limit (20 copies/mL) in 42.9% and 18.2% of the subjects in Cohort 1 and 2, respectively, during the eight-week Treatment period. In all subjects, the viral load reduction persisted while the CD4+ T cells were completely coated by UB-421. Viral loads returned to the baseline levels in both cohorts by the end of the Follow-up period. In addition, no viral rebound was observed in any of the study subjects during the Treatment period. No quantitatable anti-UB421 antibodies was detected throughout the treatment period from patient in both cohorts.

8.6 Comparison of UB-421 with TMB-355:

The results obtained in this study for UB-421 were evaluated against results obtained in similar studies for TMB-355 (ibalizumab, formerly TNX-355) performed by others (Jacobson, J. L., et al., 2009; Toma, J., et al., 2011; and Pace, C. S., et al., 2013). FIG. 10a show superior viral load reduction up to >3 Log$_{10}$ with no viral load rebound in the presence of UB-421 with full coating of CD4+ cells. In contrast, patients undergoing treatment with TMB-355 encountered viral rebound after only one week from treatment even in the presence of full coating of CD4+ cells, indicative of development of resistant viral mutants (FIG. 10b).

A comparison of these two treatment regimens, as illustrated in the figures, demonstrates that treating HIV infected subjects with UB-421 has distinct advantages over TMB-355 treatment. Specifically, UB-421 provides a continual decrease in HIV viral load throughout out the Treatment period and even one or two weeks into the Follow-up period with maximal viral load reduction>3 lop). In contrast, TMB-355 provides only a temporary viral load reduction with the first administration and maximal viral load reduction of approximately 1 log$_{10}$.

Also, prior studies using TMB-355 found that, despite the presence of serum TMB-355 and full coating of CD4 positive T cells, HIV viral rebound occurred after one week into the treatment (Jacobson, J. L., et al., 2009). This result is consistent with the earlier prediction in Example 4 above that a non-competitive entry inhibition mechanism, as mediated by TMB-355 (ibalizumab), would afford a high likelihood for development of resistant HIV mutants during the antibody treatment period. Indeed, viral resistant mutants were found with mutations identified at V5 region of gp120 (Toma, J., et al., 2011; Pace, C. S., et al., 2013) from patients receiving TMB-355 treatment for viral load reduction.

There are a few very imteresting observation as to the proliferative responses of CD3+, CD3+/CD4+, vs CD3+/CD8+ cell populations when these cells were stimulated by various antigens including superantigen SEB, CMV peptide pp65, or HIV gag peptides with consensus B sequences (HIV Gag motif peptides).

As shown in FIG. 9b, no difference was observed by CD3 or CD3/CD4+ cells were observed as to the stimulative responses by both populations either before (W1), at the end (W8) or 2 months after (W16) the treatment course for superantigen SEB (upper panel) or CMVpp65 peptides (lower panel).

Figure 11:
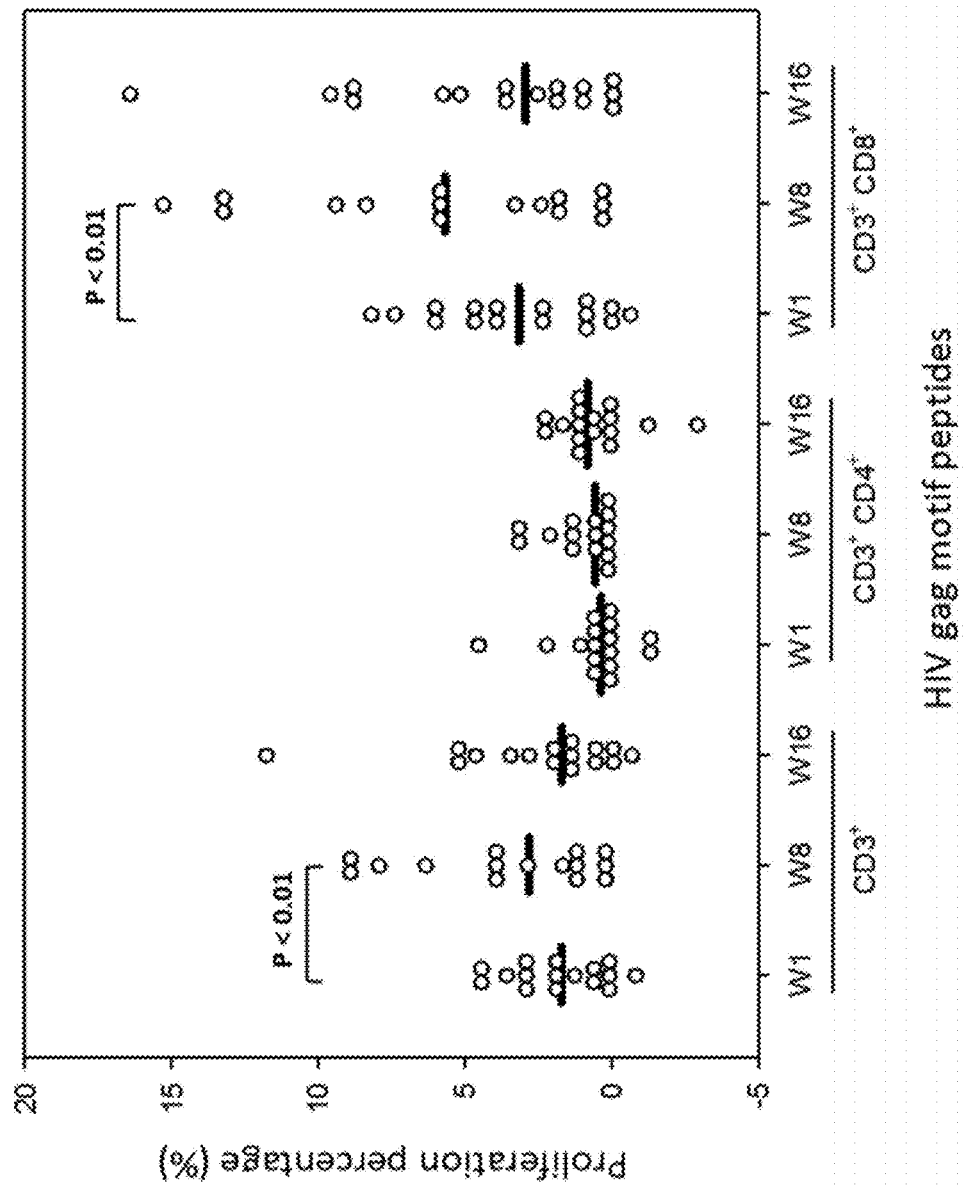
FIG. 11. The proliferative percentage of CD3+, CD3+/CD4+ and CD3+CD8+ cells from patents before (W1), at the end of (W8), and post (W16), UB421 treatment when PBMC were obtained from patients receiving UB421 and stimulated by HIV Gag motif peptides with consensus B sequences. There is a statistically significant increase in proliferation percentage in CD3+ (p<0.01) T cells which is attributed mainly to CD3+/CD8+ (p<0.01) T cell population.

A very interesting observation was made when HIV Gag motif peptides were used to stimulate PBMCs from patients receiving UB421 either before (W1), at the end (W8) or 2 months after (W16) the treatment course (FIG. 11). Significant proferative CD3+ proliferative responses were found which upon further analysis was due to CD3/CD8+ population ($P<0.01$) between W1 and W8. This significant increase in CD3/CD8+ population in the HIV patients upon stimulation with HIV Gag motif peptides after receiving UB421 could give important clinical meaning indicative of improved HIV specific CTL responses in these patients which may allow better monitoring of HIV infected T cells in these patients, thus resembling more along those patients of nonprogressors.

9. Conclusion

Eight-week treatment with UB-421 in asymptomatic HIV-1 infected subjects was found to be well tolerated. In addition, mean CD4 T cell counts (FIG. 9a) from both cohorts 1 (upper panel) and 2 (lower panel), respectively, remained stable throughout the two-month period monitored.

More importantly, treatment with UB-421 resulted in significant viral load reduction in all subjects (100% of the treated subjects responded with a maximal reduction of $\geq 1$ $\log_{10}$ copies/mL. Both regimens, 10 mg/kg weekly (Cohort 1) and 25 mg/kg bi-weekly (Cohort 2) infusions, showed similar efficacy in viral load reduction. The mean maximal viral reduction in ITT population reached to $2.27\pm0.60$ $\log_{10}$ copies/mL in Cohort 1 and $2.45\pm0.46$ $\log_{10}$ copies/mL in Cohort 2). The observed viral reduction efficacy with UB-421 is superior than any other small molecule anti HIV drugs tested thus far.

The clinical trial results from this carefully executed multiple-dose phase IIa trial of UB-421 demonstrated high tolerability, safety, and an unprecedented efficacy in viral load reduction as a monotherapy without viral rebound during the Treatment period. The results obtained in this study are unexpected and contradict the long-held suspicion in the field that anti-CD4 monoclonal antibodies that bind to domain 1 of CD4 would be immunosuppressive because of interference with major histocompatibility complex class II-mediated immune functions and such therapies would be unsuitable for the treatment of HIV disease (Jacobson, J. L., et al., 2009). These results further suggest that additional modalities of HIV therapy using UB-421 in combination with orthogonal HAART and/or other HIV reservoir activating agents, such as HDACi, could achieve a functional cure for HIV infection.

Example 9

Treatment Modality Employing UB-421 Monotherapy as a Substitute for Antiretroviral Therapy in HIV-1 Infected Adults FIG. 12 illustrates a treatment modality for HAART stabilized patients employing UB-421 monotherapy as a substitute for antiretroviral. Detailed objectives and protocol are described below.

1. Patient Populations Applied

Subjects who are seropositive for HIV-1 with viral suppression by stable highly active antiretroviral therapy (HAART) would be eligible for such treatment.

The eligible patients will receive UB-421 administered through either IV, IM or SC route for an initial period of 4 months followed by another cycle of HAART treatment. A "HAART-UB-421" alternating treatment cycle can be repeated several times until viral rebound is no longer observed upon withdrawing both UB-421 and HAART therapies, thereby resulting in a functional cure for HIV infection.

More specifically, as shown in FIG. 12 these subjects received multiple intravenous infusions of the study drug (UB-421) at one of the two dose levels, 10 mg/kg weekly or 25 mg/kg bi-weekly, for eight-week and sixteen-week treatment periods, respectively. The HAART regimens were withdrawn on the day before the first UB-421 infusion. Prior to UB-421 administration, the subjects were given prophylactic medication (pre-medication), including steroid and anti-histamine drugs as judged by principal investigator, to prevent infusion reactions. After completing the last scheduled UB-421 administration, all subjects restarted their original or other appropriate virus-sensitive antiretroviral therapies on the same day. The use of HAART regimens were judged by the principal investigators. Viral load and CD4 and CD8 cell counts from all patients were monitored during the treatment period and 2 months after the treatment period ends.

2. Inclusion Criteria

Subjects were included in this treatment modality if they meet all of the following criteria:

1. HIV-1 seropositive;
2. Aged 20 years or older;
3. Have received HAART treatment, defined as at least 2 nucleoside/nucleotide reverse transcriptase inhibitors (NRTIs) plus a non-nucleoside reverse transcriptase inhibitor (NNRTI), integrase inhibitor, or a protease inhibitor, for at least 2 years; the treatment is ongoing and without changes of drugs within one year prior to entry of the study;
4. With two measurements of CD4+ T cell count 500 cells/mm³ or CD4 percentage 28% within 1 year prior to the screening visit;
5. With a CD4+ T cell count 500 cells/mm³ obtained within 4 weeks prior to the screening visit or at the screening visit;
6. HIV-1 plasma RNA remains undetectable for at least 1 year prior to the screening visit, with at least 2 viral load measures per year. The viral load is also undetectable within 4 weeks prior to the screening visit or at the screening visit; single episode of detectable HIV plasma RNA prior to 4 weeks before the screening visit will not exclude participation.

3. Exclusion Criteria

Subjects were excluded from the treatment modality for any of the following reasons:

1. Any active infection (except for HIV) requiring immediate therapy;
2. Any previously diagnosed or active AIDS-defining illness per Category B and Category C conditions according to the U.S. Centers for Disease Control and Prevention (CDC) Classification System for HIV Infection;
3. Body weight>80 kg;
4. Any documented CD4+ T cell count<250 cells/mm$^3$ or CD4+ T cell percentage≤14% within 12 weeks before screening;
5. Previously enrolled in either phase I or phase IIa trials of UB-421 or any history of the presence of anti-UB-421 antibody;
6. Any previous exposure to a monoclonal antibody within 12 weeks prior to first dose of study drug UB-421;
7. Any significant diseases (other than HIV-1 infection) or clinically significant findings, including psychiatric and behavioral problems, determined from screening, medical history and/or physical examination that, in the investigator's opinion, would preclude the subject from participating in this study;
8. Any vaccination within 8 weeks prior to first dose of study drug;
9. Any immunomodulating therapy (including interferon), systemic chemotherapy within 12 weeks prior to first dose of study drug;
10. Life expectancy of less than 12 months;
11. Any illicit intravenous drugs within 12 weeks prior to first dose of study drug;
12. More than one change of HAART regimen because of virologic failure, and prior non-Hodgkin's lymphoma or Kaposi's sarcoma;
13. Any current alcohol or illicit drug use that, in the investigator's opinion, will interfere with the subject's ability to comply with the dosing and visit schedules and protocol evaluations.

4. Drug Product

Drug Product UB-421 (dB4C7 mAb) was supplied at a concentration of 10 mg/mL (100 mg in 10 mL vial). Subjects received either eight weekly doses of 10 mg/kg UB-421 or eight bi-weekly doses of 25 mg/kg UB-421 by intravenous infusion.

The appropriate volume of UB-421 was based on the specified dose and the subject's body weight. The volume of each individual dose was adjusted using sterile saline so that each individual subject within a cohort was infused with an equivalent infusion volume of drug. The total volume of infusion was approximately 100 mL for 10 mg/kg and 200 mL for 25 mg/kg dose cohorts. The infusion time for each administration was approximately one to two hours.

5. Results 5.1 Study Population.

A total of 29 HAART stabilized HIV patients were screened in two study sites in Taiwan. Of those, 29 subjects passed the screening criteria and were selected for the trial. All 29 eligible subjects were male.

5.2 Safety and Tolerability Results:

All 29 subjects experienced at least 1 AE during the study. All pre-treatment AEs were unrelated to UB-421 and none of these events were considered SAEs. Most of the TEAEs reported were mild. The most frequently observed TEAE was skin rash and urticarial. Physical examination results and vital signs were mostly normal or non-clinically significant during the study period.

UB-421 was well tolerated during the study period with an overall treatment tolerability for the 8-week or 16-week Treatment period as specified by the clinical trial protocol.

5.3 Pharmacodynamics 5.3.1 CD4$^+$ T and CD8$^+$ T cell counts. After the 8-week (cohort 1) and 16-week (cohort 2) Treatment periods and 8-week Follow-up period (V12), mean CD4$^+$ T cell counts remained about the same after the treatment and monitoring period (V12) from baseline (V1) with no significant difference (P=0.331 for cohort 1 and P=0.905 for cohort 2) as shown in FIG. 13, while mean CD8$^+$ T cell counts increased significantly after the treatment and monitoring period (V12) for from baseline (V1) for both cohort1 (P<0.001) and cohort 2 (P<0.004) as shown in FIG. 14. This significant increase in CD8+ cells observed in HAART stabilized patients after UB421 treatment is also observed in treatment naïve patients receiving UB421 as shown in Example 7, FIG. 9a lower panel, an important characteristic of patients receiving UB421 treatment.

5.3.2 Coating of CD4 Receptors with UB-421.

Figure 15A:
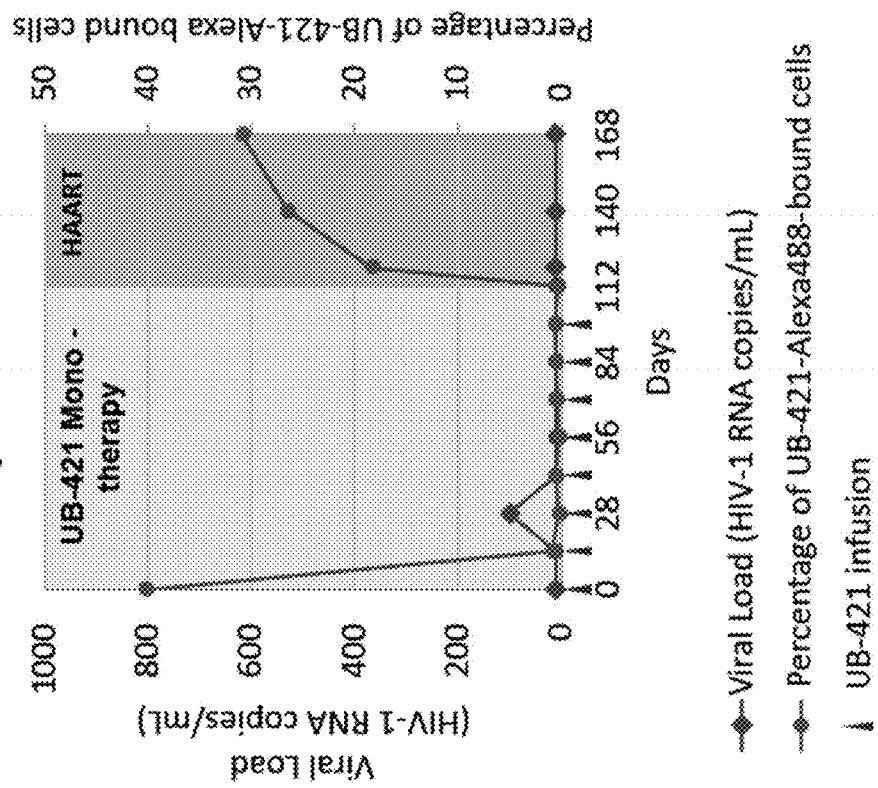
FIGS. 15A and 15B. Graphs showing the clinical efficacy of UB-421 treatment, as measured by mean viral load reduction (HIV RNA copies/mL), and pharmacokinetics of UB-421, as measured by mean percentage of UB-421-alexa488 bound cells over the course of a Phase IIa clinical trial employing UB-421 monotherapy as a substitute for antiretroviral therapy in HIV-1 infected adults.
Figure 15B:
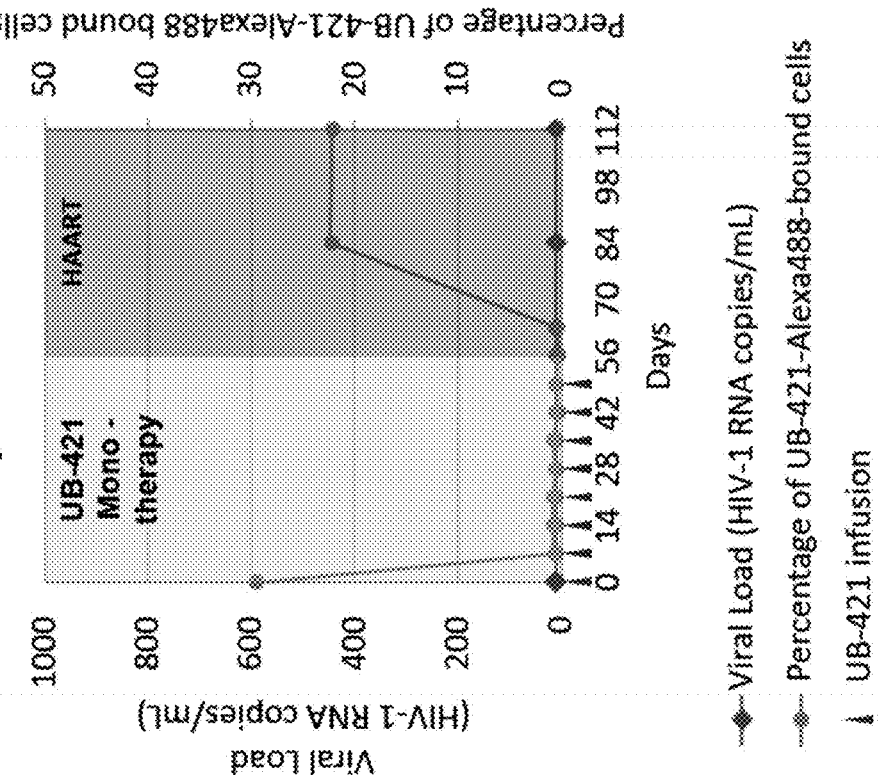

The extent of CD4 receptor coating was detected by flow cytometry with fluorescence-conjugated UB-421. The results obtained for patients from from Cohort 1 and Cohort 2, are shown in FIGS. 15A and 15B, respectively. Full coating of CD4 receptor is found for 63 and 112 days for cohort 1 and cohort 2 respectively. Clinical efficacy of UB-421 upon repeated dosing at 10 mg/kg weekly or 25 mg/kg biweekly revealed complete suppression of viral load at non-detectable level throughout the treatment and full CD4 receptor coating period and also during the post treatment period (from days 63 to 112 for cohort 1 and days 112 to 168 for cohort 2) when patients returned to their original HAART treatment protocol in all (100%) patients. There is no viral rebound as long as the PBMC CD4+ cells are fully coated (i.e. % dB4C7-Alexa binding approaching 0) during the treatment period.

Full coating of CD4 receptors on PBMC with UB-421 was achieved after only one administration of UB-421 at both dosage levels. Additionally, full coating of CD4+ T cells with UB-421 was maintained throughout the entire treatment period (FIG. 15). In most of the subjects, UB-421 binding to CD4 receptors diminished and returned to baseline values within three weeks of the last UB-421 infusion, as determined by binding of fluorescent dB4C7 mAb (dB4C7-Alexa).

The concentration of UB-421 present in the serum of the subjects during the study was evaluated to determine the serum concentration of UB-421 sufficient to achieve full CD4 coating and HIV-1 viral suppression. Based on the data obtained, constant full coating of CD4+ T cells and HIV-1 viral suppression by UB-421 was achieved as long as the serum concentration of UB-421 was maintained above 10 µg/mL.

5.3.3 Quantification of Regulatory T Cells.

The regulatory T cells (Tregs), formerly known as suppressor T cells, are a subpopulation of T cells which modulate the immune system, maintain tolerance to self-antigens, and prevent autoimmune disease. Tregs are immunosuppressive and generally suppress or downregulate induction and proliferation of effector T cells. Tregs express the biomarkers CD4, FOXP3, and CD25 and are thought to be derived from the same lineage as naïve CD4 cells. (website: en.wikipedia.org/wiki/Regulatory_T_cell). We therefore included the % Tregs (out of the CD3/CD4 positive cells) as a biomarker to assess the immunomodulatory capability of UB421. The procedure for Quantification of Regulatory T cells is described below.

Blood collected in EDTA vacutainer was hemolyzed with lysing buffer at room temperature for 10 minutes then washed once with Stain buffer. Cells were stained with various antibodies for surface markers staining including Anti-CD4(D2)-FITC, Anti-CD25-APC and Anti-CD45-PerCP on ice for 30 min. Cells were then washed twice and stained for Anti-FoxP3-PE (BD Biosciences) according to the manufacturer's instructions. Cells were then washed twice and fixed with Fixation Buffer. Samples were acquired on FACSVerse flow cytometer. Data analysis was performed using FlowJo software V10.0.8. (6).

Figure 17A:
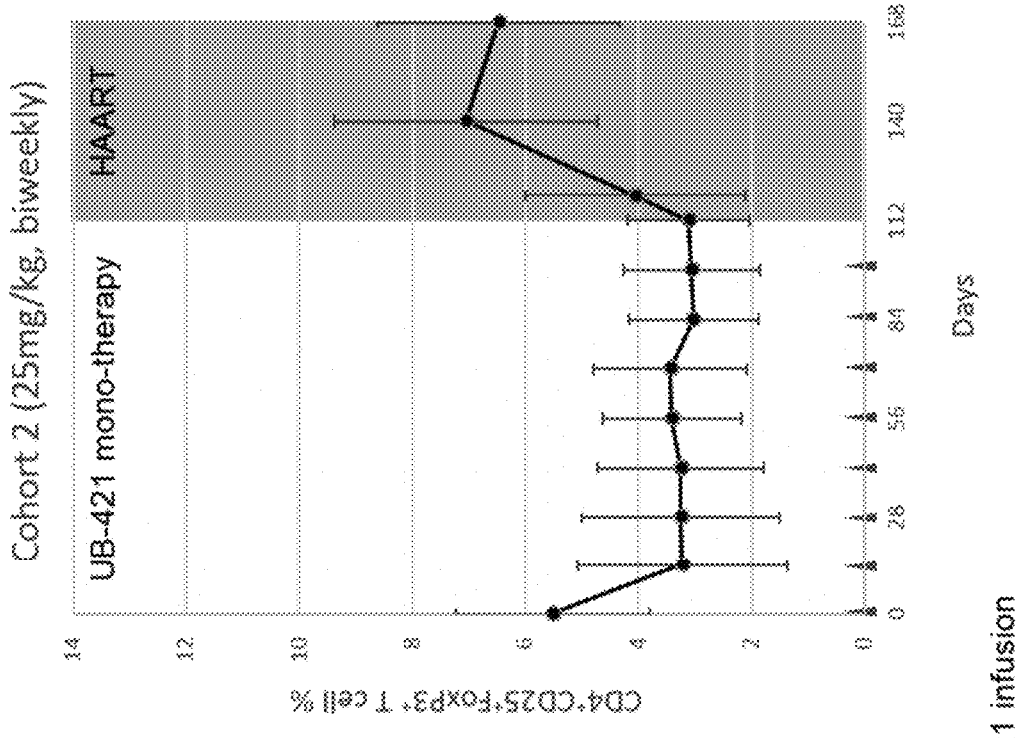
FIGS. 17A and 17B. Graphs showing CD4+CD25+ FoxP3+ T cell % out of total CD4+ cells representing the % Treg cells (mean and STD) for each time point (days of visit) in patients who received all administrations of either a 10 mg/kg of the study drug UB-421 (cohort 1, FIG. 17A) or 25 mg/kg of the study drug UB-421 (cohort 2, FIG. 17B) throughout the trial.
Figure 17B:
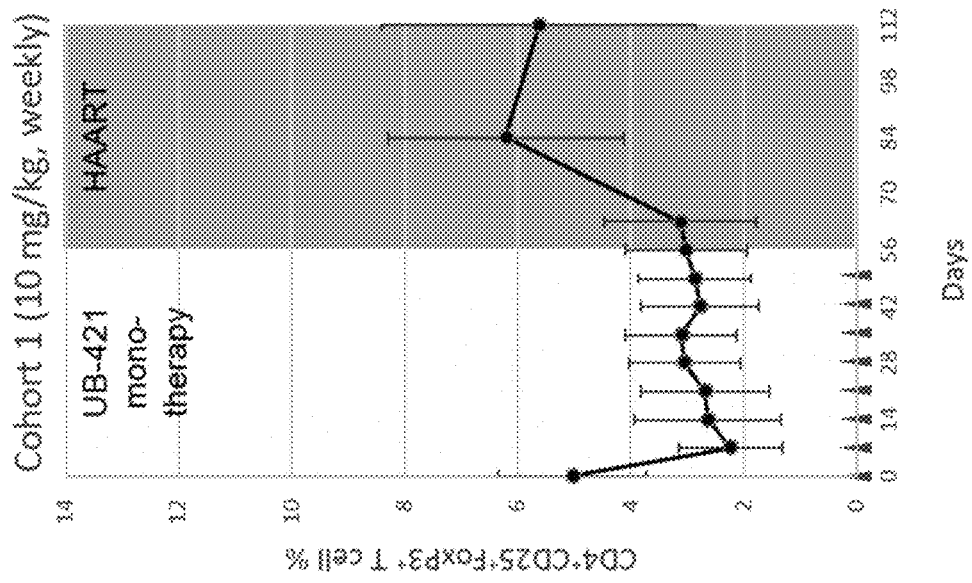

As shown in FIG. 17, the reduction level in % in Treg cells after V1 during treatment period (V2 to V8) is approximately half of V1 in average (44.4-59.6% and 52.4-65.3% in cohort 1 and cohort 2 respectively). After treatment period, the level of Treg cell % bounced over baseline at V11 (120.5% in cohort 1 while 120.1% in cohort 2) and returned to basaline at V12 in average (110.5% in cohort 1 while 110.2% in cohort 2).

5.3.4 Quantification of HIV-1 Proviral DNA.

HIV-1 Proviral DNA may provide another biomarker to monitor the HIV infected viral reservoir content in treated patients. We therefore established an assay for quantification of HIV-1 Proviral DNA as described below to conduct such monitoring for patients receiving UB421 who had reached a stabilized condition after HAART treatment.

5.3.5 Cell Isolation and DNA Extraction.

Peripheral blood mononuclear cells (PBMCs) were isolated by standard Ficoll-Hypaque density gradient centrifugation of patient's blood samples. Cellular DNA were extracted from purified PBMCs with ZR-Duet DNA/RNA Miniprep Plus Kit (Zymo Research) and stored at −80° C. until use. The numbers of PBMCs of each sample were counted before DNA extraction.

5.3.6 Quantification of HIV-1 Proviral DNA.

The primer and probe sequence and PCR procedures of semi-nested RealTime PCR were modified as shown below. Briefly, purified DNA and standard plasmid were directly subjected to two rounds of PCR which amplified a conserved region with HIV-1 gag motif. Extracted DNA was first amplified with 0.2 µM of each primer, GAG1 and SK431, by AmpliTaq Gold (Applied BioSystem) in a 25 µl reaction for 10 cycles on SimpliAmp Thermal Cycler (Applied Biosystems). The product of first PCR was subsequently used as template in the second quantification PCR amplification on a RealTime PCR machine using TaqMan detection chemistry. 2 µl product of the first PCR was used in the second PCR to amplify with 0.2 µM of each primer, GAG1 and GAG2, by TaqMan Fast Advanced Master Mix (Applied BioSystem) in a 20 µl reaction and the product of second PCR was detected by 0.2 µM of dual-labeled fluorescent probe, GAG3 on QuantStudio 5 RealTime PCR System (Applied BioSystem). A standard curve from $5 \times 10^6$ to $4 \times 10^1$ copies was generated with plasmid containing HIV-1 gag capsid region.

The cell numbers were determined by quantification PCR of albumin gene. The extracted DNA was amplified with 0.2 µM of each primer, Alb-F and Alb-R, by TaqMan Fast Advanced Master Mix (Applied BioSystem) in a 20 µl reaction and the product of second PCR was detected by 0.2 µM of dual-labeled fluorescent probe, Alb-P on QuantStudio 5 RealTime PCR System (Applied BioSystem). A standard curve from $2.5 \times 10^6$ to $4 \times 10^3$ copies was generated with plasmid containing Albumin.

All samples were run in duplicate. The results were displayed as copies of HIV proviral DNA per million PBMCs by normalized with cell number quantified by qPCR. The sequence of primers and probe are as followed:

SK431
(SEQ ID NO: 15)
5'-TGCTATGTCAGTTCCCCTTGGTTCTCT-3',

GAG1
(SEQ ID NO: 16)
5'-TCAGCCCAGAAGTAATACCCATGT-3',

GAG2
(SEQ ID NO: 17)
5'-CACTGTGTTTAGCATGGTGTTT-3',

GAG3
(SEQ ID NO: 18)
5'-FAM-ATTATCAGAAGGAGCCACCCCACAAGA-IBHQ-3',

Alb-F
(SEQ ID NO: 19)
5'-GCTGTCATCTCTTGTGGGCTGT-3',

Alb-R
(SEQ ID NO: 20)
5'-ACTCATGGGAGCTGCTGGTTC-3',

Alb-P
(SEQ ID NO: 21)
5'-FAM-GGAGAGATTTGTGTGGGCATG ACAGG-IBHQ-3'

5.3.7 Eradication of Cellular HIV DNA by UB-421.

Figure 18:
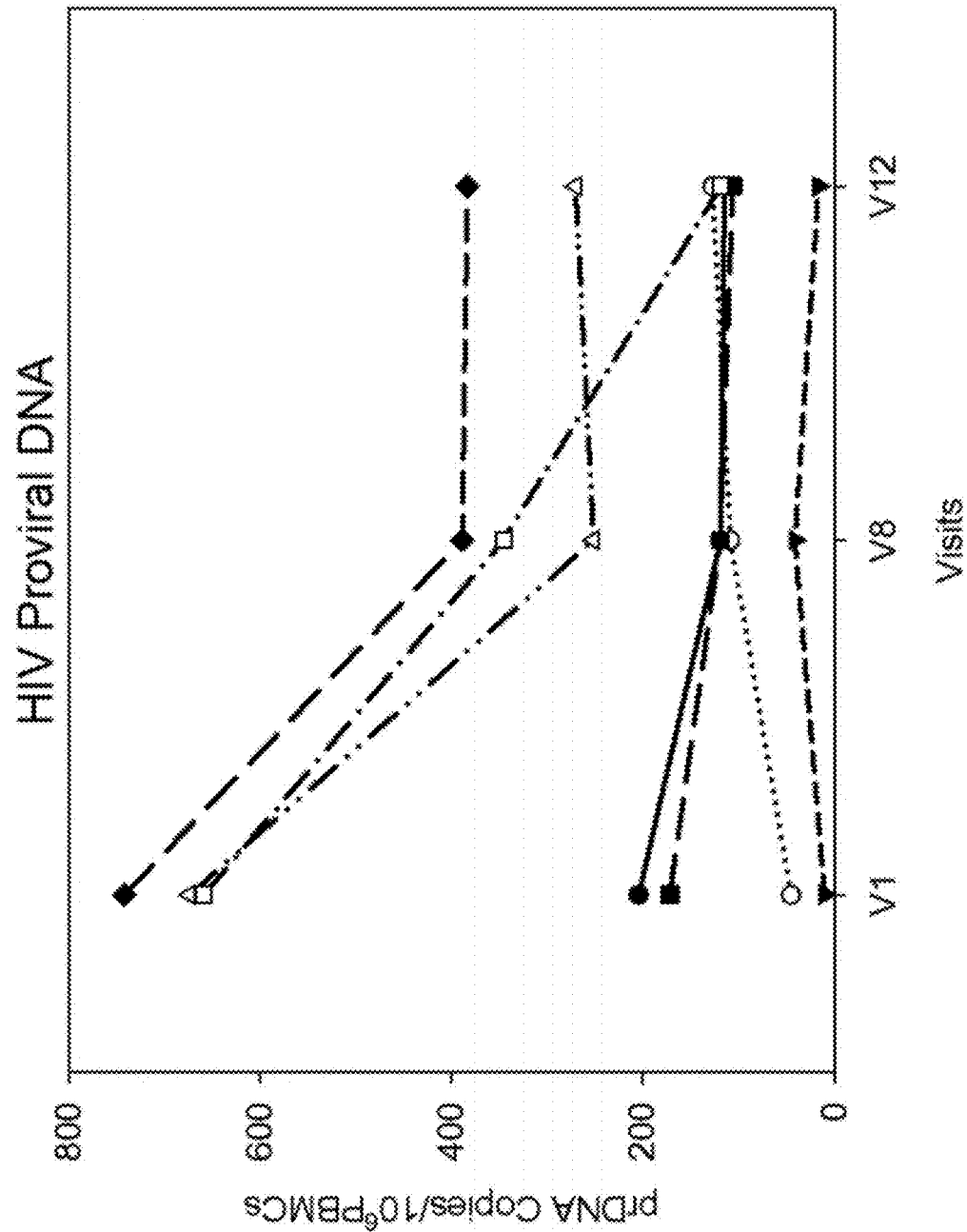
FIG. 18. PBMC HIV Proviral DNA content for individual patients who received all administrations of either a 10 mg/kg or 25 mg/kg of the study drug UB-421 measured at either the beginning (V1) or end (V8) of the treatment period, or at the end of the monitoring period when patients from V8 to V12 returned back to the original HAART treatment. Each line represents the results obtained from an individual patient.

In the UB-421 HAART replacement therapy trial, PBMCs was collected for DNA extraction and HIV proviral DNA quantification. The cellular HIV proviral DNA content was measured at V1 (before UB-421 treatment), V8 (end of UB-421 treatment) and V12 (end of follow-up). The HIV proviral DNA content was found significantly decreased after UB-421 treatment and then maintained at a similar level after patients returned to their original HAART treatment until 9 weeks after the last UB-421 administration (V12) in the seven subjects analyzed (FIG. 18). This result indicates that UB-421 treatment can further reduce both integrated and unintegrated cellular HIV proviral DNA in HAART treated and stabilizied patients, indicative of the potential of reduction of HIV viral reservoir cells as a result of the UB421 treatment. This represents another significant feature associated with UB421 beyond its important role as a potent HIV entry inhibitor.

5.4 Efficacy Results:

Viral rebound was defined as more than two consecutive detection of viral load above 400 HIV-1 RNA copies per mL serum or plasma. As shown in FIG. 16 for individual patients, except for a few blips which were detected occasionally at about the same frequency for HAART stabilizied patients during HAART treatment, complete viral suppression for below the 400 RNA copies/mL (dashed lines) was maintained throughout and beyond the treatment period. This marks a 100% efficacy in UB421 treatment as a replacement for HAART.

Figure 19:
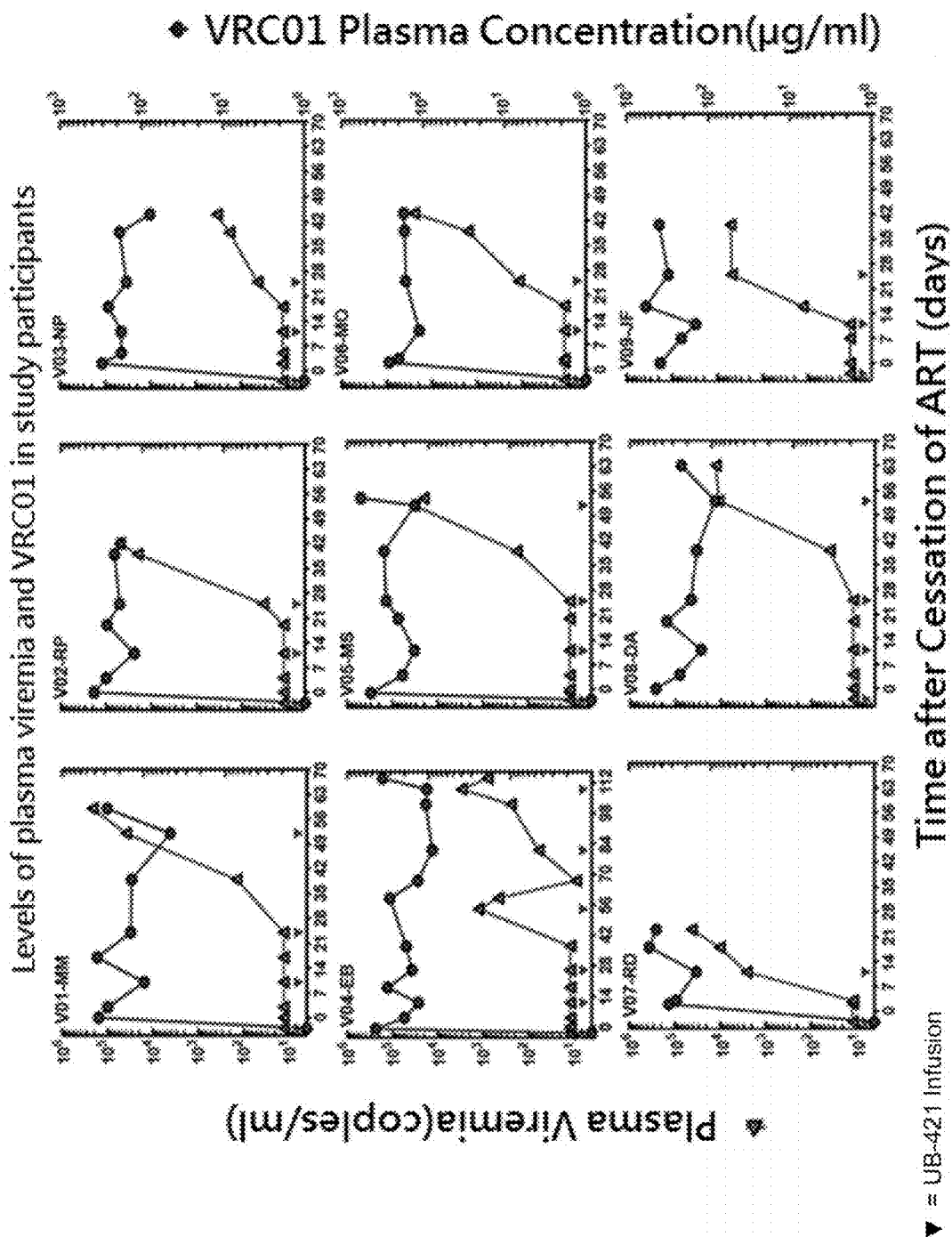
FIG. 19. Graphs for 9 patients are shown for levels of plasma viremia (solid triangle, HIV RNA copies/mL) and VRC01 antibody plasma concentration (solid circle, ug/ml) in HAART stabilized patients employing anti HIV gp120 broadly neutralizing antibody VRC01 monotherapy as a substitute for antiretroviral therapy. This NIH trial was terminated ahead of schedule as HIV suppression was not achieved despite of the presence of high VRC01 antibody plasma concentration serum. The upside down triangle above the x-axis represents a UB-421 infusion time point.

The ability to maintain 100% viral suppression for up to 16 weeks (cohort 2) treatment with UB421 is unprecedented when compared to a similar HAART replacement trial conducted by NIH using broadly neutralizing anti-gp120 monoclonal antibody VRC01 (NIH vaccine research center VRC01) when all (9 out of 9) patients (100%) failed in maintaining such suppression during the period of treatment from 11 to 86 days (FIG. 19). It is even more impressive when compared to all monotherapy treatment tested until now amongst HIV-1 drugs as shown in FIG. 20 when % of viral suppression is used as the end parameter.

As shown in FIG. 20, historic data for HIV drugs on the market indicates that only 50% of the patients maintained a viral suppression state up to 4 weeks. VRC 01-like anti gp120 broadly neutralizing antibodies show significant improvement upon the HIV-1 drugs in that 70% of patients receiving such monotherapy maintained viral suppression up to 4 weeks into the treatment where about 10% of pateints maintained viral suppression when treated up to 8 weeks. Pro140 as a CCR5 entry inhibitor provides a further improvement beyond the two mentioned above in that despite the inconvenience to excluding about 30% patients for trial entry due to patient's HIV-1 not using CCR5 as entry receptor, patients mainted a 98% viral suppression at 4 weeks, 82% suppression at 8 weeks and 75% suppression at 12 weeks. It is most impressive that UB421 as a monotherapy has demonstrated in this substitution trial that it maintained 100% suppression up to 16 weeks of treatment per the protocol tested. This unprecedented clinical outcome indicated a state of the art efficacy of viral entry inhibition (100%) as long as CD4 cells are fully coated; an impressive immunomodulatory effect as exemplified by reduction of % T reg cells during treatment and restoration in patients of both CD4 and CD8 cells (such as an increase in HIV gag responsive CD8 T cell proliferation) during treatment; —and the reduction of HIV DNA content upon UB421 treatment, indicative of reduction in viral reservoir cells.

FIG. 21 summarizes the factors that positively influence HIV-1 patients upon receiving UB421-like anti-CD4 treatment. For example, FIG. 21 shows that treatment with UB-421-like antibodies: (1) restores HIV-antigen specific T cell activity, as demonstrated in Examples 8 and 9, by reducing the % of T reg cells upon and during treatment, increasing the CD8+ cell count after treatment, and increasing the CD8+ proliferating cells in response to HIV gag motif peptide stimulation after treatment, all of which are indicative of enhanced functional HIV specific T cells that mediate CTL targeting at those HIV infected CD4 cells; (2) enhances T cell activation, as shown by enhanced TNF-alpha production, in particular in tissue follicular CD4 cells, where HIV reservoir T cells are enriched and such cells are densely packed; and (3) prevents cell-to-cell and cell-free infection by providing potent entry inhibition thus preventing new infection of CD4 positive cells. With the support of these three mechanisms, treatment with UB-421-like antibodies results in: (4) a reduction in HIV T cell reservoirs as evidenced by a reduction in HIV DNA content in blood cells measured. These four mechanisms as illustrated in FIG. 21 would lead to ultimate sustained virologic remission of HIV infection, or functional cure.

Example 10

Direct Activation of CD4+ Cells by UB421 as Detected by Phosphorylation and Activation of the TCR Signaling Kinase, LCK The effect of UB-421 on activation of CD4+ T cells via Lck kinase phosphorylation, which is a TCR proximal signaling molecule and known to bind directly to CD4 intracellular domain, was examined. The extent of Lck phosphorylation was evaluated by Western blot and flow cytometry analyses upon stimulation by UB-421 and other known T cell stimulators as a positive control (e.g. OKT3, anti-CD3).

The signal transduction of T cells is tightly regulated to ensure proper T cell activation and inhibition. Protein phosphorylation is the major way to transduce and enhance T cell receptor signaling (TCR signaling) upon antigen recognition. One kinase specifically expressed in T cells, Lymphocyte-specific protein tyrosine kinase (Lck), is critical in early TCR signal transduction and modulation. Lck is recruited to the TCR signaling complex through its association with co-receptor CD4 or CD8 and it phosphorylates the immunoreceptor tyrosine-based activation motifs (ITAMs) of CD3-zeta(ζ) chain and the zeta-chain-associated protein kinase 70 (Zap70), which in turn phosphorylates other proteins in the TCR signaling cascade leading to T cell activation.

Lck belongs to the Src tyrosine kinase family and is expressed exclusively in lymphoid cells, primarily in NK and T cells. The activity of Src kinase family is known to be controlled by two tyrosine phosphorylation sites, one enhances (Y394 for Lck) and one inhibits (Y505 for Lck) its kinase activity. The catalytic activity of Lck is regulated by a kinase and a phosphatase that control the phosphorylation status on Y505 and Y394. In CD4+ T cells, Lck exists in four different activity states, (1) unphosphorylated, (3) Y394 phosphorylated, (3) Y505 phosphorylated, and (4) dual-phosphorylated status without stimulation. Y394 is an auto-phosphorylation site and is linked to activation of the protein. Y505, which is located near the carboxyl terminus, is phosphorylated by Csk and dephosphorylation by CD45. The tertiary structure of Lck is folded during Y505 phosphorylation, which prevents the phosphorylation on site Y394. When CD45 dephosphorylates Y505, the tyrosine Y394 is auto-phosphorylated on Lck for kinase activity.

Upon T cell activation, active Lck is instantly recruited to immunological synapse and phosphorylates down-stream molecules. After the TCR binds to an antigen, is activated, and phosphorylates down-stream molecules including the CD3 chain and ZAP-70, Lck is quickly deactivated by (a) the dephosphorylation of Y394 through phosphatase PTPN22 and (b) the re-phosphorylation of Y505 through kinase, Csk. The dephosphorylation of Y394 at different time points following stimulation is indicative of activation of a T cell through TCR signaling cascades.

UB-421 binds to a conformational epitope near the CDR2 region on CD4 domain 1 to block HIV-1 binding and entry into cells. The effect of UB-421 on the TCR signal transduction cascade and immune regulation after binding to CD4 has been studied through the quantification of the phosphorylation of Y394 and Y505 of Lck by Western blots and flow cytometry analyses.

1 Materials and Methods 1.1 Primary CD4+ T Cell Preparation

Peripheral blood mononuclear cells (PBMCs) from normal healthy donors were first isolated by Ficoll-Hypaque (GE Healthcare) density gradient centrifugation. CD4+ T cells were then negatively selected by CD4 T Cell Isolation Kit (Miltenyi Biotec) from purified PBMCs.

1.2 Immunoblotting Analysis of Phospho-Lck

Two million ($2 \times 10^6$) Jurkat T cells or primary human T cells were washed twice with RPMI. All cells were stimulated in 1 ml of prewarmed RPMI with mAb UB-421 or anti-CD3 (OKT-3, BioLegend) at 5 µg/ml then cross-linked with 10 µg/ml streptavidin (Jackson ImmunoResearch) for "crosslinking" samples and incubated at 37° C. for the indicated time intervals. Stimulation was stopped by adding 1 ml of cold PBS and centrifugation to remove supernatant. Cell pellets were immediately frozen and stored at −80° C. until lysis.

Frozen cell pellets were lysed in 40 µL of Triton-X100 lysis buffer (1% (v/v)) in 20 mM Tris-HCl (pH 7.4) and 150 mM NaCl, with 10 µg/ml of aprotinin, 10 µg/ml leupeptin, 1 mM PMSF, 1 mM sodium orthovanadate, 1 mM sodium pyrophosphate, and 10 mM sodium fluoride. Lysates were centrifugated at 4° C. and 14,000 rpm for 7 minutes to remove debris. The cell extracts were fractionated on SDS-PAGE and transferred to polyvinylidene difluoride (PVDF) membrane (Bio-Rad). The membranes were probed with anti-phosph-Lck (Y394) (R&D Systems), anti-phosph-Lck (Y505) (R&D Systems) or anti-Lck (Abcam) followed by the addition of a suitable horseradish peroxidase-conjugated secondary antibody (Jackson ImmunoResearch). The signal was detected by Clarity™ chemiluminescent reagent (Bio-Rad), and a BioSpectrum 500 imaging system (UVP). All primary antibodies for immunoblot were used at 1:1,000 to 1:5,000 dilutions. The Lck Y394 and Y505 phosphorylation levels (density of band) were determined by using Vision-WorkLS 8.2 Imaging System software and normalized with the density of total Lck at each time point.

1.3 Flow Cytometry of Phospho-Lck

Isolated $CD4^+$ T cells were incubated in serum-free AIM-5 medium overnight before stimulation. The $CD4^+$ T cells were placed on ice and either 5 μg/mL of biotinylated anti-CD3 antibody (OKT-3, BioLegend) or UB-421 was added to the cells before incubating for an additional 10 minutes on ice. The cells were then stimulated with or without crosslinking at 37° C. for the indicated time. Crosslinking was achieved by adding purified streptavidin (BioLegend) to the biotinylated antibody before stimulating at 37° C. for the indicated time. Cells were then fixed immediately by Phosflow Fix Buffer (BD Biosciences) at 37° C. for 10 minutes and then permeabilized with Phosflow Perm/Wash Buffer (BD Biosciences). Cell were stained with PE-anti-Src (pY418) and Alexa Fluor 647-anti-Lck (pY505) (BD Biosciences) on ice. All samples were collected on BD FACSVerse flow cytometer (BD Biosciences). Data analysis was performed on FlowJo software V10.0.8 (Tree Star Inc., Ashland, Oreg.).

2 Results $CD4^+$ T cells were obtained from approximately 80 mL of normal healthy donors' blood. The blood samples were limited and the number of CD4+ T cells varied among donors. Thus, not all test conditions could be performed with the same donor's $CD4^+$ T cells. In several cases, the effect of UB-421 on Lck phosphorylation could only be evaluated under non-crosslinking conditions. The positive control was anti-CD3 (OKT3) tested under crosslinking condition, and the negative control was the untreated (medium only) sample.

2.1 Tyrosine Phosphorylation of Lck is Induced by UB-421 Binding on Jurkat T Cells.

Jurkat T cells were stimulated with UB-421 to evaluate its ability to induce Lck phosphorylation and downstream TCR signal transduction events. Stimulation with anti-CD3 antibody, a known stimulator of T cells, was used as a positive control. A previous experiment with flow cytometry demonstrated that 100% of Jurkat T cells expressed CD4 receptors on the cell surface.

As expected, the phospho-Y394 Lck levels were enhanced and peaked at the first timepoint, 5 min, in the anti-CD3-stimulated Jurkat T cells under crosslinking conditions (FIGS. 22A and 22B).

In cells stimulated with UB-421, Lck was phosphorylated under both crosslinking and non-crosslinking conditions in Jurkat cells and the phosphorylation level of Lck tyrosine Y394 was enhanced and peaked later at 15 min (FIGS. 22C and 22D).

2.2 Tyrosine Phosphorylation of Lck is Induced by UB-421 Binding on Primary CD4+ T Cells.

The effect of UB-421 binding to CD4 and TCR signaling was studied in primary CD4+ T cells.

$CD4^+$ T cells were isolated and purified to about 90-95% purity by negative selection. As a positive control, cells were stimulated with anti-CD3 antibody and the phosphorylation level of Lck Y394 was sustained as expected (FIGS. 23A and 23B).

Surprisingly, the tyrosine phosphorylation of both Lck Y394 and Y505 were enhanced in cells stimulated with UB-421 under both crosslinking conditions and non-crosslinking conditions (FIGS. 24A and 24B). The extent of phosphorylation of Lck Y394 in cells stimulated with UB-421 without crosslinking was slightly lower than those cells stimulated with UB-421 under crosslinking conditions from the same donors (Donor 1 and Donor 2) (FIG. 24A). The phosphorylated Y394-Lck peaked at 5 minutes for Donor 1 and 30 minutes for Donor 2 with or without crosslinking of UB-421 (FIG. 24A).

To further evaluate the stimulation ability of UB-421 without crosslinking, primary CD4+ T cells from additional donors (Donors 4 to 7) were tested by Western blot analysis. The activation (phosphorylation of Y394) and inhibition (phosphorylation of Y505) was observed in most donors tested (FIGS. 24a to 24D). The extent, time to peak, and duration of phosphorylation appear to vary significantly among individual donors (FIGS. 24C and 24D). For $CD4^+$ T cells treated with UB-421 without crosslinking, the peak phosphorylation level of Y394 ranged from 1 to 4 folds among donors and the time to peak ranged from 5 to 30 minutes after stimulation (FIGS. 24C and 24D).

The Lck phosphorylation induced by UB-421 was further evaluated by intracellular staining via flow cytometry to measure the Lck Y394 and Y505 phosphorylation on a single cell basis. As a positive control, cells were stimulated with anti-CD3 antibody under crosslinking conditions. In the positive control samples, Lck phosphorylation and dephosphorylation occurred rapidly to control the strength of TCR signaling (FIG. 25A, dotted line). In the negative control sample (without any treatment), both Y394 and Y505 phosphorylation level remained unchanged over time (FIG. 25A, solid line).

Primary $CD4^+$ T cells from two different donors (Donors 8 and 9) were treated with UB-421. Under crosslinking conditions, UB-421 was found to induce both Y394 and Y505 phosphorylation, similar to the positive control cells stimulated with anti-CD3 (FIG. 25B, dotted line). Under non-crosslinking conditions, UB-421 induced a lower Lck phosphorylation (FIG. 25B, solid line). In some cases, only the decreasing trend was observed because the activation occurred too quickly. The results demonstrated that the peak phosphorylation level of Y394 occurred earlier than Y505. FIG. 25B shows that the peak phosphorylation level of Y394 occurred around 3 minutes compared to 10 minutes with the Y505 phosphorylation. The results also show that the phosphorylation of Lck induced by the crosslinking of UB-421 reached the plateau later than anti-CD3 stimulation but with a similar level of phosphorylation compared to anti-CD3.

3 Discussion

The TCR signaling of $CD4^+$ T cells is tightly regulated to avoid unnecessary and uncontrolled immune responses. As a crucial kinase of TCR signaling, Lck activity is regulated both temporal and spatial. In this study, it is demonstrated that UB-421, an anti-CD4 antibody, is capable of activating $CD4^+$ T cells and inducing phosphorylation of Lck at Y394 (activation form) and Y505 (inhibitory form). Lck is activated in most of the donors' $CD4^+$ T cells without crosslinking of UB-421 by analyzing the Y394 phosphorylation of Lck; however, the extent of phosphorylation is lower compared to that for UB-421 treatment with crosslinking.

By flow cytometry analysis, we found that the activation tyrosine was first phosphorylated and reached plateau at 3 minutes following by the inhibitory tyrosine Y505 phosphorylation, which reached the plateau at around 10 minutes with crosslinked UB-421. It indicates that the Lck activity is first enhanced by the phosphorylation of Y394 then soon controlled by the inhibitory phosphorylation of Y505.

UB-421 has been evaluated in several clinical trials to treat chronic HIV infection and shown great efficacy on HIV viral suppression as monotherapy. By binding to CD4, UB-421 could also induce activation of TCR signaling cascade kinase, Lck under crosslinking or without crosslinking conditions. The effect of UB-421 treatment on the level, time to peak, and duration of Lck Y394 and Y505 phosphorylation differs from donor to donor. The current results suggest that UB-421 may have potential to modulate immune responses. By enhancing CD4+ T cell response, UB-421 may also control HIV infection through intrinsic immune response in addition to competitive inhibitory of HIV entry. This and further study of CD4+ T cell TCR signaling and immune responses induced by UB-421 may shed more light on the understanding of the additional mechanisms of UB-421 on controlling HIV infection.

4 Conclusion

The results from the current study demonstrate that binding of UB-421 to CD4 induces or enhances the phosphorylation of Lck on both activation tyrosine Y394 and inhibitory tyrosine Y505 in primary CD4+ T cells isolated from normal healthy donors.

The phosphorylation of Lck can be activated by UB-421 under crosslinking or no crosslinking conditions.

The extent, time to peak, and duration of Lck phosphorylation upon treatment with UB-421 vary amongst individual donors.

UB-421 can act as an immune modulator in addition to a potent HIV entry inhibitor.

TABLE 1

HIV Entry Inhibition Activities of monoclonal antibody B4
(Monogram BioScience PhenoSense ™ Assay)

| B4 MAb: non-B Clade Viruses | | | | B4 MAb: non-B Clade Viruses | | | |
|---|---|---|---|---|---|---|---|
| | Isolate | B4 Mab (µg/mL) | | | Isolate | B4 Mab (µg/mL) | |
| Clade | Name | IC50 | IC90 | Clade | Name | IC50 | IC90 |
| A | 92/RW/008 | 0.026 | 0.082 | D | 93/UG/086 | 0.015 | 0.052 |
| A | 92/RW/024 | 0.055 | 0.105 | D | 94/UG/105 | 0.021 | 0.073 |
| A | 93/RW/029 | 0.019 | 0.063 | D | 94/UG/114 | 0.015 | 0.054 |
| A | 93/UG/077 | 0.012 | 0.109 | D | 94/UG/117 | 0.017 | 0.063 |
| A | 94/UG/103 | 0.021 | 0.082 | D | 94/UG/118 | 0.020 | 0.066 |
| A | CA1 | 0.011 | 0.062 | D | CD1 | 0.016 | 0.047 |
| A | CA2 | 0.018 | 0.055 | E | 93/TH/057 | 0.023 | 0.079 |
| A | CA3 | 0.019 | 0.052 | E | 93/TH/305 | 0.021 | 0.069 |
| BF | 93/BR/019 | 0.013 | 0.046 | E | CMU06 | 0.026 | 0.088 |
| C | 10362 | 0.020 | 0.065 | E? | QZ4589 | 0.036 | 0.170 |
| C | 21068 | 0.011 | 0.053 | EA | 92/TH/005 | 0.012 | 0.054 |
| C | 10215-6 | 0.018 | 0.063 | EA | 92/TH/006 | 0.022 | 0.073 |
| C | 11657-3 | 0.025 | 0.067 | EA | 92/TH/007 | 0.013 | 0.061 |
| C | 20635-4 | 0.020 | 0.090 | EA | 92/TH/009 | 0.021 | 0.052 |
| C | 93/IN/101 | 0.016 | 0.047 | EA | 92/TH/019 | 0.022 | 0.063 |
| C | CC1 | 0.016 | 0.052 | EA | 92/TH/020 | 0.015 | 0.051 |
| C | CC10 | 0.015 | 0.053 | EA | 92/TH/021 | 0.017 | 0.052 |
| C | CC2 | 0.021 | 0.065 | EA | 92/TH/022 | 0.012 | 0.035 |
| C | CC3 | 0.012 | 0.049 | EA | 92/TH/024 | 0.010 | 0.048 |
| C | CC4 | 0.013 | 0.044 | EA | CMU02 | 0.011 | 0.041 |
| C | CC5 | 0.019 | 0.062 | F | 93/BR/020 | 0.024 | 0.069 |
| C | CC6 | 0.018 | 0.065 | F | CF2 | 0.016 | 0.053 |
| C | CC7 | 0.013 | 0.050 | F | CF3 | 0.024 | 0.081 |
| C | CC8 | 0.019 | 0.053 | F | CF4 | 0.019 | 0.055 |
| C | CC9 | 0.020 | 0.071 | F | CF5 | 0.018 | 0.060 |
| C | MW/93/959 | 0.019 | 0.050 | F | CF6 | 0.018 | 0.064 |
| C | MW/93/960 | 0.010 | 0.056 | F | CF7 | 0.019 | 0.064 |
| D | 92/UG/001 | 0.018 | 0.056 | F | CF8 | 0.017 | 0.079 |
| D | 92/UG/005 | 0.019 | 0.073 | G | CG1 | 0.018 | 0.071 |
| D | 92/UG/021 | 0.017 | 0.054 | G | CG2 | 0.027 | 0.081 |
| D | 92/UG/024 | 0.040 | 0.085 | G | CG3 | 0.016 | 0.045 |
| D | 92/UG/035 | 0.011 | 0.025 | G | CG4 | 0.013 | 0.037 |
| D | 92/UG/038 | 0.014 | 0.039 | J | CJ1 | 0.018 | 0.056 |
| D | 92/UG/046 | 0.015 | 0.042 | J | CJ2 | 0.019 | 0.063 |
| D | 92/UG/053 | 0.020 | 0.049 | CONTROLS | 92HT594 | 0.021 | 0.062 |
| D | 92/UG/065 | 0.015 | 0.044 | CONTROLS | JRCSF | 0.034 | 0.077 |
| D | 93/UG/067 | 0.016 | 0.080 | CONTROLS | JRFL | 0.074 | 0.152 |
| D | 93/UG/070 | 0.011 | 0.053 | | | | |
| D | 93/UG/082 | 0.016 | 0.059 | Average: IC50 = 0.018 µg/mL IC90 = 0.062 µg/mL | | | |

TABLE 2

Neutralizing Activities of Deimmunized B4 (dB4C7) in Comparison to Parental B4 (MT-2 Microplaque Assay)

| HIV-1 Isolate | Clade | B4 Antibody* | Antibody Conc (µg/mL) at 50% Inhibition | Antibody Conc (µg/mL) at 90% Inhibition |
|---|---|---|---|---|
| VL 135 | B | mAb dB4C7 | 0.06 | 0.19 |
| | | murine mAb B4 | 0.12 | 0.29 |

TABLE 2-continued

Neutralizing Activities of Deimmunized B4 (dB4C7)
in Comparison to Parental B4 (MT-2 Microplaque Assay)

| HIV-1 Isolate | Clade | B4 Antibody* | Antibody Conc (µg/mL) at 50% Inhibition | Antibody Conc (µg/mL) at 90% Inhibition |
|---|---|---|---|---|
| UG 029 | A | mAb dB4C7 | 0.5 | 1.88 |
|  |  | murine mAb B4 | 0.31 | 0.94 |
| UG 046 | D | mAb dB4C7 | 0.44 | 11 |
|  |  | murine mAb B4 | 0.43 | 5.7 |
| TH 036 | E | mAb dB4C7 | 0.19 | 0.56 |
|  |  | murine mAb B4 | 0.25 | 0.74 |
| USNG/98/31 | C | mAb dB4C7 | 0.08 | 0.22 |
|  |  | murine mAb B4 | 0.19 | 0.36 |

TABLE 3

Neutralizing Activities of Deimmunized B4 (dB4C7)
in Comparison to Parental B4 (PBMC Assay)

| HIV-1 Isolate | Clade | B4 Antibody* | Antibody Conc (µg/mL) at 50% Inhibition | Antibody Conc (µg/mL) at 90% Inhibition |
|---|---|---|---|---|
| ZA/98/009 | C | mAb dB4C7 | 0.04 | 0.08 |
|  |  | murine mAb B4 | 0.03 | 0.13 |
| CM 235 | E | mAb dB4C7 | 0.04 | 0.07 |
|  |  | murine mAb B4 | 0.02 | 0.1 |

TABLE 4

Monoclonal Antibody B4 Blocks Both Cell-free
and Cell-to-cell Transmission of HIV

| Virus strain | Titer for fusion inhibition (cell-to-cell) 50% | Titer for fusion inhibition (cell-to-cell) 90% | Titer for neutralization (cell-free) 50% | Titer for neutralization (cell-free) 90% |
|---|---|---|---|---|
| UG266 | 1:1060 | 1:140 | 1:280 | 1:136 |
| UG046 | 1:1479 | 1:245 | 1:628 | 1:234 |

TABLE 5

Sequential Staining by FACS Analysis - Percent Positive PBMC

| | Single Label Control | | 1st - Leu3a binding 2nd - B4 exposure | | | 1st - B4 binding 2nd - Leu3a exposure | | |
|---|---|---|---|---|---|---|---|---|
| | | | Leu3a+ | Leu3a− | Leu3a+ | Leu3a+ | Leu3a− | Leu3a+ |
| | Leu3a+ | B4+ | B4− | B4+ | B4+ | B4− | B4+ | B4+ |
| X282 | 25.5 | 26.1 | 0.1 | 0.8 | 24.5 | 0.0 | 21.9 | 1.2 |
| X301 | 44.0 | 45.5 | 0.3 | 0.6 | 46.7 | 0.0 | 42.7 | 3.0 |

TABLE 6

TNF-α Levels and HIV-1 Viral Load in PBMC Culture

| Stimulator | TNF-α conc. (pg/ml) D0 | D2 | D7 | Viral load (copies/ml) D0 | D2 | D7 | Viral load % change (Normalized to Medium) D0 | D2 | D7 | Cell count (×10$^6$)/ Viability (%) D0 | D2 | D7 |
|---|---|---|---|---|---|---|---|---|---|---|---|---|
| Medium only (control) | ND | ND | ND | 82 | 37731 | 24905 | 100 | 100 | 100 | 11.86/ 92.4 | 2.13/ 94.4 | 0.84/ 98.4 |
| mAb dB4 | ND | 546.7 | 349.5 | 99 | 57162 | 54797 | 121 | 151 | 220 | 11.98/ 89.2 | 2.00/ 91.7 | 1.02/ 77.1 |
| PMA + PHA | ND | 2593.1 | 1030 | 344 | 20738 | 19465 | 420 | 55 | 78 | 11.71/ 93.4 | 1.32/ 85.2 | 5.20/ 92.0 |

ND: Non-Detectable

TABLE 7

Viral Load Reduction After Multiple Administrations of UB-421
in Phase IIa Trial

| Endpoint | Cohort 1 (10 mg/kg weekly) ITT N = 14 | Cohort 1 (10 mg/kg weekly) PP N = 7 | Cohort 2 (25 mg/kg bi-weekly) ITT N = 15 | Cohort 2 (25 mg/kg bi-weekly) PP N = 11 |
|---|---|---|---|---|
| Mean (SD) max. VL reduction Log$_{10}$ copies/ml | −2.27 (0.60) | −2.73 (0.34) | 2.45 (0.46) | −2.47 (0.45) |

TABLE 7-continued

Viral Load Reduction After Multiple Administrations of UB-421 in Phase IIa Trial

| Endpoint | Cohort 1 (10 mg/kg weekly) | | Cohort 2 (25 mg/kg bi-weekly) | |
|---|---|---|---|---|
| | ITT N = 14 | PP N = 7 | ITT N = 15 | PP N = 11 |
| Maximal individual VL reduction $Log_{10}$ copies/ml | | −3.23 | | −3.28 |
| n (%) >1 $Log_{10}$ VL reduction | 14 (100%) | 7 (100%) | 15 (100%) | 11 (100%) |
| n (%) <200 copies/ml | 8 (57.1%) | 5 (71.4%) | 10 (66.7%) | 7 (63.6%) |
| n (%) <50 copies/ml | 3 (21.4%) | 3 (42.9%) | 3 (20.0%) | 2 (18.2%) |
| n (%) <20 copies/ml | | 3 (42.9%) | | 2 (18.2%) |

ITT: Intent-to-Treat Population
PP: Per-Protocol Population
VL: Viral Load

TABLE 8

Design of UB-421 Treatment in Functional Cure

Potential Advantage of UB-421 over HAART drugs:

UB-421 blocks cell-to-cell transmission of HIV-1 viruses
UB-421 cross-links CDR2-like loop of CD4 and activates cells and thus the HIV-1 in latency Goals:

To provide an effective protection, in addition to HAART, by blocking both cell-free and cell-to-cell transmission
To develop a functional cure strategy for HIV-infected patients either with no previous treatment or who are currently on stable antiretroviral therapy Objectives:

To evaluate the potency of cycling treatment of UB-421 with continuous HAART in reducing the size of the latent viral reservoir and curing HIV-1-infected patients Study type:

Interventional

Study Design:

Single group assessment; open-label
Assigned interventions:

Two cycles of 8 doses of 25 mg/kg UB-421 administered bi-weekly by intravenous infusion on days 1, 15, 29, 43, 57, 71, 85 and 99 for a period of 4 months followed by 2 months of background HAART alone will be provided to HIV-1 infected patients.
Upon completion of one year study period, additional observational study will be conducted and conditioned by:
Completion of 2 cycles of UB-421 in combination with HAART in one year study
Significant reduction in viral reservoir
CD4+ T-cell count >500/mm$^3$
In the additional observational study, the background HAART will be interrupted to evaluate:
time to viremia >1,000 copies/ml
time to meet criteria to restart HAART

---

The invention claimed is:

1. An antibody directed against a CD4 molecule, wherein the antibody comprises:
   a heavy chain comprising an amino acid sequence of SEQ ID NO: 10; and
   a light chain comprising an amino acid sequence of SEQ ID NO: 8, and wherein
   the antibody specifically binds to an extracellular region of the CD4 molecule, and wherein
   when the antibody is bound to the CD4 molecule on the surface of a CD4+ cell, the antibody:
   a) competitively inhibits HIV entry into the CD4+ cell;
   b) activates latent HIV reservoirs in a resting CD4+ cell infected with HIV;
   (c) reduces levels of cellular HIV DNA; and
   (d) provides sustained virologic remission of HIV infection without viral load rebound.

2. The antibody according to claim 1, wherein the antibody competitively inhibits cell-free and cell-to-cell transmission of HIV.

3. The antibody according to claim 1, wherein the antibody reduces the percentage of regulatory T cells when administered to a subject.

4. The antibody according to claim 1, wherein the antibody increases the amount of CD8+ cells when administered to a subject.

5. The antibody according to claim 1, wherein the antibody increases CD8+ proliferating cells in response to HIV gag motif peptide stimulation when administered to a subject.

6. The antibody according to claim 1, wherein the antibody enhances functional HIV specific CD8+ CTL cells that target an HIV infected CD4+ cell when administered to a subject.

7. The antibody according to claim 1, wherein the antibody enhances TNF-alpha production in CD4+ cell.

8. The antibody according to claim 1, wherein the antibody activates a resting CD4+ cells with or without cross-linking.

9. The antibody according to claim 1, wherein the antibody reduces HIV viral load in an HIV positive patient to less than 50 copies per milliliter of blood without viral load rebound.

10. The antibody of claim 1, wherein the antibody binds to a region around domain 1 of the CD4 molecule.

11. The antibody of claim 1, wherein the antibody binds to a region around the CDR2 region in domain 1 of CD4.

12. The antibody of claim 1, wherein the antibody comprises
   a heavy chain variable region amino acid sequence comprising:
   CDR1 of SEQ ID NO: 1,
   CDR2 of SEQ ID NO: 2, and
   CDR3 of SEQ ID NO: 3; and
   a light chain variable region amino acid sequence comprising:
   CDR1 of SEQ ID NO: 4,
   CDR2 of SEQ ID NO: 5, and
   CDR3 of SEQ ID NO: 6.

13. The antibody of claim 1, wherein the antibody is a monoclonal antibody.

14. The antibody of claim 1, wherein the antibody is a humanized monoclonal antibody.

15. The antibody of claim 1, wherein the antibody is a humanized monoclonal antibody comprising:
   a heavy chain comprising an amino acid sequence of SEQ ID NO: 9; and
   a light chain comprising an amino acid sequence of SEQ ID NO: 8.

16. The antibody of claim 1, wherein the antibody is a humanized monoclonal antibody comprising:
   a heavy chain comprising an amino acid sequence of SEQ ID NO: 7; and
   a light chain comprising an amino acid sequence of SEQ ID NO: 8.

17. The antibody of claim 1 having an absolute binding affinity (Kd) to membrane-bound CD4 on HPB-ALL cells between about $3.1 \times 10^{-11}$ M to about $8.1 \times 10^{-11}$ M.

18. The antibody of claim 1 bound to a CD4 molecule.

19. A composition comprising the antibody of claim 1.

20. A pharmaceutical composition comprising the antibody of claim 1 and a pharmaceutically acceptable carrier.

21. A pharmaceutical composition comprising the antibody of claim 1 in phosphate buffer saline (PBS), 20 mM glycine, and 0.05% (v/v) polysorbate 20.

22. A pharmaceutical composition comprising the antibody of claim 1 in phosphate buffer saline (PBS), 20 mM glycine, 0.05% (v/v) polysorbate 20, and 10 mM histidine.

23. A pharmaceutical composition comprising about 1.0 mg/mL to about 200.0 mg/mL of the antibody of claim 1 in phosphate buffer saline (PBS), 20 mM glycine, and 0.05% (v/v) polysorbate 20.

24. A pharmaceutical composition comprising about 1.0 mg/mL to about 200.0 mg/mL of the antibody of claim 1 in phosphate buffer saline (PBS), 20 mM glycine, 0.05% (v/v) polysorbate 20, and 10 mM histidine.

25. A pharmaceutical composition comprising about 10.0 mg/mL of the antibody of claim 1 in phosphate buffer saline (PBS), 20 mM glycine, and 0.05% (v/v) polysorbate 20.

26. A pharmaceutical composition comprising about 10.0 mg/mL of the antibody of claim 1 in phosphate buffer saline (PBS), 20 mM glycine, 0.05% (v/v) polysorbate 20, and 10 mM histidine.

27. A pharmaceutical composition comprising the antibody of claim 15 and a pharmaceutically acceptable carrier.

28. A pharmaceutical composition comprising the antibody of claim 16 and a pharmaceutically acceptable carrier.

29. A method for treating a subject exposed to HIV comprising:
   administering to the subject a pharmacologically effective amount of the antibody of claim 1.

30. The method of claim 29, wherein the antibody is administered to the subject prior to exposure to HIV.

31. The method according to claim 29, wherein the antibody is administered to the subject after exposure to HIV.

32. The method according to claim 29, wherein the antibody is administered within 48 hours after exposure to HIV.

33. The method according to claim 29, wherein the antibody is administered to the subject at a dosage of at least about 5 mg/kg body weight.

34. The method according to claim 33, wherein the antibody is administered to the subject multiple times.

35. The method according to claim 34, wherein the antibody is administered to the subject in a weekly, bi-weekly, or monthly interval.

36. The method according to claim 34, further comprising a step of administering an antiviral agent to the subject.

37. The method according to claim 36, wherein the antiviral agent is a highly active antiretroviral therapy (HAART).

38. The method according to claim 37, wherein HAART comprises a nucleoside analogue reverse transcriptase inhibitor in combination with a protease inhibitor or a non-nucleoside reverse transcriptase inhibitor.

39. The method according to claim 37, wherein the antibody is administered concurrently with HAART.

40. The method according to claim 37, wherein the antibody and HAART are administered to the subject over the course of a cycle, wherein the cycle comprises:
   i) administering the antibody to the subject for a first period of time followed by a treatment holiday for a second period of time; and
   ii) administering HAART to the subject continuously during the first period of time and the second period of time in (i).

41. The method according to claim 37, wherein the antibody and HAART are administered to the subject over the course of a cycle, wherein the cycle comprises:
   i) administering the antibody to the subject for a period of four months in a weekly, bi-weekly, or monthly interval followed by a two month treatment holiday; and
   ii) administering HAART to the subject continuously during the six-month period in (i).

42. The method according to claim 40, wherein the subject is treated over the course of two cycles.

43. The method according to claim 41, wherein the subject is treated over the course of two cycles.

44. The method according to claim 37, wherein the antibody is administered at a time that is not concurrent with HAART.

45. The method according to claim 37, wherein the antibody and HAART are administered to the subject over the course of a cycle, wherein the cycle comprises:
   i) administering the antibody to the subject for a first period of time followed by a treatment holiday for a second period of time; and
   ii) administering HAART to the subject during the second period of time and not during the first period of time.

46. The method according to claim 45, wherein the antibody is administered in regular intervals during the first time period.

47. The method according to claim 45, wherein the antibody is administered in weekly, bi-weekly, or monthly intervals during the first time period.

48. A method for treating a subject with HIV infection, comprising administering to the subject a treatment regimen comprising:
   a) a pharmacologically effective amount of the antibody of claim 1; and
   b) a highly active antiretroviral therapy (HAART).

49. The method of claim 48, wherein the antibody is administered to the subject at a dosage of at least about 5 mg/kg body weight.

50. The method according to claim 48, wherein the antibody and HAART are administered to the subject over the course of a cycle, wherein the cycle comprises:
   i) administering the antibody to the subject for a first period of time followed by a treatment holiday for a second period of time; and
   ii) administering HAART to the subject continuously during the first period of time and the second period of time in (i).

51. The method according to claim 48, wherein the antibody and HAART are administered to the subject over the course of a cycle, wherein the cycle comprises:
   i) administering the antibody to the subject for a period of four months in a weekly, bi-weekly, or monthly interval followed by a two-month treatment holiday; and
   ii) administering HAART to the subject continuously during the six-month period in (i).

52. The method according to claim 50, wherein the subject is treated over the course of two or more cycles.

53. The method according to claim 51, wherein the subject is treated over the course of two or more cycles.

54. The method according to claim 51, wherein the antibody and HAART are administered to the subject over the course of a cycle, wherein the cycle comprises:
   i) administering the antibody to the subject for a period of four months in a weekly, bi-weekly, or monthly interval followed by a two-month treatment holiday; and
   ii) administering HAART to the subject continuously during the six-month period in (i).

55. The method according to claim 48, wherein the antibody in (a) is administered at a time that is not concurrent with HAART in (b).

56. The method according to claim 48, wherein the antibody in (a) and HAART in (b) are administered to the subject over the course of a cycle, wherein the cycle comprises:
   i) administering the antibody to the subject for a first period of time followed by a treatment holiday for a second period of time; and
   ii) administering HAART to the subject during the second period of time and not during the first period of time.

57. The method according to claim 56, wherein the antibody is administered in regular intervals during the first time period.

58. The method according to claim 56, wherein the antibody is administered in weekly, bi-weekly, or monthly intervals during the first time period.

59. A method for inhibiting HIV entry into a CD4+ cell, comprising
   exposing the antibody of claim 1 to the cell.

60. A method for inhibiting gp120 binding to a CD4+ cell, comprising
   exposing the antibody of claim 1 to the cell.

61. A method for activating a resting CD4+ T cell, comprising
   exposing the antibody of claim 1 to the cell.

62. A method for activating a latent reservoir of HIV in a resting T cell, comprising
   exposing the antibody of claim 1 to the cell.

63. A method for reducing latent HIV reservoirs in a sample of cells infected with HIV, comprising
   a) exposing the antibody of claim 1 to the sample of cells; and
   b) exposing HAART to the sample of cells.

* * * * *

SEQUENCE LISTING

```
<160> NUMBER OF SEQ ID NOS: 22

<210> SEQ ID NO 1
<211> LENGTH: 5
<212> TYPE: PRT
<213> ORGANISM: Artificial Sequence
<220> FEATURE:
<223> OTHER INFORMATION: Murine Antibody
<220> FEATURE:
<221> NAME/KEY: DOMAIN
<222> LOCATION: (1)..(5)
<223> OTHER INFORMATION: CDR1 of heavy chain of murine antibody B4

<400> SEQUENCE: 1

Asp Tyr Val Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Murine Antibody
```

```
<220> FEATURE:
<221> NAME/KEY: DOMAIN
<222> LOCATION: (1)..(17)
<223> OTHER INFORMATION: CDR2 of heavy chain of murine antibody B4

<400> SEQUENCE: 2

Glu Ile Tyr Pro Gly Ser Gly Ser Ala Tyr Ser Asn Ala Lys Phe Lys
1               5                   10                  15

Asp

<210> SEQ ID NO 3
<211> LENGTH: 9
<212> TYPE: PRT
<213> ORGANISM: Artificial Sequence
<220> FEATURE:
<223> OTHER INFORMATION: Murine Antibody
<220> FEATURE:
<221> NAME/KEY: DOMAIN
<222> LOCATION: (1)..(9)
<223> OTHER INFORMATION: CDR3 of heavy chain of murie antibody B4

<400> SEQUENCE: 3

Arg Gly Asn Gly Thr Gly Phe Ala Tyr
1               5

<210> SEQ ID NO 4
<211> LENGTH: 15
<212> TYPE: PRT
<213> ORGANISM: Artificial Sequence
<220> FEATURE:
<223> OTHER INFORMATION: Murine Antibody
<220> FEATURE:
<221> NAME/KEY: DOMAIN
<222> LOCATION: (1)..(15)
<223> OTHER INFORMATION: CDR1 of light chain of murine antibody B4

<400> SEQUENCE: 4

Lys Ala Gly Gln Ser Val Asp Tyr Asp Gly Asp Ser Tyr Met Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Murine Antibody
<220> FEATURE:
<221> NAME/KEY: DOMAIN
<222> LOCATION: (1)..(7)
<223> OTHER INFORMATION: CDR2 of light chain of murine antibody B4

<400> SEQUENCE: 5

Val Ala Ser Asn Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Murine Antibody
<220> FEATURE:
<221> NAME/KEY: DOMAIN
<222> LOCATION: (1)..(9)
<223> OTHER INFORMATION: CDR3 of light chain of murine antibody B4

<400> SEQUENCE: 6

Gln Gln Ser Tyr Lys Asp Pro Leu Thr
1               5
```

<210> SEQ ID NO 7
<211> LENGTH: 448
<212> TYPE: PRT
<213> ORGANISM: Artificial Sequence
<220> FEATURE:
<223> OTHER INFORMATION: Humanized Antibody
<220> FEATURE:
<221> NAME/KEY: DOMAIN
<222> LOCATION: (1)..(448)
<223> OTHER INFORMATION: Heavy Chain of deimmunized human antibody B4
      [UB421] with identical CDRs1, 2 and 3 derived from the
      corresponding CDRs1, 2 and 3 from the heavy chain sequence of the
      parental murine B4 antibody

<400> SEQUENCE: 7

```
Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Val Ile His Trp Val Lys Gln Ala Thr Gly Gln Gly Leu Glu Trp Ile
        35                  40                  45

Gly Glu Ile Tyr Pro Gly Ser Gly Ser Ala Tyr Ser Asn Ala Lys Phe
    50                  55                  60

Lys Asp Arg Val Thr Met Thr Ala Asp Lys Ser Ser Asn Thr Ala Tyr
65                  70                  75                  80

Met Glu Leu Ser Ser Leu Thr Ser Asp Asp Thr Ala Val Tyr Phe Cys
                85                  90                  95

Ala Arg Arg Gly Asn Gly Thr Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr His Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
```

```
                    325                 330                 335
Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 8
<211> LENGTH: 218
<212> TYPE: PRT
<213> ORGANISM: Artificial Sequence
<220> FEATURE:
<223> OTHER INFORMATION: Humanized Antibody
<220> FEATURE:
<221> NAME/KEY: DOMAIN
<222> LOCATION: (1)..(218)
<223> OTHER INFORMATION: Light Chain of deimmuized human antibody B4
      [UB421] with identical CDRs1, 2 and 3 derived from the
      corresponding CDRs1, 2,and 3 from the light chain sequence of the
      parental murine B4 antibody

<400> SEQUENCE: 8

Asp Ile Val Leu Thr Gln Ser Pro Ala Ser Leu Ala Val Ser Leu Gly
1               5                   10                  15

Gln Arg Ala Thr Ile Thr Cys Lys Ala Gly Gln Ser Val Asp Tyr Asp
                20                  25                  30

Gly Asp Ser Tyr Met Asn Trp Tyr Gln Gln Lys Pro Gly Gln Pro Pro
                35                  40                  45

Lys Leu Leu Ile Tyr Val Ala Ser Asn Leu Glu Ser Gly Ile Pro Ala
                50                  55                  60

Arg Phe Ser Gly Ser Gly Ser Gly Thr Asp Phe Thr Leu Asn Ile His
65                  70                  75                  80

Pro Val Glu Glu Asn Asp Ala Ala Thr Tyr Tyr Cys Gln Gln Ser Tyr
                85                  90                  95

Lys Asp Pro Leu Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
                130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Leu Tyr Ala Cys Glu Val Thr His Gln Gly Leu Ser Ser Pro
                195                 200                 205
```

Val Thr Lys Ser Phe Asn Arg Gly Glu Cys
    210                 215

<210> SEQ ID NO 9
<211> LENGTH: 448
<212> TYPE: PRT
<213> ORGANISM: Artificial Sequence
<220> FEATURE:
<223> OTHER INFORMATION: Humanized Antibody
<220> FEATURE:
<221> NAME/KEY: DOMAIN
<222> LOCATION: (1)..(448)
<223> OTHER INFORMATION: Heavy Chain of the deimmunized human antibody
      B4 [UB421] with M253Y/S255T/T257E substitutions

<400> SEQUENCE: 9

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Val Ile His Trp Val Lys Gln Ala Thr Gly Gln Gly Leu Glu Trp Ile
        35                  40                  45

Gly Glu Ile Tyr Pro Gly Ser Gly Ser Ala Tyr Ser Asn Ala Lys Phe
    50                  55                  60

Lys Asp Arg Val Thr Met Thr Ala Asp Lys Ser Ser Asn Thr Ala Tyr
65                  70                  75                  80

Met Glu Leu Ser Ser Leu Thr Ser Asp Asp Thr Ala Val Tyr Phe Cys
                85                  90                  95

Ala Arg Arg Gly Asn Gly Thr Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr His Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr

```
                        325                 330                 335
Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 10
<211> LENGTH: 448
<212> TYPE: PRT
<213> ORGANISM: Artificial Sequence
<220> FEATURE:
<223> OTHER INFORMATION: Humanized Antibody
<220> FEATURE:
<221> NAME/KEY: SITE
<222> LOCATION: (253)..(253)
<223> OTHER INFORMATION: M or Y
<220> FEATURE:
<221> NAME/KEY: SITE
<222> LOCATION: (255)..(255)
<223> OTHER INFORMATION: S or T
<220> FEATURE:
<221> NAME/KEY: SITE
<222> LOCATION: (257)..(257)
<223> OTHER INFORMATION: T or E
<220> FEATURE:
<221> NAME/KEY: SITE
<222> LOCATION: (298)..(298)
<223> OTHER INFORMATION: N or H

<400> SEQUENCE: 10

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Val Ile His Trp Val Lys Gln Ala Thr Gly Gln Gly Leu Glu Trp Ile
        35                  40                  45

Gly Glu Ile Tyr Pro Gly Ser Gly Ser Ala Tyr Ser Asn Ala Lys Phe
    50                  55                  60

Lys Asp Arg Val Thr Met Thr Ala Asp Lys Ser Ser Asn Thr Ala Tyr
65                  70                  75                  80

Met Glu Leu Ser Ser Leu Thr Ser Asp Asp Thr Ala Val Tyr Phe Cys
                85                  90                  95

Ala Arg Arg Gly Asn Gly Thr Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

-continued

```
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Xaa Ile Xaa Arg
                245                 250                 255

Xaa Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Xaa Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 11
<211> LENGTH: 118
<212> TYPE: PRT
<213> ORGANISM: Artificial Sequence
<220> FEATURE:
<223> OTHER INFORMATION: Humanized Antibody

<400> SEQUENCE: 11

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Val Ile His Trp Val Lys Gln Ala Thr Gly Gln Gly Leu Glu Trp Ile
            35                  40                  45

Gly Glu Ile Tyr Pro Gly Ser Gly Ser Ala Tyr Ser Asn Ala Lys Phe
        50                  55                  60

Lys Asp Arg Val Thr Met Thr Ala Asp Lys Ser Ser Asn Thr Ala Tyr
65                  70                  75                  80
```

```
Met Glu Leu Ser Ser Leu Thr Ser Asp Asp Thr Ala Val Tyr Phe Cys
                85                  90                  95

Ala Arg Arg Gly Asn Gly Thr Gly Phe Ala Tyr Trp Gly Gln Gly Thr
            100                 105                 110

Leu Val Thr Val Ser Ser
        115

<210> SEQ ID NO 12
<211> LENGTH: 330
<212> TYPE: PRT
<213> ORGANISM: Artificial Sequence
<220> FEATURE:
<223> OTHER INFORMATION: Humanized Antibody
<220> FEATURE:
<221> NAME/KEY: SITE
<222> LOCATION: (135)..(135)
<223> OTHER INFORMATION: M or Y
<220> FEATURE:
<221> NAME/KEY: SITE
<222> LOCATION: (137)..(137)
<223> OTHER INFORMATION: S or T
<220> FEATURE:
<221> NAME/KEY: SITE
<222> LOCATION: (139)..(139)
<223> OTHER INFORMATION: T or E
<220> FEATURE:
<221> NAME/KEY: SITE
<222> LOCATION: (180)..(180)
<223> OTHER INFORMATION: N or H

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Xaa Ile Xaa Arg Xaa Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Xaa Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 111
<212> TYPE: PRT
<213> ORGANISM: Artificial Sequence
<220> FEATURE:
<223> OTHER INFORMATION: Humanized Antibody

<400> SEQUENCE: 13

Asp Ile Val Leu Thr Gln Ser Pro Ala Ser Leu Ala Val Ser Leu Gly
1               5                   10                  15

Gln Arg Ala Thr Ile Thr Cys Lys Ala Gly Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Asn Asp Ala Ala Thr Tyr Tyr Cys Gln Gln Ser Tyr
                85                  90                  95

Lys Asp Pro Leu Thr Phe Gly Gln Gly Thr Lys Leu Glu Ile Lys
            100                 105                 110

<210> SEQ ID NO 14
<211> LENGTH: 107
<212> TYPE: PRT
<213> ORGANISM: Artificial Sequence
<220> FEATURE:
<223> OTHER INFORMATION: Humanized Antibody

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105

-continued

<210> SEQ ID NO 15
<211> LENGTH: 27
<212> TYPE: DNA
<213> ORGANISM: Artificial Sequence
<220> FEATURE:
<223> OTHER INFORMATION: SK431 Primer Sequence

<400> SEQUENCE: 15
tgctatgtca gttccccttg gttctct 27

<210> SEQ ID NO 16
<211> LENGTH: 24
<212> TYPE: DNA
<213> ORGANISM: Artificial Sequence
<220> FEATURE:
<223> OTHER INFORMATION: GAG1 Primer Sequence

<400> SEQUENCE: 16
tcagcccaga agtaataccc atgt 24

<210> SEQ ID NO 17
<211> LENGTH: 22
<212> TYPE: DNA
<213> ORGANISM: Artificial Sequence
<220> FEATURE:
<223> OTHER INFORMATION: GAG2 Primer Sequence

<400> SEQUENCE: 17
cactgtgttt agcatggtgt tt 22

<210> SEQ ID NO 18
<211> LENGTH: 27
<212> TYPE: DNA
<213> ORGANISM: Artificial Sequence
<220> FEATURE:
<223> OTHER INFORMATION: GAG3 Primer Sequence
<220> FEATURE:
<221> NAME/KEY: misc_feature
<222> LOCATION: (1)..(1)
<223> OTHER INFORMATION: Fluorescein Amidite (FAM)
<220> FEATURE:
<221> NAME/KEY: misc_feature
<222> LOCATION: (27)..(27)
<223> OTHER INFORMATION: Iowa Black Hole Quencher (IBHQ)

<400> SEQUENCE: 18
attatcagaa ggagccaccc cacaaga 27

<210> SEQ ID NO 19
<211> LENGTH: 22
<212> TYPE: DNA
<213> ORGANISM: Artificial Sequence
<220> FEATURE:
<223> OTHER INFORMATION: Alb-F Primer Sequence

<400> SEQUENCE: 19
gctgtcatct cttgtgggct gt 22

<210> SEQ ID NO 20
<211> LENGTH: 21
<212> TYPE: DNA
<213> ORGANISM: Artificial Sequence
<220> FEATURE:
<223> OTHER INFORMATION: Alb-R Primer Sequence

<400> SEQUENCE: 20

-continued actcatggga gctgctggtt c                                                    21

<210> SEQ ID NO 21
<211> LENGTH: 26
<212> TYPE: DNA
<213> ORGANISM: Artificial Sequence
<220> FEATURE:
<223> OTHER INFORMATION: Alb-P Primer Sequence
<220> FEATURE:
<221> NAME/KEY: misc_feature
<222> LOCATION: (1)..(1)
<223> OTHER INFORMATION: Fluorescein Amidite (FAM)
<220> FEATURE:
<221> NAME/KEY: misc_feature
<222> LOCATION: (26)..(26)
<223> OTHER INFORMATION: Iowa Black Hole Quencher (IBHQ)

<400> SEQUENCE: 21
ggagagattt gtgtgggcat gacagg                                               26

<210> SEQ ID NO 22
<211> LENGTH: 458
<212> TYPE: PRT
<213> ORGANISM: Homo sapiens
<220> FEATURE:
<221> NAME/KEY: SITE
<222> LOCATION: (1)..(25)
<223> OTHER INFORMATION: Signal Peptide
<220> FEATURE:
<221> NAME/KEY: SITE
<222> LOCATION: (1)..(396)
<223> OTHER INFORMATION: Extracellular
<220> FEATURE:
<221> NAME/KEY: SITE
<222> LOCATION: (1)..(92)
<223> OTHER INFORMATION: gp120 binding region
<220> FEATURE:
<221> NAME/KEY: SITE
<222> LOCATION: (1)..(458)
<223> OTHER INFORMATION: UniProtKB/Swiss-Prot: P01730.1
<220> FEATURE:
<221> NAME/KEY: SITE
<222> LOCATION: (26)..(125)
<223> OTHER INFORMATION: Domain 1 (D1)
<220> FEATURE:
<221> NAME/KEY: SITE
<222> LOCATION: (126)..(203)
<223> OTHER INFORMATION: Domain 2 (D2)
<220> FEATURE:
<221> NAME/KEY: SITE
<222> LOCATION: (204)..(317)
<223> OTHER INFORMATION: Domain 3 (D3)
<220> FEATURE:
<221> NAME/KEY: SITE
<222> LOCATION: (318)..(374)
<223> OTHER INFORMATION: Domain 4 (D4)
<220> FEATURE:
<221> NAME/KEY: SITE
<222> LOCATION: (397)..(418)
<223> OTHER INFORMATION: Transmembrane Domain
<220> FEATURE:
<221> NAME/KEY: SITE
<222> LOCATION: (419)..(458)
<223> OTHER INFORMATION: Cytoplasmic Domain

<400> SEQUENCE: 22

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

```
Ile Gln Phe His Trp Lys Asn Ser Asn Gln Ile Lys Ile Leu Gly Asn
 50                  55                  60

Gln Gly Ser Phe Leu Thr Lys Gly Pro Ser Lys Leu Asn Asp Arg Ala
 65                  70                  75                  80

Asp Ser Arg Arg Ser Leu Trp Asp Gln Gly Asn Phe Pro Leu Ile Ile
                 85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
            195                 200                 205

Ser Ile Val Tyr Lys Lys Glu Gly Glu Gln Val Glu Phe Ser Phe Pro
210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
                260                 265                 270

Gln Met Gly Lys Lys Leu Pro Leu His Leu Thr Leu Pro Gln Ala Leu
            275                 280                 285

Pro Gln Tyr Ala Gly Ser Gly Asn Leu Thr Leu Ala Leu Glu Ala Lys
            290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
            355                 360                 365

Gln Cys Leu Leu Ser Asp Ser Gly Gln Val Leu Leu Glu Ser Asn Ile
            370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
            435                 440                 445

His Arg Phe Gln Lys Thr Cys Ser Pro Ile
450                 455
```